US 9,504,694 B2

(12) United States Patent
Junutula et al.

(10) Patent No.: US 9,504,694 B2
(45) Date of Patent: Nov. 29, 2016

(54) ISOQUINOLIDINOBENZODIAZEPINES

(71) Applicant: Cellerant Therapeutics, Inc., San Carlos, CA (US)

(72) Inventors: Jagath R. Junutula, Fremont, CA (US); Vasu Jammalamadaka, Pleasanton, CA (US)

(73) Assignee: Cellerant Therapeutics, Inc., San Carlos, CA (US)

( * ) Notice: Subject to any disclaimer, the term of this patent is extended or adjusted under 35 U.S.C. 154(b) by 0 days.

(21) Appl. No.: 15/048,865

(22) Filed: Feb. 19, 2016

(65) Prior Publication Data

US 2016/0271142 A1  Sep. 22, 2016

Related U.S. Application Data

(60) Provisional application No. 62/135,380, filed on Mar. 19, 2015.

(51) Int. Cl.
*C07D 403/12* (2006.01)
*A61K 31/551* (2006.01)
*C07D 519/00* (2006.01)
*C07K 5/062* (2006.01)
*A61K 47/48* (2006.01)
*C07K 16/30* (2006.01)
*A61K 39/00* (2006.01)

(52) U.S. Cl.
CPC .......... *A61K 31/551* (2013.01); *A61K 47/4863* (2013.01); *C07D 519/00* (2013.01); *C07K 5/06052* (2013.01); *C07K 16/3061* (2013.01); *A61K 2039/505* (2013.01); *C07K 2317/24* (2013.01); *C07K 2317/56* (2013.01)

(58) Field of Classification Search
CPC .................................................. C07D 403/12
See application file for complete search history.

(56) References Cited

U.S. PATENT DOCUMENTS

| 3,860,600 | A  | 1/1975  | Carabateas |
| 8,592,576 | B2 | 11/2013 | Howard et al. |
| 2008/0090812 | A1 | 4/2008 | Pepper et al. |
| 2013/0266596 | A1 | 10/2013 | Li et al. |
| 2013/0302357 | A1 | 11/2013 | Li et al. |
| 2014/0088089 | A1 | 3/2014 | Chari |
| 2016/0200742 | A1 | 7/2016 | Zhang et al. |

FOREIGN PATENT DOCUMENTS

| WO | 93/18045 A1 | 9/1993 |
| WO | 2004/087716 A1 | 10/2004 |
| WO | 2010091150 A1 | 8/2010 |
| WO | 2012112687 A1 | 8/2012 |

(Continued)

OTHER PUBLICATIONS

Al, et al., "Low temperature solid oxide fuel cells based on $Sm_{0.2}Ce_{0.8}O_{1.9}$ films fabricated by slurry spin coating," *Journal of Power Sources*, vol. 159, pp. 637-640 (2006).

(Continued)

*Primary Examiner* — Bruck Kifle
(74) *Attorney, Agent, or Firm* — Kilpatrick Townsend and Stockton LLP

(57) ABSTRACT

This disclosure provides novel isoquinolidinobenzodiazepines. These compounds can also be incorporated into antibody-drug conjugates.

30 Claims, 32 Drawing Sheets

Formula I

Formula II

(56) References Cited

FOREIGN PATENT DOCUMENTS

| WO | 2013177481 A1 | 11/2013 |
|---|---|---|
| WO | 2014031566 A1 | 2/2014 |
| WO | 2014057115 A1 | 4/2014 |
| WO | 2016115191 A1 | 7/2016 |
| WO | 2016115201 A1 | 7/2016 |

OTHER PUBLICATIONS

Brett, et al., "Intermediate temperature solid oxide fuel cells," *Chem. Soc. Rev.*, vol. 37, pp. 1568-1578 (2008).

Brulikova, et al., "DNA Interstrand Cross-Linking Agents and their Chemotherapeutic Potential," *Current Medicinal Chemistry*, vol. 19, pp. 364-385 (2012).

Chen, et al., "Assessment of $Ba_{0.5}Sr_{0.5}Co_{1-y}Fe_yO_{3-\delta}$ (y = 0.0-1.0) for prospective application as cathode for IT-SOFCs or oxygen permeating membrane," *Electrochimica Acta*, vol. 52, pp. 7343-7351 (2007).

Hartley, et al., "SJG-136 (NSC 694501), a Novel Rationally Designed DNA Minor Groove Interstrand Cross-Linking Agent with Potent and Broad Spectrum Antitumor Activity: Part 1: Cellular Pharmacology, In vitro and Initial In vivo Antitumor Activity," *Cancer Res.*, vol. 64(18), pp. 6693-6699 (2004).

Haworth, et al., "Combined investigation of bulk diffusion and surface exchange parameters of silver catalyst coated yttrium-doped BSCF membranes," *Phys. Chem. Chem. Phys.*, vol. 14, pp. 9104-9111 (2012).

Ishihara, et al., "Intermediate Temperature Solid Oxide Fuel Cells Using a New $LaGaO_3$ Based Oxide Ion Conductor," *J. Electrochem. Soc.*, vol. 145, No. 9, pp. 3177-3183 (1998).

Jung, et al., "High Electrochemical Activity of $Bi_2O_3$-based Composite SOFC Cathodes," *Journal of the Korean Ceramic Society*, vol. 51, No. 4, pp. 278-282 (2014).

Kamal, et al., "Design, Synthesis, and Evaluation of New Noncross-Linking Pyrrolobenzodiazepine Dimers with Efficient DNA Binding Ability and Potent Antitumor Activity," *J. Med. Chem.*, vol. 45 (21), pp. 4679-4688 (2002).

Kuo, et al., "Oxidation-Reduction Behavior of Undoped and Sr-Doped $LaMnO_3$: Defect Structure, Electrical Conductivity, and Thermoelectric Power," *Journal of Solid State Chemistry*, vol. 87, pp. 55-63 (1990).

Li, et al., "Thermal, electrical, and electrochemical properties of Nd-doped $Ba_{0.5}Sr_{0.5}Co_{0.8}Fe_{0.2}O_{3-\delta}$ as a cathode material for SOFC," *Solid State Ionics*, vol. 178, pp. 1853-1858 (2008).

Ma, et al., "Study of the Mixed-Conducting $SrFeCo_{0.5}O_y$ System," *J. Am. Ceram. Soc.*, vol. 85(11), pp. 2641-2645 (2002).

Murray, et al., "Electrochemical performance of $(La,Sr)(Co,Fe)O_3$-$(Ce,Gd)O_3$composite cathodes," *Solid State Ionics*, vol. 148, pp. 27-34 (2002).

Nguyen, et al., "Application of $Sm_{0.5}Sr_{0.5})CoO_3$ as a Cathode Material to $(Zr,Sc)O_2$ Electrolyte with Ceria-Based Interlayers for Reduced-Temperature Operation SOFCs," *Journal of The Electrochemical Society*, vol. 153(7), A1310-A1316 (2006).

Ralph, et al., "Cathode Materials for Reduced-Temperature SOFCs," *Journal of The Electrochemical Society*, vol. 150(11), A1518-A1522 (2003).

Shao, et al., "A high-performance cathode for the next generation of solid-oxide fuel cells," *Nature*, vol. 43, pp. 170-173 (2004).

Tai, et al., "Structure and electrical properties of $La_{1-x}Sr_xCo_{1-y}Fe_yO_3$. Part 2. The system $La_{1-x}Sr_xCo_{0.2}Fe_{0.8}O_3$," *Solid State Ionics*, vol. 76, pp. 273-283 (1995).

Tercel, et al., "Unsymmetrical DNA Cross-Linking Agents: Combination of the CBI and PBD Pharmacophores" *Journal of Medicinal Chemistry*, vol. 46(11), pp. 2132-2151 (2003).

Usiskin, et al., "Electronic Behavior of $Ba_{0.5}Sr_{0.5}Co_{0.8}Fe_{0.2}O_{3-d}$ and $SrCo_{0.9}Nb_{0.1}O_{3-d}$," 2011 MRS Spring Meeting, 6 pages (2011).

Xia, et al., "$Sm_{0.5}Sr_{0.5}CoO_3$ cathodes for low-temperature SOFCs," *Solid State Ionics*, vol. 149, pp. 11-19 (2002).

Yan, et al., "Investigation of $Ba_{1-x}Sr_xCo_{0.8}Fe_{0.2}O_{3-\delta}$ as cathodes for low-temperature solid oxide fuel cells both in the absence and presence of $CO_2$," *Journal of Power Sources*, vol. 185, pp. 76-84 (2008).

Zhang, et al., "A novel $Nb_2O_5$-doped $SrCo_{0.8}Fe_{0.2}O_{3-\delta}$ oxide with high permeability and stability for oxygen separation," *Journal of Membrane Science*, vol. 405-406, pp. 300-309 (2012).

Agarwal, et al. 'Site-specific antibody-drug conjugates: the nexus of bioorthogonal chemistry, protein engineering, and drug development' Bioconjugate chemistry, 2015, vol. 26(2), pp. 176-192. [Published Online Dec. 12, 2014] p. 181, col. 2, para 4 to p. 183, para 1; p. 188, col. 1, para 2; p. 188, col. 2, para 2; Fig 3: Fig 4: Fig 5.

International Search Report and Written Opinion from PCT/US2016/22961 mailing date of Aug. 26, 2016.

FIG. 1
Formula I 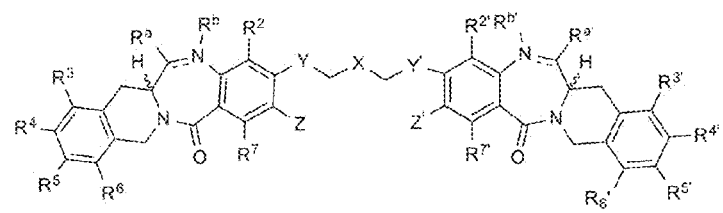
Formula II 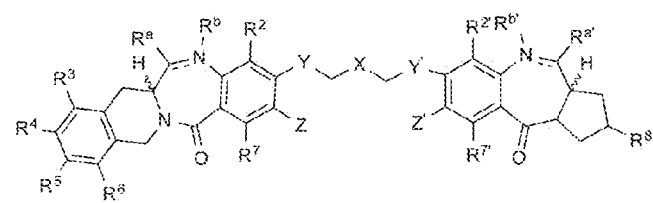

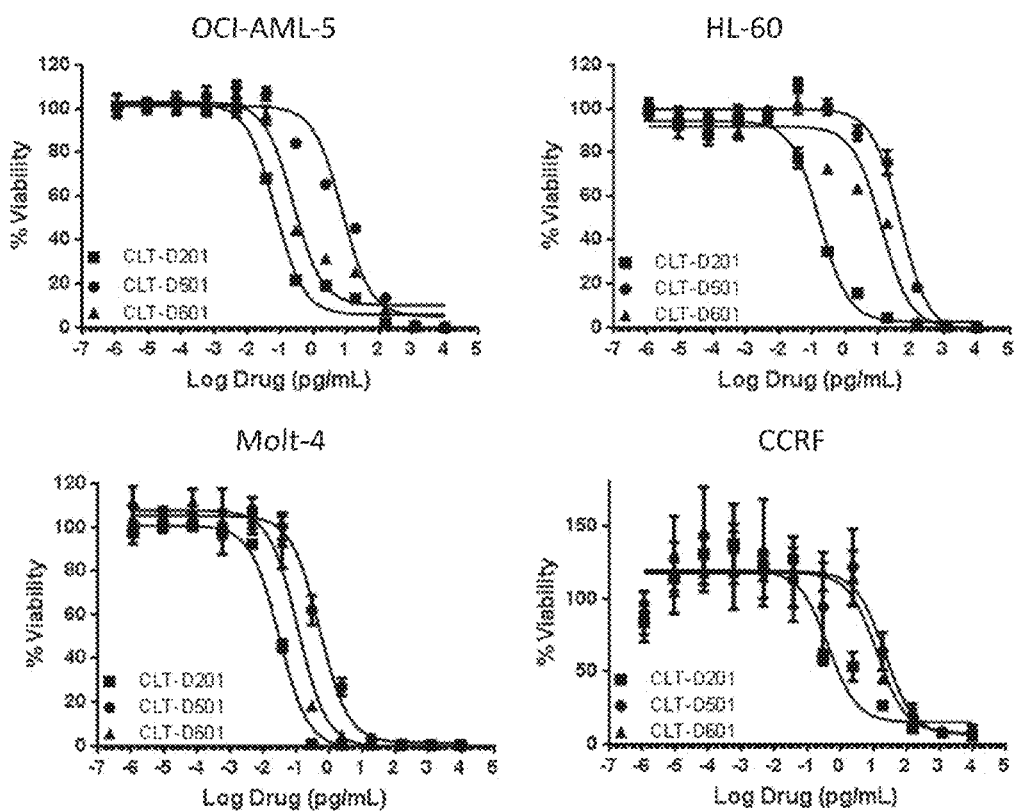
FIG. 10  IQB Payloads – Cytotoxicity on Leukemia Cell lines

FIG. 11  IQB Payloads – Cytotoxicity on Lymphoma Cell line
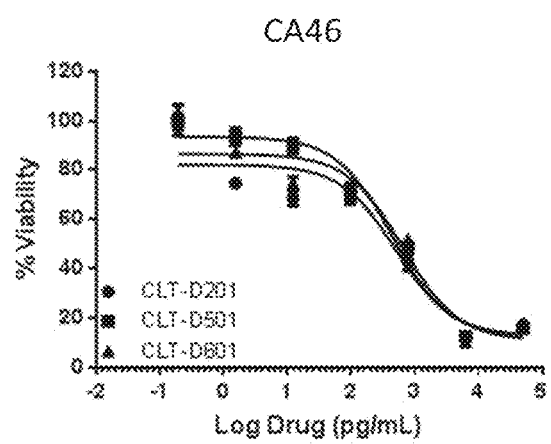

FIG. 12      GI$_{50}$ Values of IQB Payloads on Leukemia and Lymphoma Cell lines

| CELLS | DISEASE | GI-D05 | GI-D10 | GI-D01 |
|---|---|---|---|---|
| OCI-AML-5 | acute myeloid leukemia (AML M4) | 0.07 | 7.76 | 0.26 |
| HL-60 | acute promyelocytic leukemia | 0.18 | 48.98 | 13.37 |
| MOLT-4 | acute lymphoblastic leukemia | 0.03 | 0.53 | 0.12 |
| CCRF-CEM | acute lymphoblastic leukemia | 0.44 | 22.59 | 13.34 |
| CA46 | Burkitt's lymphoma | 507.0 | 441.6 | 642.7 |

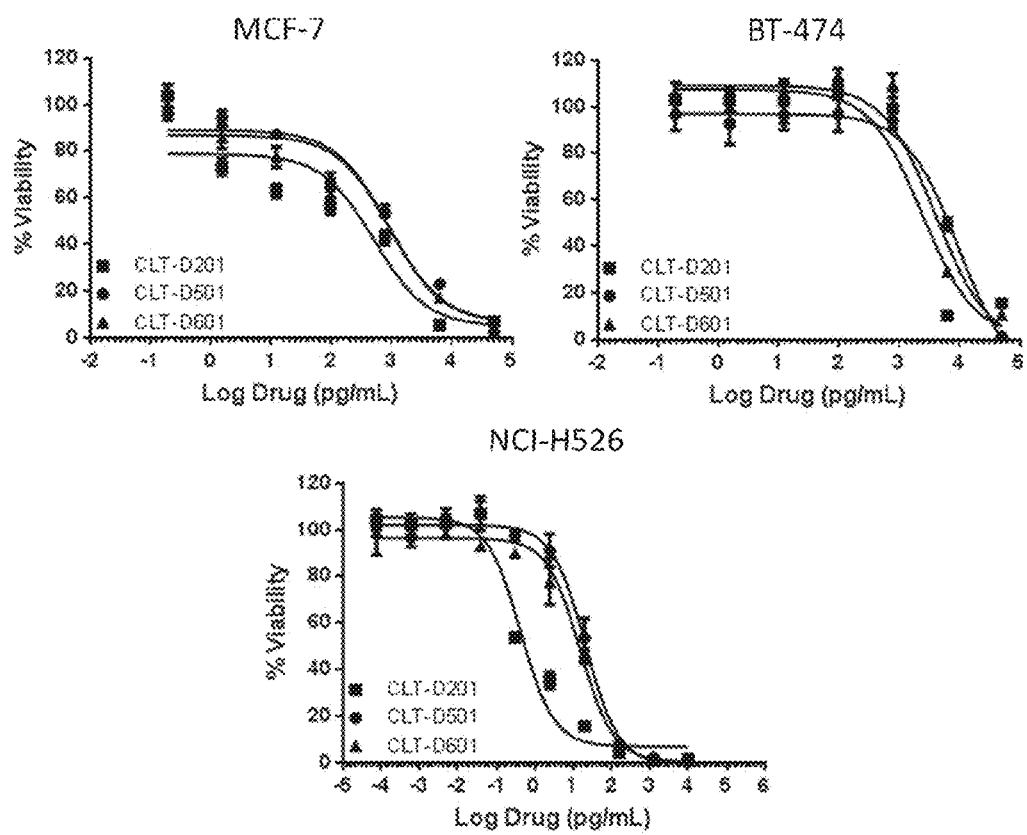
FIG. 13    IQB Payloads – Cytotoxicity of Solid Tumor Cell lines

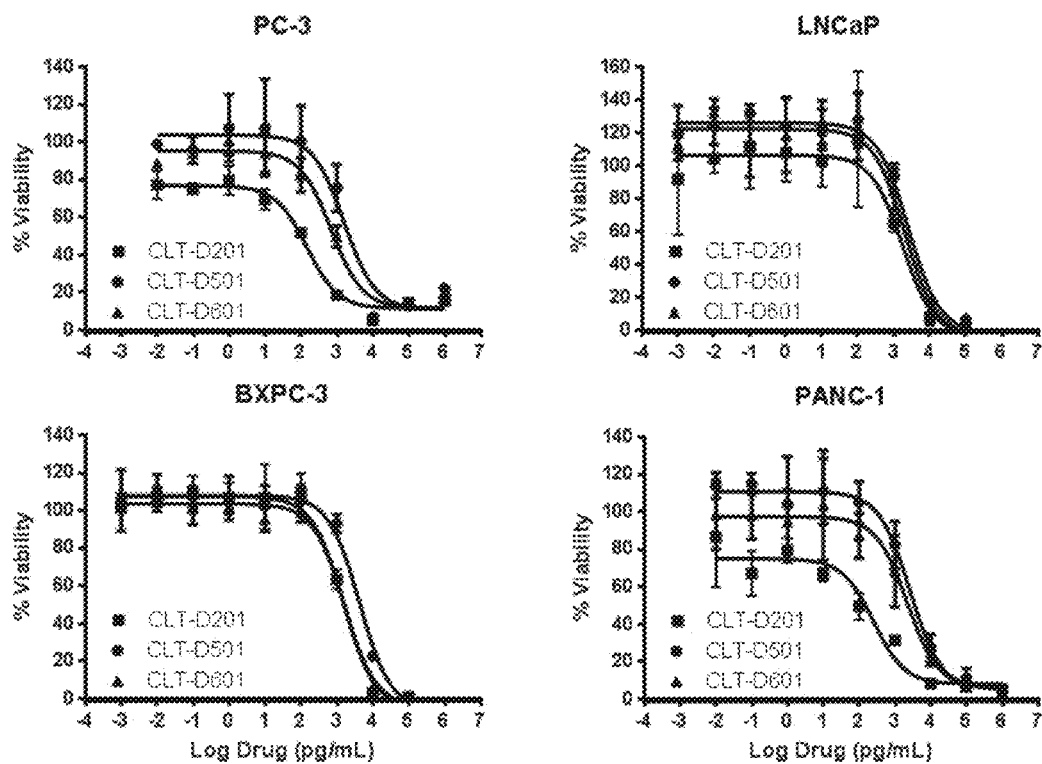
FIG. 14  IQB Payloads – Cytotoxicity of Solid Tumor Cell lines

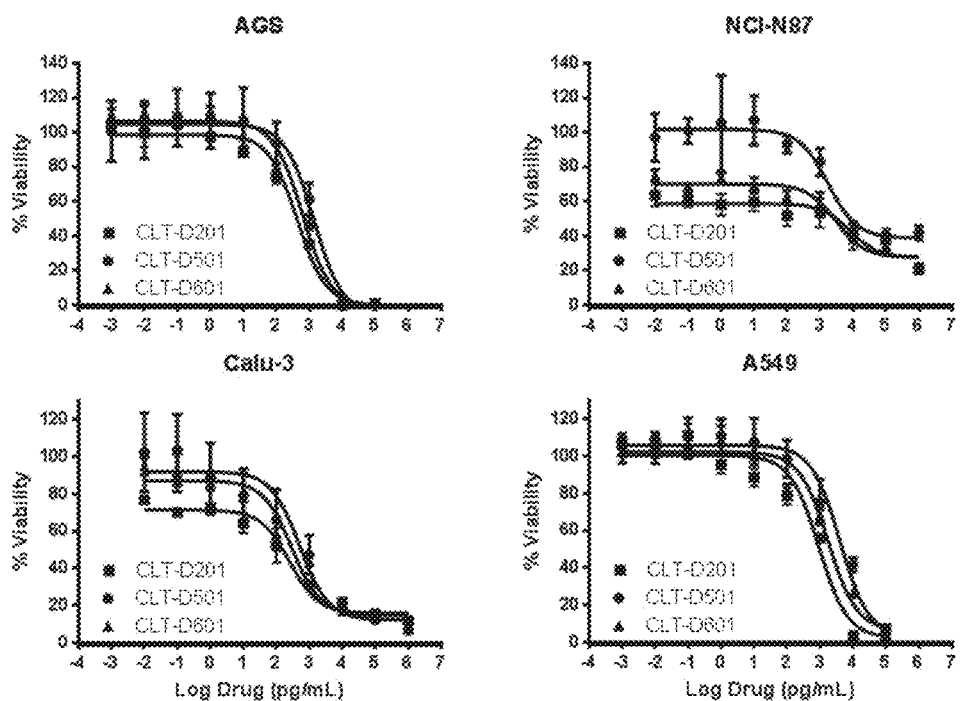
FIG. 15    IQB Payloads – Cytotoxicity of Solid Tumor Cell lines

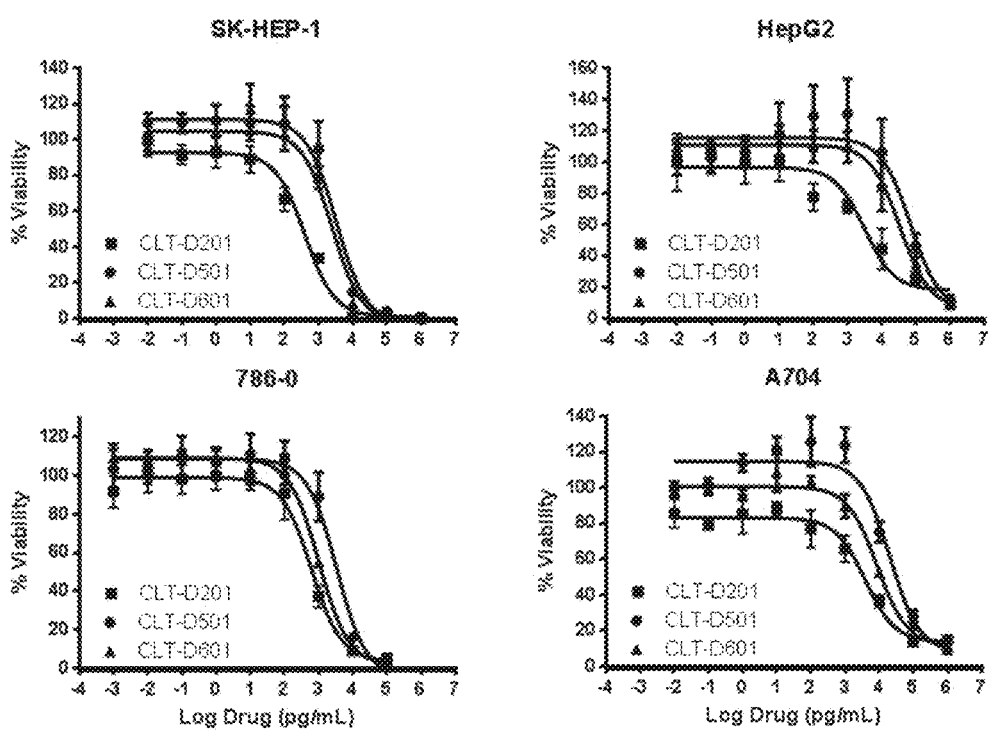
FIG. 16  IQB Payloads – Cytotoxicity of Solid Tumor Cell lines

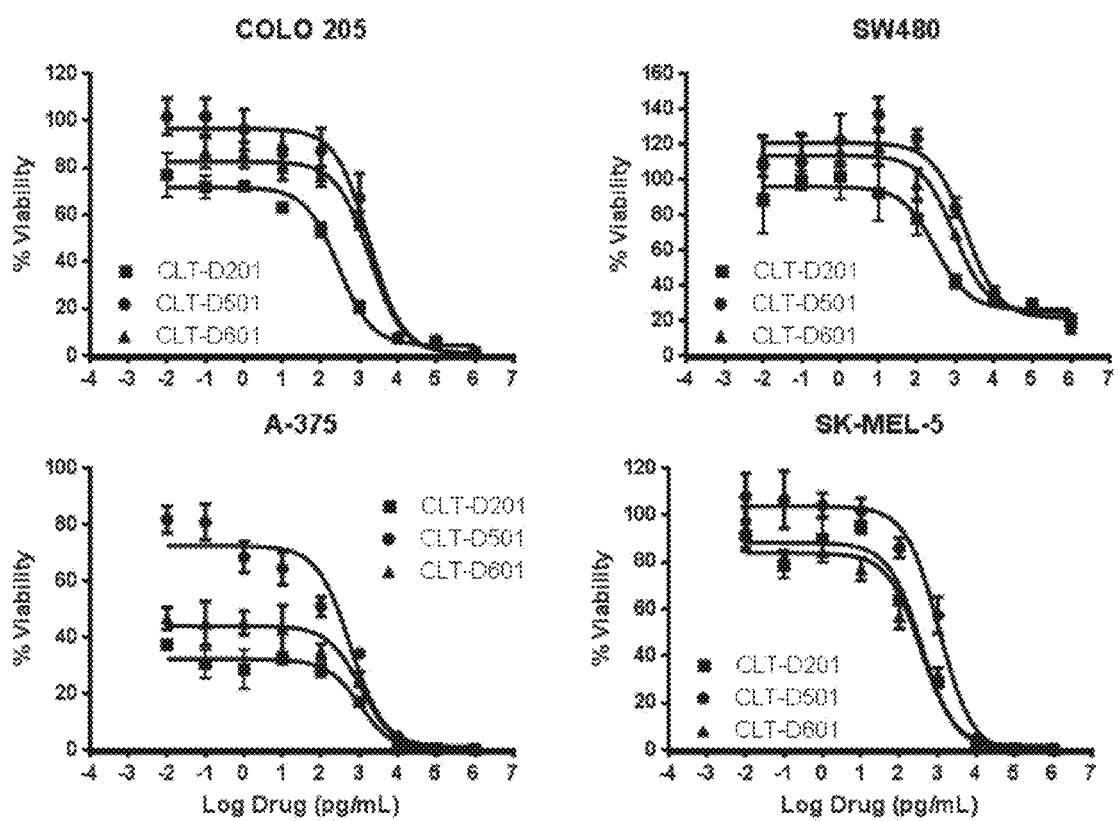
FIG. 17  IQB Payloads — Cytotoxicity of Solid Tumor Cell lines

FIG. 18  Summary of $GI_{50}s$ (pg/mL) on Solid Tumor Cell lines

| Cell Line | Disease | CLRD201 | CLRD501 | CLRD101 |
|---|---|---|---|---|
| MCF7 | Breast adenocarcinoma/ER+ | 511.7 | 891.3 | 935.4 |
| BT-474 | Breast ductal carcinoma/HER-2+ & ER+ | 2387.8 | 9375.6 | 4027.2 |
| NCI-H526 | Small cell lung cancer | 0.4 | 20.7 | 15.2 |
| PC-3 | Prostate adenocarcinoma | 150 | 1570 | 690 |
| LNCaP | Prostate carcinoma | 1740 | 2600 | 2000 |
| BXPC-3 | Pancreatic adenocarcinoma | 1520 | 4370 | 1620 |
| PANC-1 | Pancreatic epithelioid carcinoma | 250 | 2640 | 1650 |
| AGS | Gastric adenocarcinoma | 430 | 1360 | 610 |
| NCI-N87 | Gastric carcinoma | 8080 | 1580 | 2920 |
| Calu-3 | Lung adenocarcinoma | 250 | 620 | 290 |
| A549 | Lung carcinoma | 910 | 3960 | 1750 |
| SK-HEP-1 | Liver adenocarcinoma | 400 | 3310 | 2440 |
| HepG2 | Liver carcinoma | 3130 | 69260 | 33690 |
| 786-0 | Renal cell adenocarcinoma | 620 | 3310 | 1010 |
| A704 | Kidney adenocarcinoma | 3840 | 20200 | 8730 |
| COLO 205 | Colorectal adenocarcinoma | 280 | 1720 | 1850 |
| SW480 | Colorectal adenocarcinoma | 300 | 1750 | 940 |
| A-375 | Melanoma | 1050 | 610 | 1110 |
| SK-MEL-5 | Melanoma | 380 | 1070 | 360 |

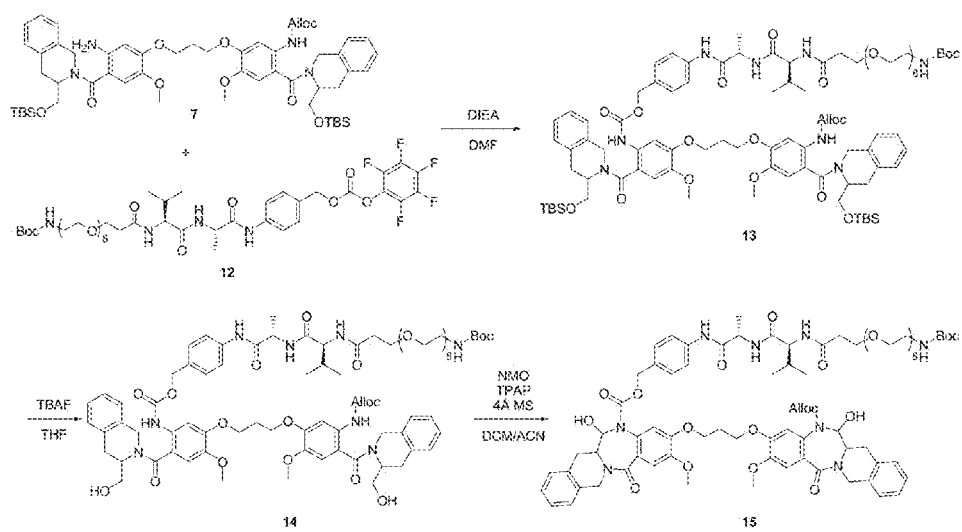

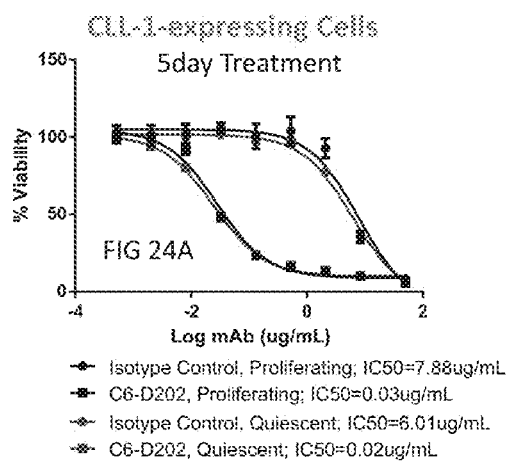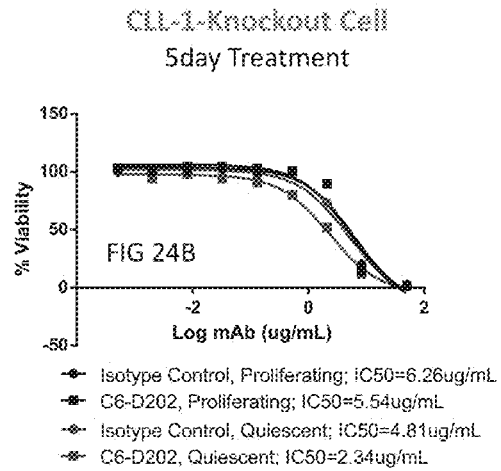

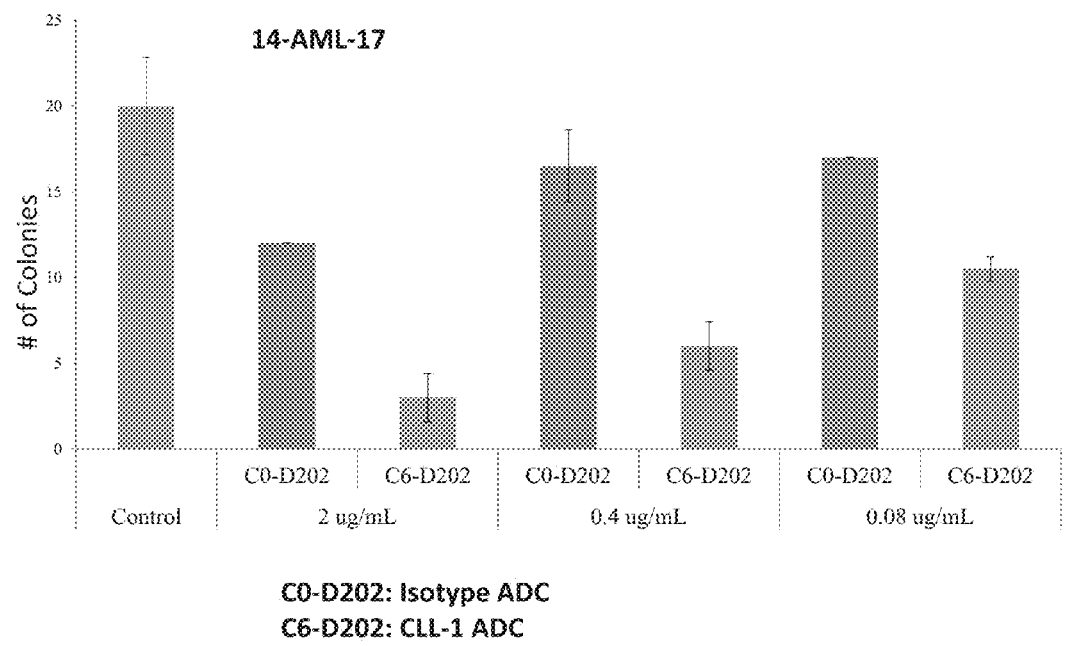

ISOQUINOLIDINOBENZODIAZEPINES

REFERENCE TO RELATED APPLICATIONS

This application is related to U.S. Ser. No. 62/135,380, filed Mar. 19, 2015, incorporated herein by reference.

STATEMENT AS TO FEDERALLY SPONSORED RESEARCH

None.

REFERENCE TO SUBMISSION OF A SEQUENCE LISTING

The Sequence Listing written in file 0971543_ST25.txt, created on Feb. 19, 2016, 1,868 bytes, machine format IBM-PC, MS-Windows operating system, is hereby incorporated by reference.

BACKGROUND OF THE INVENTION

Benzodiazapines have been used as therapeutics. Benzodiazepine derivatives include pyrrolobenzodiazepines. Pyrrolobenzodiazepine dimers function as DNA cross-linking agents, e.g., by binding in the minor groove of DNA molecules. Certain of these have been suggested as antiproliferative agents in the treatment of cancer.

U.S. Pat. No. 8,592,576 (Howard et al.) refers to unsymmetrical pyrrolobenzodiazepine-dimers asserted for treatment of proliferative diseases.

WO 1993/18045 refers to pyrrolobenzodiazepine derivatives asserted to have cytotoxic activity.

WO 2004/087716 (Kamal et al.) refers to pyrrolo (2,1-C)(1,4) benzodiazepine dimers asserted to be useful as antitumor agents.

US 2008/0090812 (Pepper et al.) refers to a pyrrolobenzodiazepine dimer asserted to be useful for the treatment of leukemias.

US 2013/0266596 (Li et al.) refers to benzodiazepine derivatives asserted to have antiproliferative activity.

US 2014/00888089 (Chari) refers to benzodiazepine derivatives asserted to have antiproliferative activity.

Hartley, John A.; "The development of pyrrolobenzodiazepines as antitumour agents", 2011, Expert Opinion on Investigational Drugs, 20(6), 733-744, refers to pyrrolobenzodiazepines.

Brulikova, L. et al., "DNA interstrand cross-linking agents and their chemotherapeutic potential", Current Medicinal Chemistry, 2012, 19(3), 364-385 refers to DNA interstrand cross-linking agents.

Kamal et al., "Design, Synthesis, and Evaluation of New Noncross-Linking Pyrrolobenzodiazepine Dimers with Efficient DNA Binding Ability and Potent Antitumor Activity" J. Med. Chem., 2002, 45 (21), pp 4679-4688 refers to pyrrolobenzodiazepine chemistry.

Tercel et al., "Unsymmetrical DNA Cross-Linking Agents: Combination of the CBI and PBD Pharmacophores" Journal of Medicinal Chemistry (2003), 46(11), 2132-2151 refers to pyrrolobenzodiazepines.

The statements in this Background are not necessarily meant to endorse the characterization in the cited references.

BRIEF SUMMARY OF THE INVENTION

In one aspect, a compound is provided, having a structure of Formula (I) or (II):

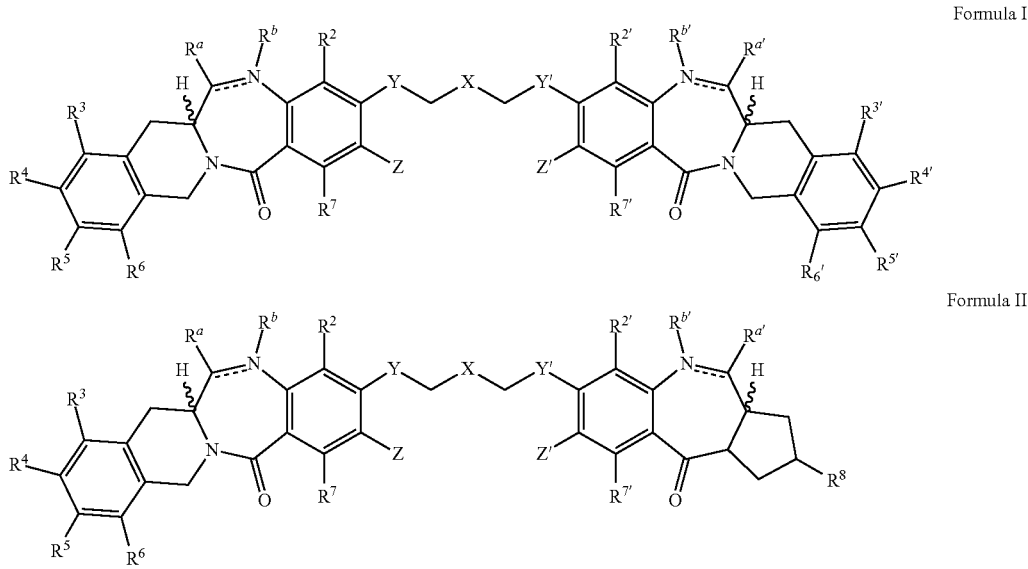

Formula I

Formula II where the dotted bond shown between —C($R^a$)— and —N($R^b$)— or —C($R^{a'}$)— and —N($R^{b'}$)— is independently a single bond or a double bond. When a double bond is present between —C($R^a$)— and —N($R^b$)—, the —C($R^a$)— is olefinic and has a substituent $R^a$ and $R^b$ of the —N($R^b$)— is not present. When a single bond is present between —C($R^a$)— and —N(Rb)—, the —C($R^a$)— is saturated and has a hydrogen substituent in addition to the $R^a$ substituent and $R^b$ of the —N($R^b$)— is present. When a double bond is present between —C($R^{a'}$)— and —N($R^{b'}$)—, the —C($R^{a'}$)— is olefinic and has a substituent $R^{a'}$ and $R^{b'}$ of the —N($R^{b'}$)— is not present. When a single bond is present between —C($R^{a'}$)— and —N($R^{b'}$)—, the —C($R^{a'}$)— is saturated and has a hydrogen substituent in addition to the $R^{a'}$ substituent and $R^{b'}$ of the —N($R^{b'}$)— is present.

Each of $R^a$ and $R^{a'}$ is independently H, OH, or —O—P, where P is a protecting group. If present, each of $R^b$ and $R^{b'}$ is independently H, L-$R_x$ or L-$S_c$; $R^2$, $R^{2'}$, $R^3$, $R^{3'}$, $R^4$, $R^{4'}$, $R^{6'}$ and $R^6$ are each independently selected from H, OH, $C_1$-$C_{10}$ alkyl, $C_2$-$C_{10}$ alkenyl or $C_2$-$C_{10}$ alkynyl; and each of $R^5$ or $R^{5'}$ is independently $NH_2$, $CO_2H$, H, OH $C_1$-$C_{10}$ alkyl, $C_2$-$C_{10}$ alkenyl, $C_2$-$C_{10}$ alkynyl, -L-$R_x$ or -L-$S_c$; each of $R^7$ and $R^{7'}$ is H.

$R^8$ is H, $NH_2$, $CO_2H$, -L-$R_x$, or -L-$S_c$, where the carbon to which $R^8$ is attached also has a hydrogen substituent; or $R^8$ is an exo olefin having the structure

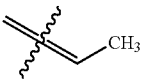

where the carbon to which $R^8$ is attached has no other substituent.

X is $C_{1-12}$ alkylene, optionally where the alkylene chain is interrupted by one or more hetero atoms selected from the group consisting of O, S, and NH; or —$(CH_2)_m$-Q-$(CH_2)_p$—, wherein m and p are each independently 0, 1 or 2.

Q has a structure of formula:

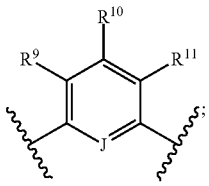

where each of $R^9$, $R^{10}$ and $R^{11}$ is H, $NH_2$, $CO_2H$, -L-$R_x$ or -L-$S_c$; and J is CH or N.

Each of Y and Y' is independently O, S, or NH; and each of Z and Z' is independently H, R, OH, OR, SH, SR, $NH_2$, or NHR, where each R is independently unsubstituted $C_1$-$C_{12}$ alkyl, substituted $C_1$-$C_{12}$ alkyl, unsubstituted $C_3$-$C_{20}$ heterocyclyl, substituted $C_3$-$C_{20}$ heterocyclyl, unsubstituted $C_6$-$C_{20}$ aryl groups, and unsubstituted $C_6$-$C_{20}$ aryl groups.

-L-$R_x$ is a linker L attached to a reactive moiety $R_x$, and -L-$S_c$ is a linker L attached to a substance $S_c$; where L is a bond or is a moiety having 1-200 nonhydrogen atoms selected from C, N, O, S, or halogen, and optionally incorporates ether, oxo, carboxamidyl, urethanyl, branched, cyclic, unsaturated, heterocyclic, aromatic or heteroaromatic moieties; $R_x$ is a reactive moiety; $S_c$ is a target binding agent selected from a protein, a portion of a protein, a peptide or a nucleic acid; and when -L-$R_x$ or -L-$S_c$ is present in the compound of formula I or II, only one of $R^b$, $R^{b'}$, $R^5$, $R^{5'}$, $R^8$, $R^9$, $R^{10}$, and $R^{11}$ is L-$R_x$ or -L-$S_c$.

In some embodiments, Y and Y' may each be O. In other embodiments, Z and Z' may each be independently selected from $C_1$-$C_3$ alkoxy. In some embodiments, Z and Z' are each independently OR, where each R is independently unsubstituted $C_1$-$C_3$ alkyl. In various embodiments, X may be —$CH_2$—. In some embodiments, X may be Q. In some embodiments, when X is Q, then J may be CH.

In various embodiments, one of $R^9$, $R^{10}$ or $R^{11}$ may be -L-$R_x$ or -L-$S_c$.

In some embodiments, the compound may have a structure of formula I, and one of $R^5$ or $R^{5'}$ may be -L-$R_x$ or -L-$S_c$. In other embodiments, the compound may have a structure of formula II, and one of $R^5$ or $R^8$ may be -L-$R_x$ or -L-$S_c$. Alternatively, the compound may have a structure of formula I, and one of $R^b$ or $R^{b'}$ may be -L-$R_x$ or -L-$S_c$. In yet other embodiments, the compound may have a structure of formula II, and one of $R^b$ or $R^{b'}$ may be -L-$R_x$ or -L-$S_c$.

In some embodiments, the compound is the compound of formula I or II wherein each of $R^a$ and $R^{a'}$ is independently H, or OH; if present, each of $R^b$ and $R^{b'}$ is independently H, or L-$R_x$; $R^2$, $R^{2'}$, $R^3$, $R^{3'}$, $R^4$, $R^{4'}$, $R^5$, $R^{5'}$, $R^6$, $R^{6'}$, $R^7$ and $R^{7'}$, are each H; $R^8$ is H; or an exo olefin having the structure

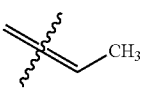 [SMILES: *=CC]

wherein the carbon to which $R^8$ is attached has no other substituent; X is $C_{1-12}$ alkylene; each of Y and Y' is O; each of Z and Z' is independently OR, where each R is independently unsubstituted $C_1$-$C_3$ alkyl; -L-$R_x$ is a linker L attached to a reactive moiety Rx; wherein L is a bond or is a moiety having 1-200 nonhydrogen atoms selected from C, N, O, S, or halogen, and optionally incorporates ether, oxo, carboxamidyl, urethanyl, branched, cyclic, unsaturated, heterocyclic, aromatic or heteroaromatic moieties; $R_x$ is a reactive moiety; and when -L-$R_x$ is present in the compound of formula I or II, only one of $R^b$, and $R^{b'}$ is L-$R_x$.

In some embodiments, the compound is the compound of formula I or II wherein each of $R^a$ and $R^{a'}$ is independently H, or OH; if present, each of $R^b$ and $R^{b'}$ is independently H, L-$R_x$; $R^2$, $R^{2'}$, $R^3$, $R^{3'}$, $R^4$, $R^{4'}$, $R^5$, $R^{5'}$, $R^6$, $R^{6'}$, $R^7$ and $R^{7'}$, are each H; X is $C_{1-12}$ alkylene; each of Y and Y' is O; each of Z and Z' is independently OR, where each R is independently unsubstituted $C_1$-$C_3$ alkyl; -L-$R_x$ is a linker L attached to a reactive moiety Rx; wherein L is a bond or is a moiety having 1-200 nonhydrogen atoms selected from C, N, O, S, or halogen, and optionally incorporates ether, oxo, carboxamidyl, urethanyl, branched, cyclic, unsaturated, heterocyclic, aromatic or heteroaromatic moieties; $R_x$ is a reactive moiety; and when -L-$R_x$ is present in the compound of formula I or II, only one of $R^b$, and $R^{b'}$ is L-$R_x$.

In some embodiments, the compound is the compound of formula I or II wherein $R^a$ is H; $R^{a'}$ is OH; $R^b$ is not present; $R^{b'}$ is L-$R_x$; $R^2$, $R^{2'}$, $R^3$, $R^{3'}$, $R^4$, $R^{4'}$, $R^5$, $R^{5'}$, $R^6$, $R^{6'}$, $R^7$ and $R^{7'}$, are each H; X is $C_{1-12}$ alkylene; each of Y and Y' is O; each of Z and Z' is independently OR, where each R is independently unsubstituted $C_1$-$C_3$ alkyl; -L-$R_x$ is a linker L attached to a reactive moiety Rx; wherein L is a bond or is a moiety having 1-200 nonhydrogen atoms selected from C, N, O, S, or halogen, and optionally incorporates ether, oxo, carboxamidyl, urethanyl, branched, cyclic, unsaturated, heterocyclic, aromatic or heteroaromatic moieties; $R_x$ is a reactive moiety.

In some embodiments, the compound is the compound of formula I or II wherein each of $R^a$ and $R^{a'}$ is independently H, or OH; if present, each of $R^b$ and $R^{b'}$ is independently H, L-$R_x$; $R^2$, $R^{2'}$, $R^3$, $R^4$, $R^5$, $R^6$, $R^7$ and $R^{7'}$, are each H; $R^8$ is: H; or an exo olefin having the structure

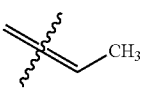 [SMILES: *=CC]

wherein the carbon to which $R^8$ is attached has no other substituent; X is $C_{1-12}$ alkylene; each of Y and Y' is O; each of Z and Z' is independently OR, where each R is independently unsubstituted $C_1$-$C_3$ alkyl; -L-$R_x$ is a linker L attached to a reactive moiety Rx; wherein L is a bond or is a moiety having 1-200 nonhydrogen atoms selected from C, N, O, S, or halogen, and optionally incorporates ether, oxo, carboxamidyl, urethanyl, branched, cyclic, unsaturated, heterocyclic, aromatic or heteroaromatic moieties; $R_x$ is a reactive moiety; and when -L-$R_x$ is present in the compound of formula I or II, only one of $R^b$, and $R^{b'}$ is L-$R_x$.

In some embodiments, the compound is the compound of formula I or II wherein each of $R^a$ and $R^{a'}$ is H; each of $R^b$ and $R^{b'}$ is not present; $R^2$, $R^{2'}$, $R^3$, $R^4$, $R^5$, $R^6$, $R^7$ and $R^{7'}$, are each H; $R^8$ is H; X is $C_{1-12}$ alkylene; each of Y and Y' is O; and each of Z and Z' is independently OR, where each R is independently unsubstituted $C_1$-$C_3$ alkyl.

In some embodiments, the compound of formula I or II has a structure of one of the following formulae:

CLT-201

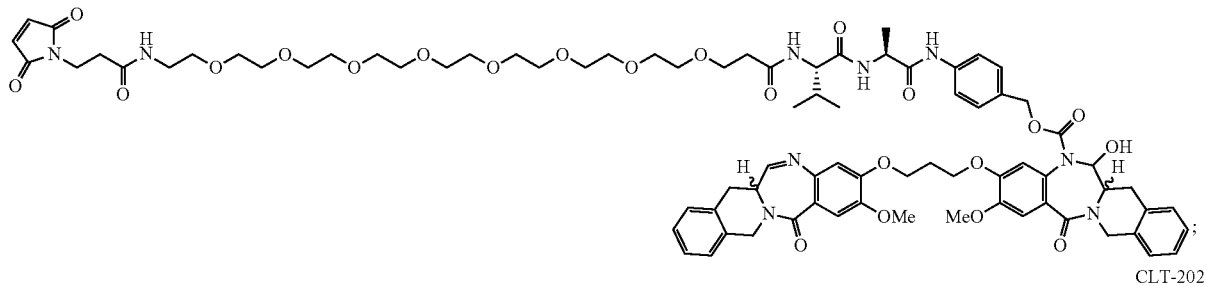

CLT-202

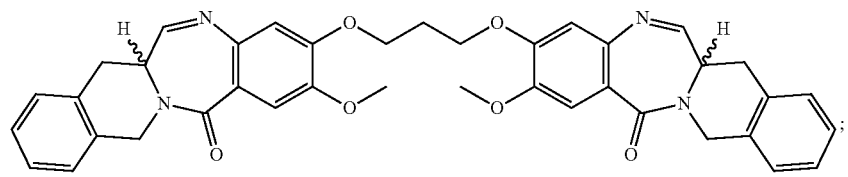

CLT-203

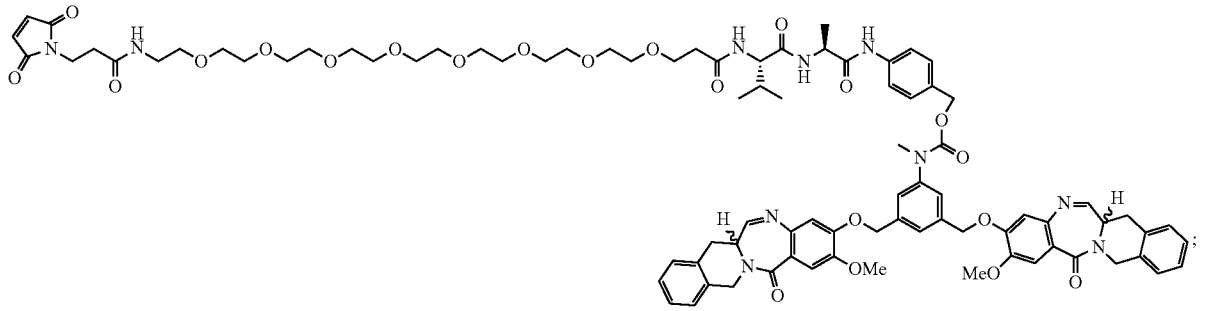

CLT-204

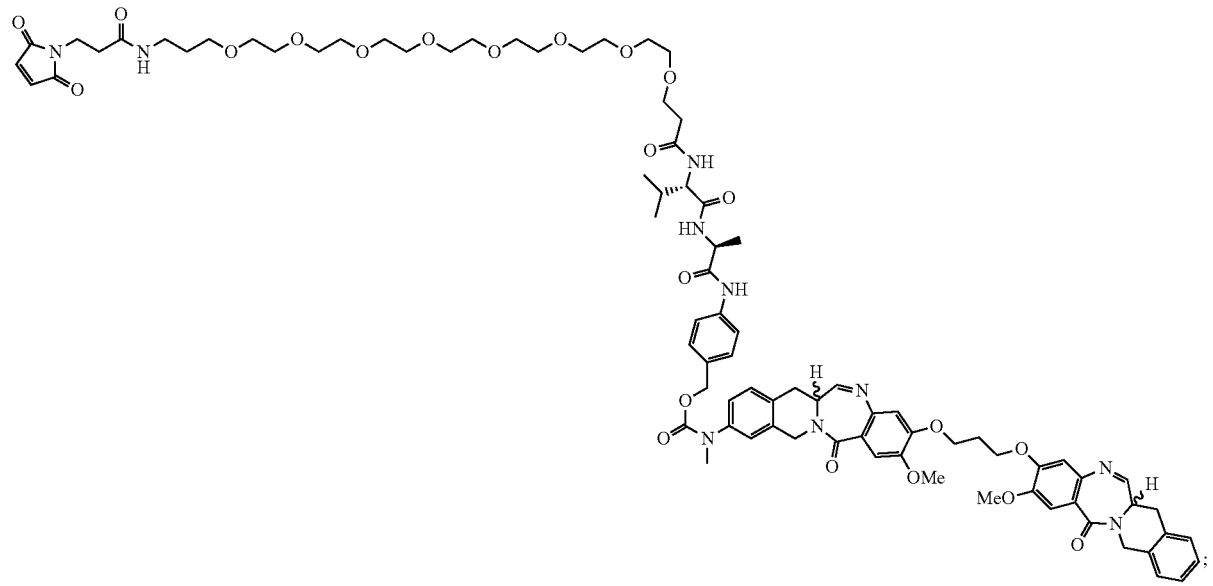

-continued
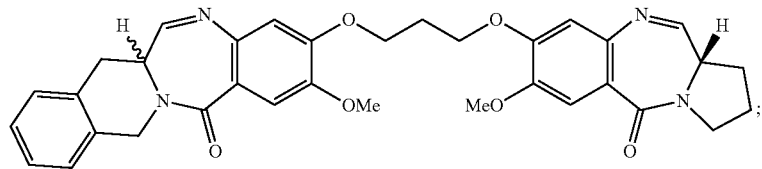
CLT-501
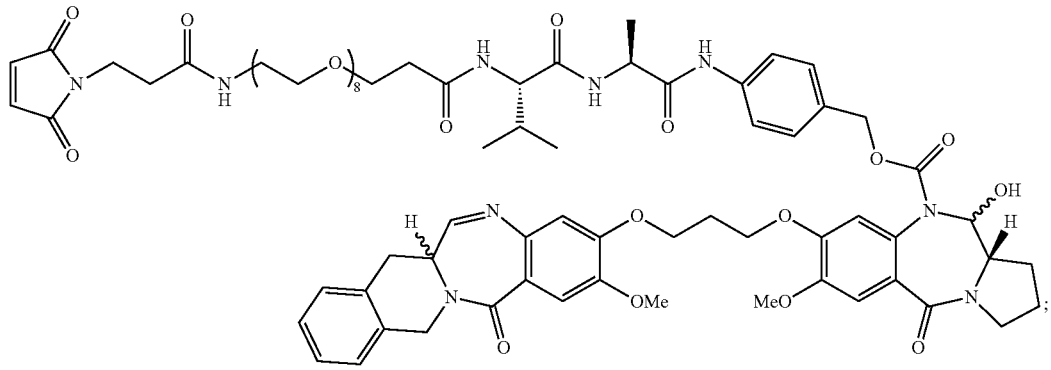
CLT-502
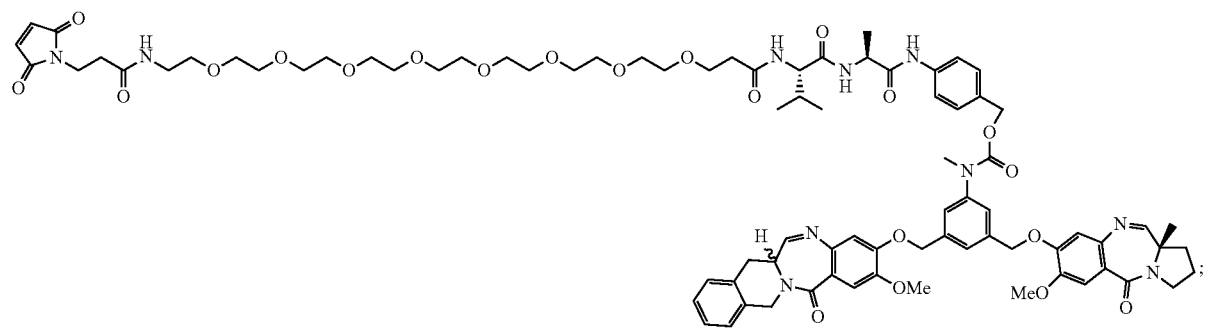
CLT-503
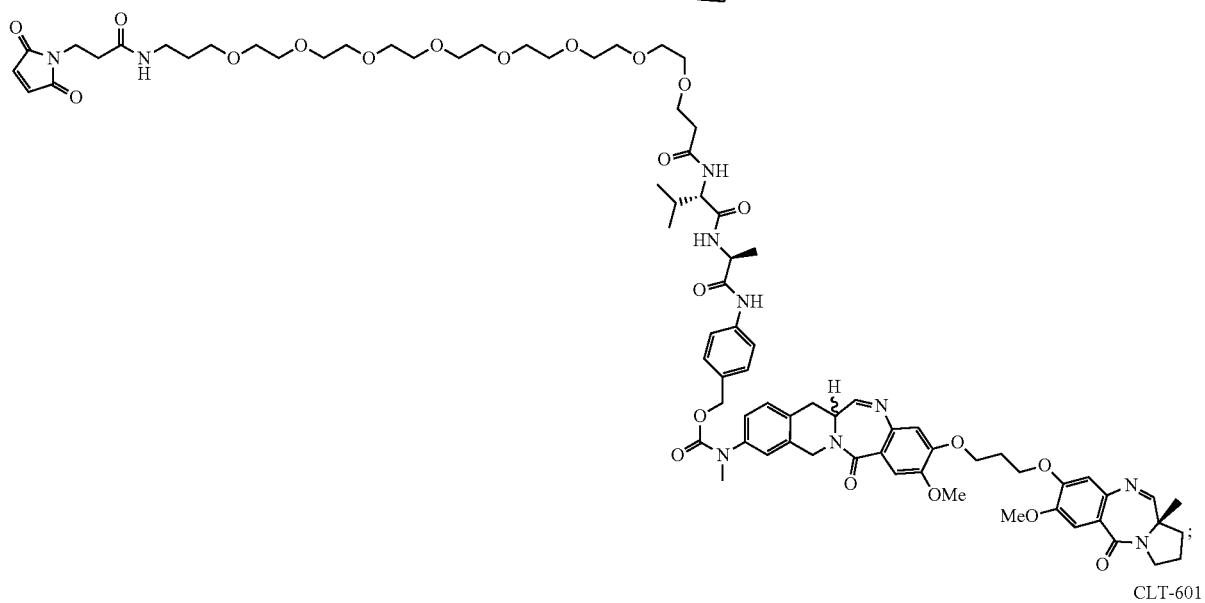
CLT-601
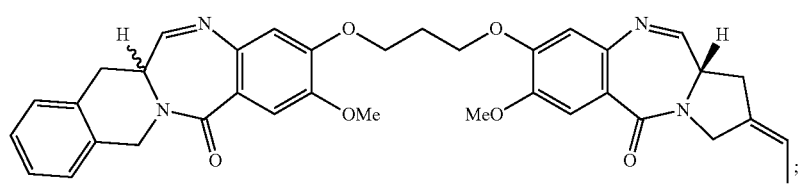

CLT-602
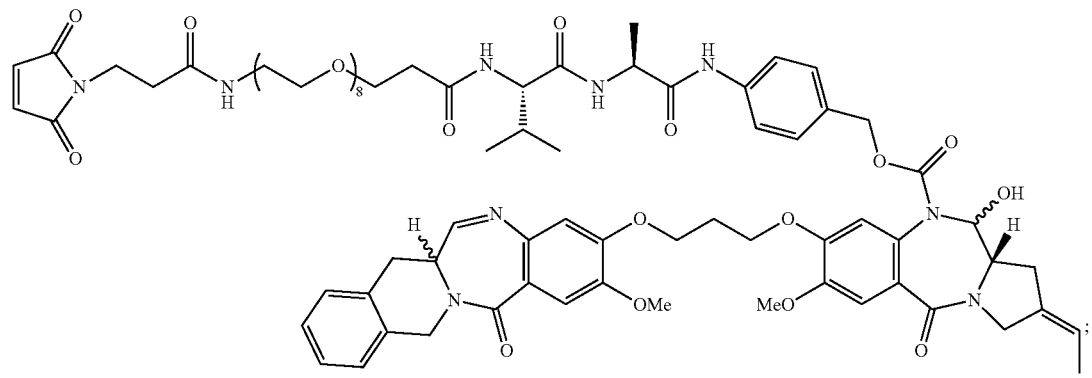
CLT-603
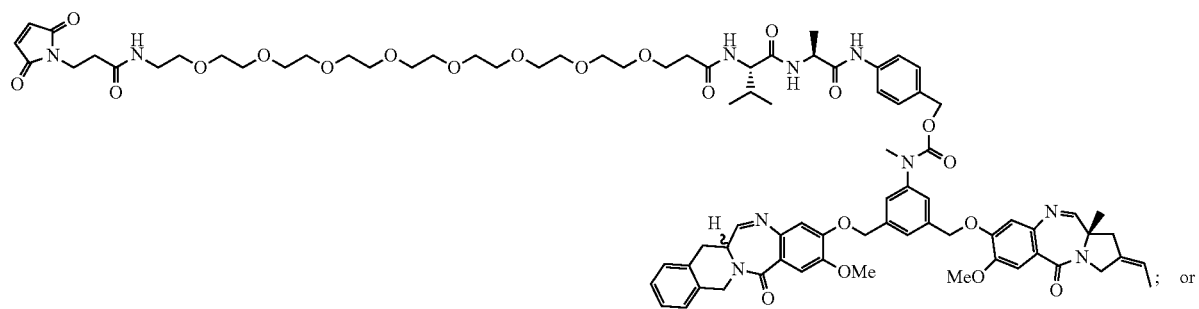
; or
CLT-604
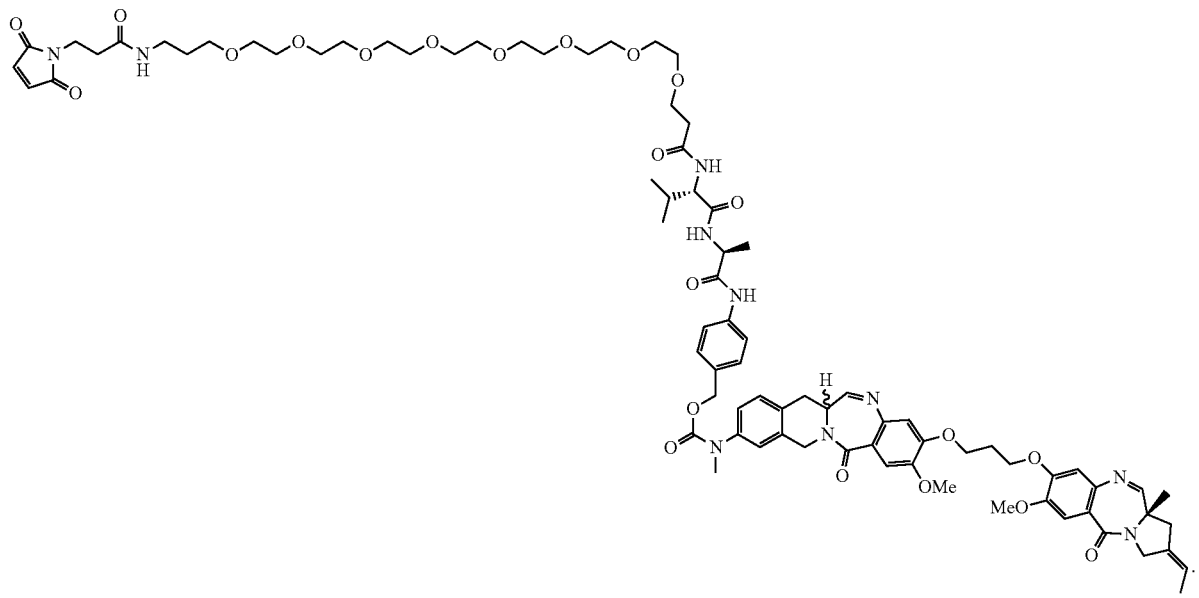

In some embodiments, the compound of formula I or II has a structure of one of the following formulae:
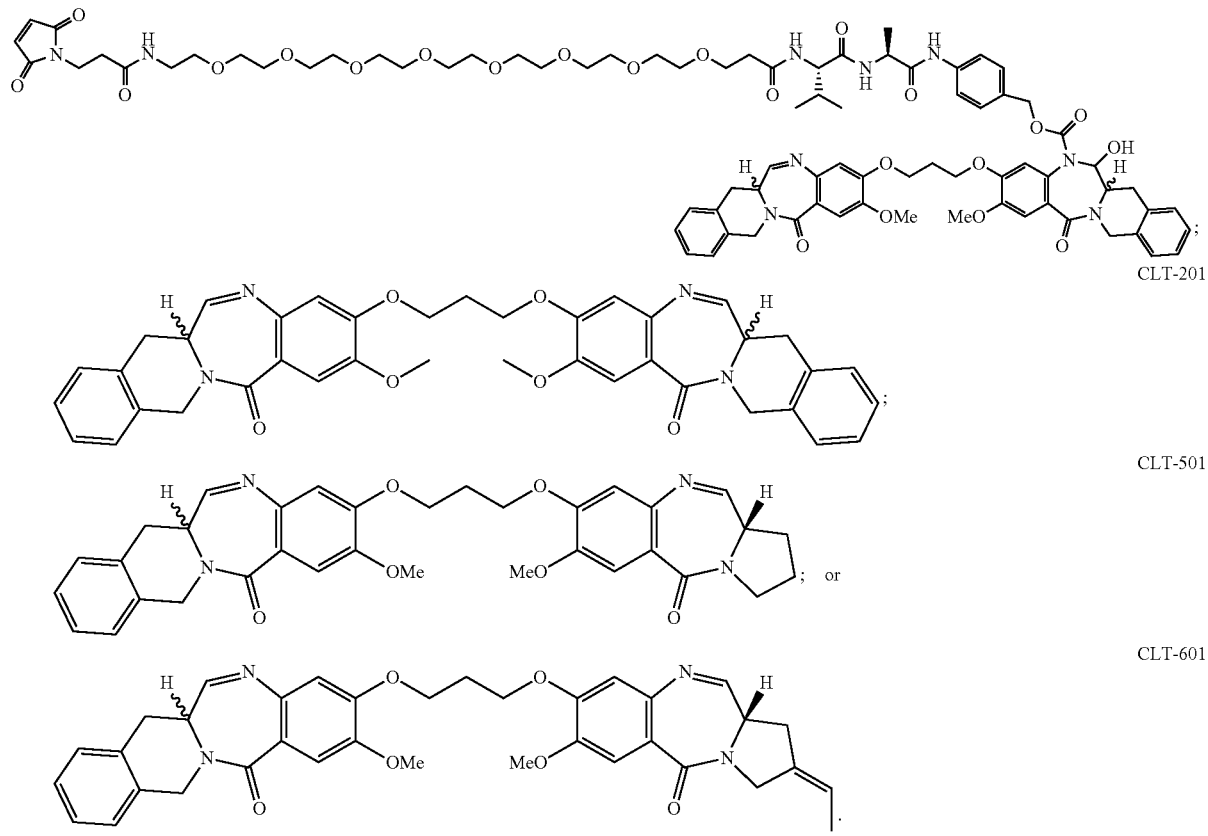
In some embodiments, the compound of formula I has a structure of one of the following formulae:
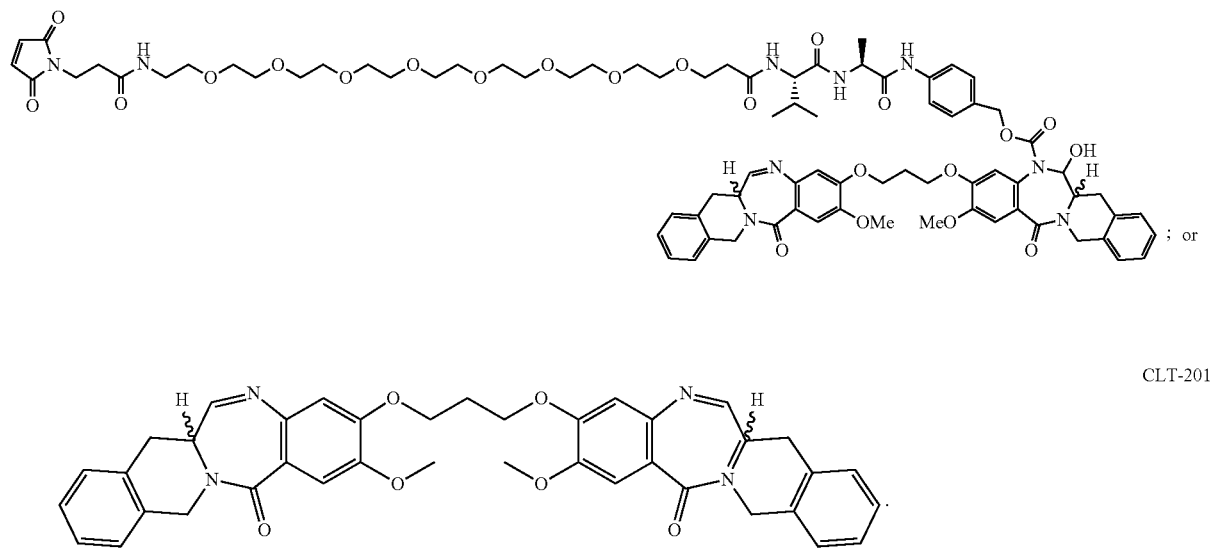

In some embodiments, the compound of formula II has a structure of one of the following formulae:

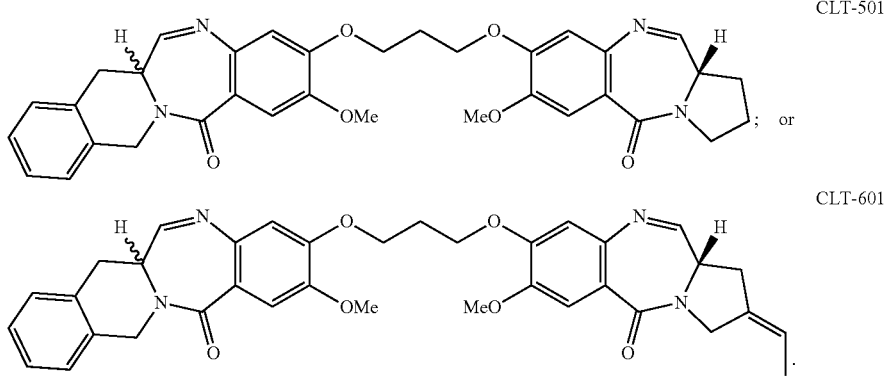

In some embodiments, one of $R^b$, $R^5$, $R^{5'}$, $R^8$, $R^9$, $R^{10}$ or $R^{11}$ may be -L-$R_x$ where $R_x$ may be a moiety that links via a disulfide to a cysteine residue on a target-binding agent. In other embodiments, one of $R^b$, $R^5$, $R^{5'}$, $R^8$, $R^9$, $R^{10}$ or $R^{11}$ is -L-$R_x$ where $R_x$ may be a moiety that links via a maleimide to a cysteine residue on a target-binding agent. In yet other embodiments, one of $R^b$, $R^5$, $R^{5'}$, $R^8$, $R^9$, $R^{10}$ or $R^{11}$ is -L-$R_x$ where $R_x$ may be a moiety that links two cysteine residues on a target-binding agent by reducing a disulfide bond and bridging alkylation of cysteine residues, e.g., linking through bis-sulfone reagent, di-thiopyridylmaleimide or di-bromo maleiemide. In yet other embodiments, one of $R^b$, $R^5$, $R^{5'}$, $R^8$, $R^9$, $R^{10}$ or $R^{11}$ is -L-$R_x$ where $R_x$ may be a moiety that links two cysteine residues on a target-binding agent by reducing a disulfide bond and bridging alkylation of cysteine residues. In some other embodiments, one of $R^b$, $R^5$, $R^{5'}$, $R^8$, $R^9$, $R^{10}$ or $R^{11}$ may be -L-$R_x$ where $R_x$ may be a moiety that links via a succinimide link to a lysine residue on a target-binding agent.

In other embodiments, one of $R^b$, $R^5$, $R^{5'}$, $R^8$, $R^9$, $R^{10}$ or $R^{11}$ may be -L-$R_x$, where $R_x$ may be a moiety that links to an un-natural amino acid residue on a target-binding agent. In some embodiments when $R_x$ is a moiety that links to an un-natural amino acid residue on a target-binding agent, $R_x$ may be a cyclooctyne moiety which links via copper-free click chemistry to an p-azidomethylphenylalanine residue or $R_x$ may be an aminoxy moiety which links to a p-acetyl-phenylalanine residue via oxime condensation.

In some embodiments, one of $R^b$, $R^5$, $R^{5'}$, $R^8$, $R^9$, $R^{10}$ or $R^{11}$ may be -L-$R_x$, where $R_x$ may be a moiety that links to a N-glycan on a target-binding agent through glyco engineering. In some embodiments, when $R_x$ is a moiety that links to a N-glycan on a target-binding agent through glyco engineering, then $R_x$ may be a cyclooctyne moiety which links via copper-free click chemistry to an azido moiety of the target-binding agent where the azido moiety is engineered by enzymatic transfer of galactose and 9-azidosialic acid to a N-glycan. In other embodiments, when $R_x$ is a moiety that links to a N-glycan on a target-binding agent through glyco engineering, then $R_x$ may be an aminoxy moiety which links via oxime condensation to an aldehyde moiety of the target binding agent where the aldehyde is engineered by enzymatic transfer of galactose and sialic acid to a N-glycan followed by periodate oxidation.

In some embodiments, one of $R^b$, $R^5$, $R^{5'}$, $R^8$, $R^9$, $R^{10}$ or $R^{11}$ may be -L-$R_x$, where $R_x$ may be a moiety that links to an engineered glutamine-tags on a target-binding agent. In some embodiments, when wherein $R_x$ is a moiety that links to an engineered glutamine-tags on a target-binding agent, $R_x$ links to positions Q295 and/or N297Q of an Fc portion of an antibody (EU Kabat numbering) via transglutaminase-mediated conjugation.

In other embodiments, one of $R^b$, $R^5$, $R^{5'}$, $R^8$, $R^9$, $R^{10}$ or $R^{11}$ may be -L-$R_x$, where $R_x$ may be a moiety that links to an aldehyde-tags generated by formylglycine enzyme mediated conversion of cysteine to formylglycine followed by hydrazino-PICTET-Spengler (HIP) reaction.

In various embodiments, the compound of formula I or II may have a substituent -L-$S_c$, which is a conjugate covalently linked to a target-binding agent. In some embodiments, the target-binding agent may be a protein. For example, a compound having formula (I) or (II) can comprise a substituent -L-$S_c$ at an indicated location, wherein $S_c$ is a target-binding agent.

In some embodiments, when the target-binding agent is a protein, then the protein may be an antibody. In some embodiments, when the target-binding agent is a protein, then the protein may be an antibody fragment. In other embodiments, when the target-binding agent is a protein, then the protein may be an antibody single-chain fragment variable ("scFV").

In some embodiments, when the compound of formula I or II is a conjugate having -L-$S_c$, the target-binding agent may bind to a tumor-associated antigen, a cancer-stem-cell associated antigen or a viral antigen.

In other embodiments, when the compound of formula I or II is a conjugate having -L-$S_c$, the target-binding agent may bind to a target selected from an acute myeloid leukemia (AML M4) cell, an acute promyelocytic leukemia cell, an acute lymphoblastic leukemia cell, an acute lymphocytic leukemia cell, a chronic lymphocytic leukemia cell, a chronic myeloid leukemia cell, a chronic T-cell lymphocytic leukemia, a myelodysplastic syndromic cell, a multiple myeloma cell, a prostate carcinoma cell, a renal cell adenocarcinoma cell, a pancreatic adenocarcinoma cell, a lung carcinoma cell or a gastric adenocarcinoma cell, a gastric adenocarcinoma cell, a breast cancer cell, a colon cancer cell, a melanoma cell, a thyroid cancer cell, an ovarian cancer cell, a bladder cancer cell, a liver cancer cell, a head & neck cancer cell, an esophageal cancer cell, a hodgkin lymphoma cell, a non-hodgkin lymphoma cell, a mesothelioma cell, a neuroblastoma cell, a neuroendocrine tumor cell, a neurofibromatosis type 1 (NF1) cell, a neurofibromatosis type 2 (NF2) or an osteosarcoma cell.

In other embodiments, when the compound of formula I or II is a conjugate having -L-S$_c$, the target-binding agent may bind a target selected from GPR114, CLL-1, IL1RAP, TIM-3, CD19, CD20, CD22, ROR1, mesothelin, CD33, CD123/IL3Ra, c-Met, PSMA, prostatic acid phosphatase (PAP), CEA, CA-125, Muc-1, AFP, Glycolipid F77, EGFRvIII, GD-2, NY-ESO-1 TCR, tyrosinase, TRPI/gp75, gp100/pmeI-17, Melan-A/MART-1, Her2/neu, WT1, EphA3, telomerase, HPV E6, HPV E7, EBNA1, BAGE, GAGE and MAGE A3 TCRSLITRK6, ENPP3, Nectin-4, CD27, SLC44A4, CAIX, Cripto, CD30, MUC16, GPNMB, BCMA, Trop-2, Tissue Factor (TF), CanAg, EGFR, αv-integrin, CD37, Folate Receptor, CD138, CEACAM5, CD56, CD70, CD74, GCC, 5T4, CD79b, Steap1, Napi2b, Lewis Y Antigen, LIV c-RET, DLL3, EFNA4, Endosialin/CD248.

In other embodiments, when the compound of formula I or II is a conjugate having -L-S$_c$, the target-binding agent may be a bi-specific antibody/antibody fragment. In some embodiments, when the target-binding agent is a bi-specific antibody/antibody fragment, the bi-specific antibody/antibody fragment may bind to one or two targets selected from GPR114, CLL-1, IL1RAP, TIM-3, CD19, CD20, CD22, ROR1, mesothelin, CD33, CD123/IL3Ra, c-Met, PSMA, prostatic acid phosphatase (PAP), CEA, CA-125, Muc-1, AFP, Glycolipid F77, EGFRvIII, GD-2, NY-ESO-1 TCR, tyrosinase, TRPI/gp75, gp100/pmeI-17, Melan-A/MART-1, Her2/neu, WT1, EphA3, telomerase, HPV E6, HPV E7, EBNA1, BAGE, GAGE and MAGE A3 TCRSLITRK6, ENPP3, Nectin-4, CD27, SLC44A4, CAIX, Cripto, CD30, MUC16, GPNMB, BCMA, Trop-2, Tissue Factor (TF), CanAg, EGFR, αv-integrin, CD37, Folate Receptor, CD138, CEACAM5, CD56, CD70, CD74, GCC, 5T4, CD79b, Steap1, Napi2b, Lewis Y Antigen, LIV, c-RET, DLL3, EFNA4, Endosialin/CD248. In another embodiment the target-binding agent is a humanized antibody/antibody fragment. In another embodiment the target-binding antibody/antibody fragment is modified to contain a non-natural cysteine residue. In another embodiment the compound of Formula I or II is attached to the target binding antibody/antibody fragment at the non-natural cysteine residue.

In another aspect this disclosure provides an antibody-drug conjugate comprising an antibody/antibody fragment that binds specifically to cancerous myeloproliferative cells and/or leukemic cancer stem cells and does not bind to normal hematopoietic stem cells. In one embodiment the antibody/antibody fragment is humanized. In another embodiment the antibody/antibody fragment is modified to introduce a non-natural cysteine residue. In another embodiment the drug is conjugated to the non-natural cysteine residue. In another embodiment the drug is the compound having a structure of Formula (I) or (II) herein. In another embodiment the number of drug molecules conjugated per antibody/antibody fragment is in the range from about 1 to about 10. In another embodiment the number of drug molecules conjugated per antibody/antibody fragment is in the range from about 1 to about 3.

An antibody-drug conjugate having a structure of Formula III:

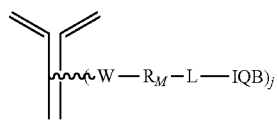

wherein:

is an antibody or antibody fragment;

W—R$_M$ is a linking moiety formed by W and R$_x$, wherein W is a moiety attached to a natural or unnatural amino acid residue of the antibody/antibody fragment and R$_x$ is a reactive moiety linking L-IQB to the antibody; L is a linker, wherein L is a bond or is a moiety having 1-200 nonhydrogen atoms selected from C, N, O, S, or halogen, and optionally incorporates ether, oxo, carboxamidyl, urethanyl, branched, cyclic, unsaturated, heterocyclic, aromatic or heteroaromatic moieties; j is a number of 1 to 10; and, IQB is a compound having a structure of Formula (I) or (II):

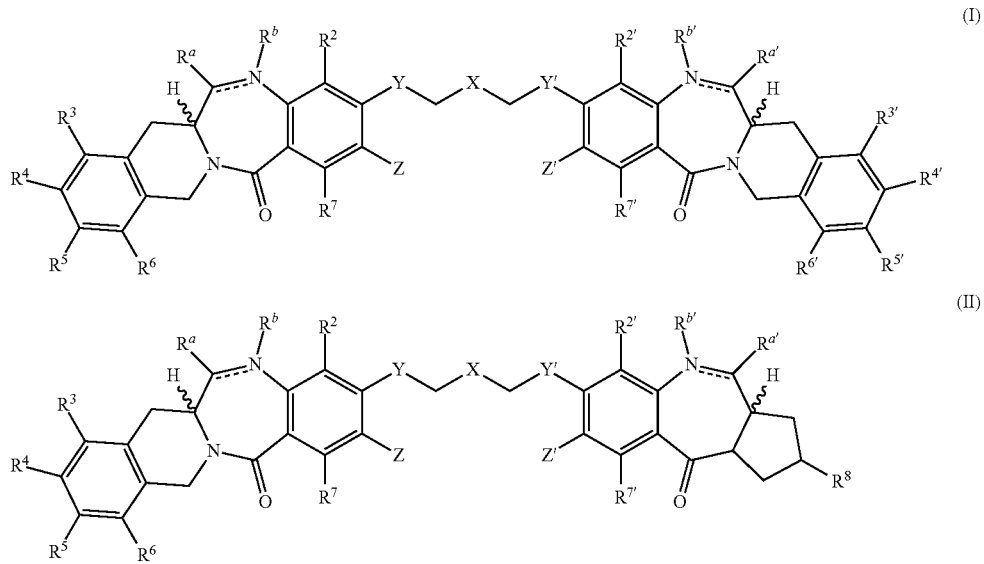

wherein: the dotted bond shown between —C($R^a$)— and —N($R^b$)— or —C($R^{a'}$)— and —N($R^{b'}$)— is independently a single bond or a double bond; when a double bond is present between —C($R^a$)— and —N($R^b$)—, the —C($R^a$)— is olefinic and has a substituent $R^a$ and Rb of the —N($R^b$)— is not present; when a single bond is present between —C($R^a$)— and —N(Rb)—, the —C($R^a$)— is saturated and has a hydrogen substituent in addition to the Ra substituent and $R^b$ of the —N($R^b$)— is present; when a double bond is present between —C(Ra')— and —N($R^{b'}$)—, the —C($R^{a'}$)— is olefinic and has a substituent $R^{a'}$ and $R^{b'}$ of the —N($R^{b'}$)— is not present; when a single bond is present between —C($R^{a'}$)— and —N($R^{b'}$)—, the —C($R^{a'}$)— is saturated and has a hydrogen substituent in addition to the $R^{a'}$ substituent and $R^{b'}$ of the —N($R^{b'}$)— is present; each of $R^a$ and $R^{a'}$ is independently H, OH, or —O—P, where P is a protecting group; if present, each of $R^b$ and $R^{b'}$ is independently H, or -L; $R^2$, $R^{2'}$, $R^3$, $R^{3'}$, $R^4$, $R^{4'}$, $R^{6'}$ and $R^6$ are each independently selected from H, OH, $C_1$-$C_{10}$ alkyl, $C_2$-$C_{10}$ alkenyl or $C_2$-$C_{10}$ alkynyl; each of $R^5$ or $R^{5'}$ is independently $NH_2$, $CO_2H$, H, OH $C_1$-$C_{10}$ alkyl, $C_2$-$C_{10}$ alkenyl, $C_2$-$C_{10}$ alkynyl, -L; each of $R^7$ and $R^{7'}$ is H; $R^8$ is: H, $NH_2$, $CO_2H$, or -L, wherein the carbon to which $R^8$ is attached also has a hydrogen substituent; or an exo olefin having the structure

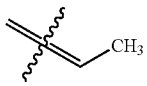

wherein the carbon to which $R^8$ is attached has no other substituent; X is: $C_{1-12}$ alkylene, optionally wherein the alkylene chain is interrupted by one or more hetero atoms selected from the group consisting of O, S, and NH; or —$(CH_2)_m$-Q-$(CH_2)_p$—, wherein m and p are each independently 0, 1 or 2; Q has a structure of formula:

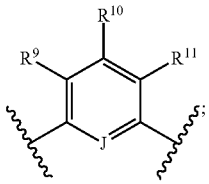

wherein each of $R^9$, $R^{10}$ and $R^{11}$ is H, $NH_2$, $CO_2H$, -L; and J is CH or N; each of Y and Y' is independently O, S, or NH; each of Z and Z' is independently H, R, OH, OR, SH, SR, $NH_2$, or NHR, where each R is independently unsubstituted $C_1$-$C_{12}$ alkyl, substituted $C_1$-$C_{12}$ alkyl, unsubstituted $C_3$-$C_{20}$ heterocyclyl, substituted $C_3$-$C_{20}$ heterocyclyl, unsubstituted $C_6$-$C_{20}$ aryl groups, and unsubstituted $C_6$-$C_{20}$ aryl groups; and wherein only one of $R^b$, $R^{b'}$, $R^5$, $R^{5'}$, $R^8$, $R^9$, $R^{10}$, and $R^{11}$ is -L.

An antibody-drug conjugate having a structure of Formula III:

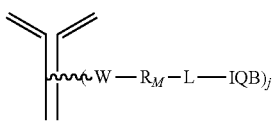

wherein:

is an antibody or antibody fragment;

W—$R_M$ is a linking moiety formed by W and $R_x$, wherein W is a moiety attached to a natural or unnatural amino acid residue of the antibody/antibody fragment and $R_x$ is a succinimidyl, maleimidyl, cylooctynyl, aminooxy, bisulfonyl, sulfonyl, or isothiocyanate moiety, such that W—$R_M$ is a disulfide, a thiolated succinimidyl, an amino substituted succinimidyl, a (cyclooctyl)-1, 4 triazolyl, oxime substituted N-glycan, oxime, a substituted bis-sulfopropyl, a sulfonamidyl, an amide, or a thiocarbamate moiety; L is a linker, wherein L is a bond or is a moiety having 1-200 nonhydrogen atoms selected from C, N, O, S, or halogen, and optionally incorporates ether, oxo, carboxamidyl, urethanyl, branched, cyclic, unsaturated, heterocyclic, aromatic or heteroaromatic moieties; j is a number of 1 to 10; and, IQB is a compound having a structure of Formula (I) or (II):

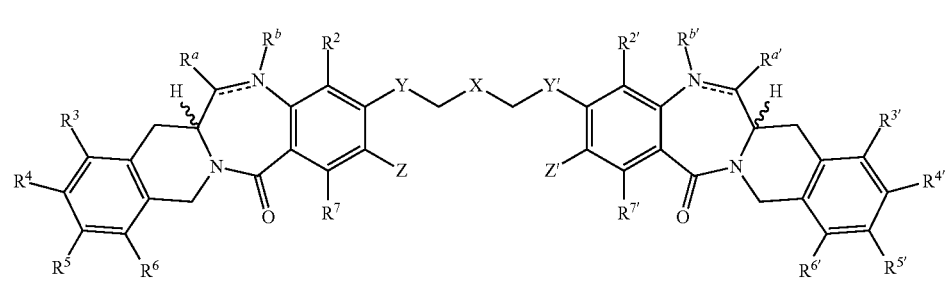

(I)

-continued

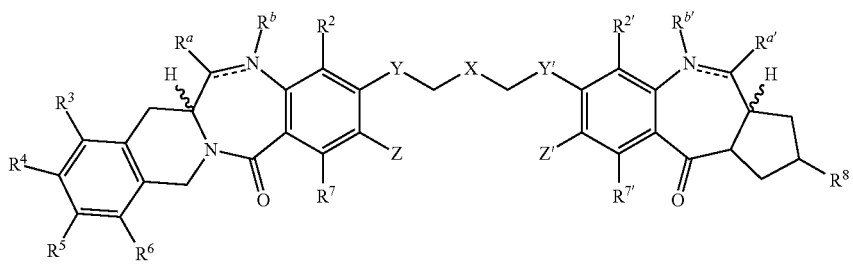

(II)

wherein: the dotted bond shown between —C($R^a$)— and —N($R^b$)— or —C($R^{a'}$)— and —N($R^{b'}$)— is independently a single bond or a double bond; each of $R^a$ and $R^{a'}$ is independently H, OH, or —O—P, where P is a protecting group; if present, each of $R^b$ and $R^{b'}$ is independently H, or a bond linked to linker L; $R^2$, $R^{2'}$, $R^3$, $R^{3'}$, $R^4$, $R^{4'}$, $R^6$' and $R^6$ are each independently selected from H, OH, $C_1$-$C_{10}$ alkyl, $C_2$-$C_{10}$ alkenyl or $C_2$-$C_{10}$ alkynyl; each of $R^5$ or $R^{5'}$ is independently $NH_2$, $CO_2H$, H, OH $C_1$-$C_{10}$ alkyl, $C_2$-$C_{10}$ alkenyl, $C_2$-$C_{10}$ alkynyl, a bond linked to linker L; each of $R^7$ and $R^{7'}$ is H; $R^8$ is: H, $NH_2$, $CO_2H$, or a bond linked to linker L, wherein the carbon to which $R^8$ is attached also has a hydrogen substituent; or an exo olefin having the structure

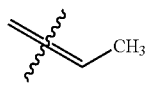 [SMILES: *=CC]

wherein the carbon to which $R^8$ is attached has no other substituent; X is: $C_{1-12}$ alkylene, optionally wherein the alkylene chain is interrupted by one or more hetero atoms selected from the group consisting of O, S, and NH; or —$(CH_2)_m$-Q-$(CH_2)_p$—, wherein m and p are each independently 0, 1 or 2; Q has a structure of formula:

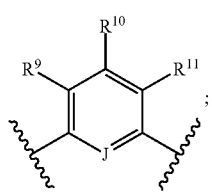

wherein each of $R^9$, $R^{10}$ and $R^{11}$ is H, $NH_2$, $CO_2H$, a bond linked to linker L; and J is CH or N; each of Y and Y' is independently O, S, or NH; each of Z and Z' is independently H, R, OH, OR, SH, SR, $NH_2$, or NHR, where each R is independently unsubstituted $C_1$-$C_{12}$ alkyl, substituted $C_1$-$C_{12}$ alkyl, unsubstituted $C_3$-$C_{20}$ heterocyclyl, substituted $C_3$-$C_{20}$ heterocyclyl, unsubstituted $C_6$-$C_{20}$ aryl groups, and unsubstituted $C_6$-$C_{20}$ aryl groups; and wherein only one of $R^b$, $R^{b'}$, $R^5$, $R^{5'}$, $R^8$, $R^9$, $R^{10}$, and $R^{11}$ is a bond linked to linker L.

In one embodiment of an antibody-drug conjugate, W is attached directly or indirectly to the amino acid residue of the antibody/antibody fragment. In another embodiment $R_x$ is a succinimidyl, maleimidyl, cylooctynyl, aminooxy, bisulfonyl, sulfonyl, or isothiocyanate moiety. In another embodiment W—$R_M$ is a disulfide, a thiolated succinimidyl, an amino substituted succinimidyl, a (cyclooctyl)-1, 4 triazolyl, oxime substituted N-glycan, oxime, a substituted bis-sulfopropyl, a sulfonamidyl, an amide, or a thiocarbamate moiety. In another embodiment —W—$R_M$-L-IQB is a moiety having a structure of Formula IV:

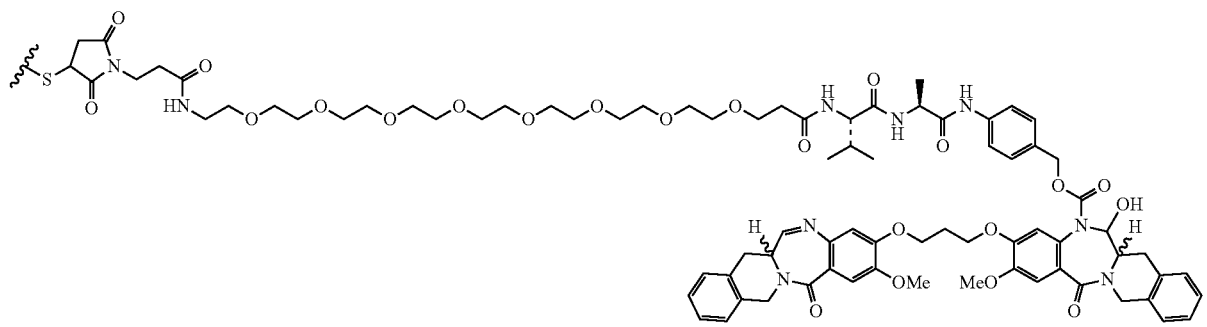 [SMILES: *SC1CC(=O)N(CCC(=O)NCCOCCOCCOCCOCCOCCOCCOCCOCCC(=O)N[C@H](C(=O)N[C@@H](C)C(=O)Nc2ccc(COC(=O)N3c4cc(OCCCOc5cc6c(cc5OC)C(=O)N5Cc7ccccc7CC5C=N6)c(OC)cc4C(=O)N4Cc5ccccc5CC4C3O)cc2)C(C)C)C1=O]

In another embodiment the antibody/antibody fragment is humanized. In another embodiment the antibody/antibody fragment is modified to introduce a non-natural cysteine residue. In another embodiment the drug is conjugated to the non-natural cysteine residue. j is 1 to 3.

In another aspect, a pharmaceutical composition is provided including the compound of formula I or II:

where the carbon to which $R^8$ is attached has no other substituent.

X is $C_{1-12}$ alkylene, optionally where the alkylene chain is interrupted by one or more hetero atoms selected from the group consisting of O, S, and NH; or —(CH$_2$)$_m$-Q-(CH$_2$)$_p$—, wherein m and p are each independently 0, 1 or 2.

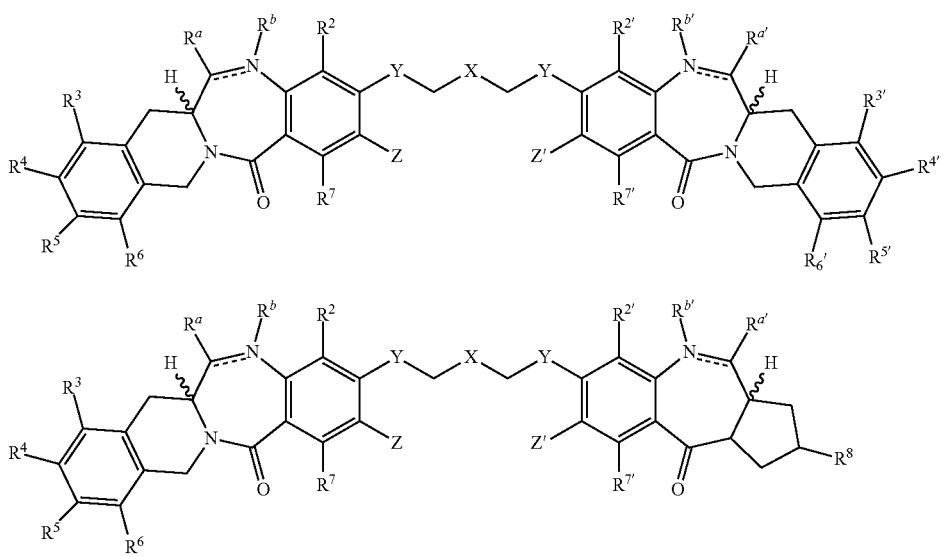

Formula I

Formula II where the dotted bond shown between —C($R^a$)— and —N($R^b$)— or —C($R^{a'}$)— and —N($R^{b'}$)— is independently a single bond or a double bond. When a double bond is present between —C($R^a$)— and —N($R^b$)—, the —C($R^a$)— is olefinic and has a substituent $R^a$ and $R^b$ of the —N($R^b$)— is not present. When a single bond is present between —C($R^a$)— and —N(Rb)—, the —C($R^a$)— is saturated and has a hydrogen substituent in addition to the $R^a$ substituent and $R^b$ of the —N($R^b$)— is present. When a double bond is present between —C($R^{a'}$)— and —N($R^{b'}$)—, the —C($R^{a'}$)— is olefinic and has a substituent $R^{a'}$ and $R^{b'}$ of the —N($R^{b'}$)— is not present. When a single bond is present between —C($R^{a'}$)— and —N($R^{b'}$)—, the —C($R^{a'}$)— is saturated and has a hydrogen substituent in addition to the $R^{a'}$ substituent and $R^{b'}$ of the —N($R^{b'}$)— is present.

Each of $R^a$ and $R^{a'}$ is independently H, OH, or —O—P, where P is a protecting group. If present, each of $R^b$ and $R^{b'}$ is independently H, L-R$_x$ or L-S$_c$; $R^2$, $R^{2'}$, $R^3$, $R^{3'}$, $R^4$, $R^{4'}$ $R^{6'}$ and $R^6$ are each independently selected from H, OH, $C_1$-$C_{10}$ alkyl, $C_2$-$C_{10}$ alkenyl or $C_2$-$C_{10}$ alkynyl; and each of $R^5$ or $R^{5'}$ is independently NH$_2$, CO$_2$H, H, OH $C_1$-$C_{10}$ alkyl, $C_2$-$C_{10}$ alkenyl, $C_2$-$C_{10}$ alkynyl, -L-R$_x$ or -L-S$_c$; each of $R^7$ and $R^{7'}$ is H.

$R^8$ is H, NH$_2$, CO$_2$H, -L-R$_x$, or -L-S$_c$, where the carbon to which $R^8$ is attached also has a hydrogen substituent; or $R^8$ is an exo olefin having the structure

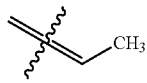 [SMILES: *=CC]

Q has a structure of formula:

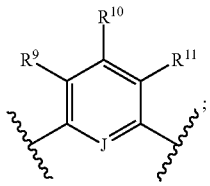

where each of $R^9$, $R^{10}$ and $R^{11}$ is H, NH$_2$, CO$_2$H, -L-R$_x$ or -L-S$_c$; and J is CH or N.

Each of Y and Y' is independently O, S, or NH; and each of Z and Z' is independently H, R, OH, OR, SH, SR, NH$_2$, or NHR, where each R is independently unsubstituted $C_1$-$C_{12}$ alkyl, substituted $C_1$-$C_{12}$ alkyl, unsubstituted $C_3$-$C_{20}$ heterocyclyl, substituted $C_3$-$C_{20}$ heterocyclyl, unsubstituted $C_6$-$C_{20}$ aryl groups, and unsubstituted $C_6$-$C_{20}$ aryl groups.

-L-R$_x$ is a linker L attached to a reactive moiety Rx, and -L-S$_c$ is a linker L attached to a substance S$_c$; where L is a bond or is a moiety having 1-200 nonhydrogen atoms selected from C, N, O, S, or halogen, and optionally incorporates ether, oxo, carboxamidyl, urethanyl, branched, cyclic, unsaturated, heterocyclic, aromatic or heteroaromatic moieties; R$_x$ is a reactive moiety; S$_c$ is a target binding agent selected from a protein, a portion of a protein, a peptide or a nucleic acid; and when -L-R$_x$ or -L-S$_c$ is present in the compound of formula I or II, only one of $R^b$, $R^{b'}$, $R^5$, $R^{5'}$, $R^8$, $R^9$, $R^{10}$, and $R^{11}$ is L-R$_x$ or -L-S$_c$.

In yet another aspect, a pharmaceutical composition is provided including the compound of formula I or II as described herein, where the compound has a substituent -L-S$_c$, which is a conjugate of this disclosure covalently linked to a target-binding agent.

In a further aspect, a use is provided for a compound of formula I or II as described herein, or for the conjugate of this disclosure including a compound of formula I or II, having a substituent -L-$S_c$ as described herein, in the manufacture of a medicament.

In another aspect, provided herein is a method of treating cancer comprising contacting cancer cells administering to a subject with the cancer a therapeutically effective amount of a compound of formula (I) of (II) as provided herein, or a conjugate thereof as provided herein. In one embodiment the cancer treated is a leukemia, lymphoma or a solid tumor. In another embodiment the conjugate comprises an antibody that specifically binds a tumor-associated antigen or a cancer-stem-cell associated antigen.

In another aspect, provided herein is a method of inhibiting cell division comprising contacting a cell with a compound of formula (I) of (II) as provided herein, or a conjugate thereof as provided herein.

Other objects of the disclosure may be apparent to one skilled in the art upon reading the following specification and claims.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1 shows the generic Formula I and generic Formula II.

FIG. 10 shows cytotoxicity on Leukemia Cell lines of various IQB Payloads.

FIG. 11 shows cytotoxicity of IQB Payloads on Lymphoma Cell line CA46.

FIG. 12 shows $GI_{50}$ values (pg/mL) on Leukemia and Lymphoma Cell lines of various IQB Payloads.

FIG. 13 shows cytotoxicity on solid tumor cell lines of various IQB Payloads.

FIG. 14 shows cytotoxicity on solid tumor cell lines of various IQB Payloads.

FIG. 15 shows cytotoxicity on solid tumor cell lines of various IQB Payloads.

FIG. 16 shows cytotoxicity on solid tumor cell lines of various IQB Payloads.

FIG. 17 shows cytotoxicity on solid tumor cell lines of various IQB Payloads.

FIG. 18 shows a summary of $GI_{50}$ values (pg/mL) on Solid Tumor Cell lines.

FIGS. 20A, 20B, 20C and 20D show a synthesis scheme for CLT-D202.

FIGS. 24A and 24B show that a CLL1-ADC kills both quiescent and proliferating cells.

FIG. 26 shows that a CLL1-ADC inhibits colony formation of primary AML patient cancer cells.

DETAILED DESCRIPTION OF THE INVENTION

Figure 2:
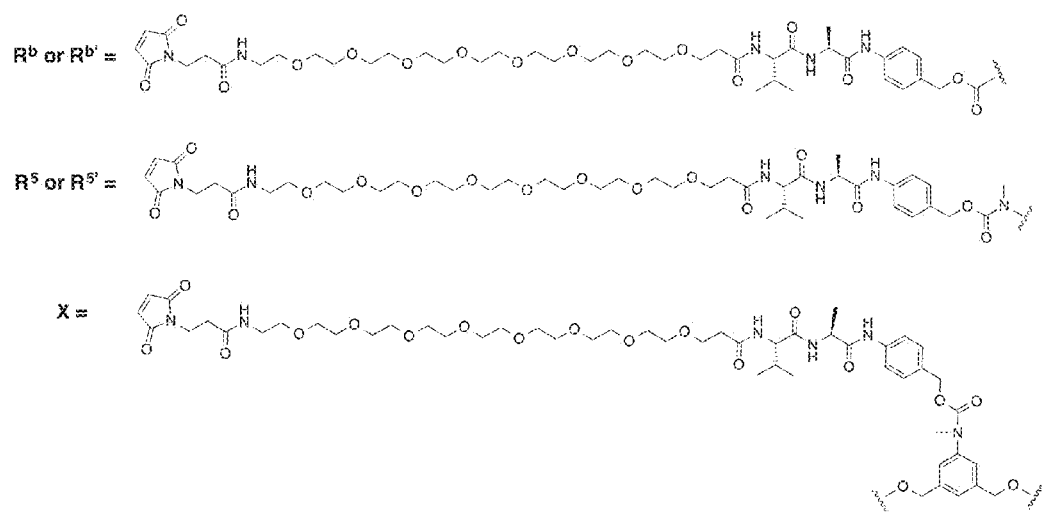
FIG. 2 shows linker moieties $R^b$, $R^{b'}$, $R^5$, $R^{5'}$ and X.

This application is not limited to particular methodologies or the specific compositions described, as such may, vary. It is also to be understood that the terminology used herein is for the purpose of describing particular embodiments only, and is not intended to be limiting, since the scope of the present application will be limited only by the appended claims and their equivalents.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present application, the preferred methods and materials are now described.

I. Isoquinolidinobenzodiazepines

Isoquinolidinobenzodiazepines ("IQBs") are encompassed by generic formulae disclosed herein. The compounds may be identified either by their chemical structure and/or chemical name. When the chemical structure and chemical name conflict, the chemical structure is determinative of the identity of the compound. The compounds may contain one or more chiral centers and/or double bonds and therefore, may exist as stereoisomers, such as double-bond isomers (i.e., geometric isomers), enantiomers or diastereomers. Accordingly, when stereochemistry at chiral centers is not specified, the chemical structures depicted herein encompass all possible configurations at those chiral centers including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds.

Isoquinolidinobenzodiazepines may exist in unsolvated forms as well as solvated forms, including hydrated forms and as N-oxides. In general, the hydrated, solvated and N-oxide forms are within the scope of the present disclosure. Certain compounds may exist in multiple crystalline or amorphous forms. In general, all physical forms are equivalent for the uses contemplated herein and are intended to be within the scope of the present disclosure. Further, it should be understood, when partial structures of the compounds are illustrated, that brackets indicate the point of attachment of the partial structure to the rest of the molecule.

As referred to herein, "alkyl" means a saturated, branched or straight-chain or cyclic, monovalent hydrocarbon radical having the stated number of carbon atoms (i.e., C1-C6 means one to six carbon atoms) that is derived by the removal of one hydrogen atom from a single carbon atom of a parent alkane. Typical alkyl groups include, but are not limited to, methyl; ethyl; propyls such as propan-1-yl, propan-2-yl, cyclopropan-1-yl; butyls such as butan-1-yl, butan-2-yl, 2-methyl-propan-1-yl, 2-methyl-propan-2-yl, cyclobutan-1-yl; and the like. In some embodiments, "alkyl" means a saturated, branched or straight-chain, monovalent hydrocarbon radical having the stated number of carbon atoms (i.e., C1-C6 means one to six carbon atoms) that is derived by the removal of one hydrogen atom from a single carbon atom of a parent alkane. Typical alkyl groups include, but are not limited to, methyl; ethyl; propyls such as propan-1-yl, propan-2-yl; butyls such as butan-1-yl, butan-2-yl, 2-methyl-propan-1-yl, 2-methyl-propan-2-yl; and the like.

As referred to herein, "alkenyl" means an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. As used herein, "lower alkenyl" means (C2-C8) alkenyl. In some embodiments, "alkenyl" means an unsaturated branched, straight-chain alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, etc.; and the like. As used herein, "lower alkenyl" means (C2-C8) alkenyl.

As referred to herein, "alkynyl" means an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. As used herein, "lower alkynyl" means (C2-C8) alkynyl. In some embodiments, "alkynyl" means an unsaturated branched, straight-chain alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. As used herein, "lower alkynyl" means (C2-C8) alkynyl.

Cyclic alkyl, alkenyl and alkynyl groups are also defined by the term "cycloalkyl" which means a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted.

As referred to herein, "alkylene" means a divalent alkyl moiety.

As referred to herein, "alkoxy" means an alkyl group having an oxygen atom that connects the alkyl group to the point of attachment: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

As referred to herein, "halide" means fluoro, chloro, bromo, or iodo.

As referred to herein, "carboxamide" means a monovalent moiety having the formula —C(=O)NH$_2$. In some embodiments, one or both of the amide hydrogens may be replaced by substituents other than hydrogen.

As referred to herein "carboxamidyl" means a divalent moiety having the formula —C(=O)N(H)—. In some embodiments the amide hydrogen may be replaced by other substituents.

As referred to herein, "oxo" means a moiety having a formula

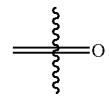 [SMILES: *=O]

which is attached to a carbon.

As referred to herein, "carboxyl" means a moiety having a formula —C(O)OH or —C(O)O$^-$.

As referred to herein, "heteroalkyl" means an alkyl group of any suitable length and having from 1 to 3 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heteroalkyl can include ethers, thioethers and alkyl-amines. The heteroatom portion of the heteroalkyl can replace a hydrogen of the alkyl group to form a hydroxy, thio or amino group. Alternatively, the heteroartom portion can be the connecting atom, or be inserted between two carbon atoms.

As referred to herein, "heterocyclic" or "heterocyclyl" means a moiety that is a saturated or unsaturated, mono or multicyclic alkyl cyclic moiety having heteroatom substitution replacing ring carbons. Multicyclic heterocyclic moieties may have fused rings. Typical heterocyclic groups include, but are not limited to, tetrahydrofuranyl (e.g., tetrahydrofuran-2-yl, tetrahydrofuran-3-yl, etc.), piperidinyl (e.g., piperidin-1-yl, piperidin-2-yl, etc.), morpholinyl (e.g., morpholin-3-yl, morpholin-4-yl, etc.), piperazinyl (e.g., piperazin-1-yl, piperazin-2-yl, etc.), and the like.

As referred to herein, "aromatic" or "aryl" means a monovalent aromatic hydrocarbon group having the stated number of carbon atoms (i.e., C6-C14 means from 6 to 14 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. Specific exemplary aryls include phenyl and naphthyl.

As referred to herein, "heteroaromatic" or "heteroaryl" means a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can also be oxidized, such as, but not limited to, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

As referred to herein, "$C_1$-$C_{12}$" means the range of number of carbon atoms included in the group described. For example a $C_1$-$C_{12}$ alkyl has from one carbon to 12 carbon atoms, and may be any one of 1, 2, 3, 4, 5, 6, 7, 8, 9, 10, 11, or 12 carbons. A $C_1$ alkyl is methyl, a $C_2$ alkyl is ethyl and so on. References to $C_1$-$C_{10}$ means one to ten carbons, $C_1$-$C_3$ means one to three carbons, and etc.

As referred to herein, "substituted" means a moiety having a hydrogen radical removed, and another non-hydrogen substituent replacing it. More than one substituent may be incorporated in any moiety, as long as the rule of chemical valency is observed. Substituents suitable for use in alkyl, alkenyl, alkynyl, aromatic or heterocyclic groups include —OH, —OR, —NH$_2$, —NHR, —NR$_2$, —CO$_2$H, —CO$_2$R, —C(O)NH$_2$, —C(O)NHR, —C(O)NR$_2$, halide, oxo, and R, where R is a $C_1$-$C_6$ alkyl.

As referred to herein, the term "nucleic acid", refers to a linear polymer of nucleosides (including deoxyribonucleosides, ribonucleosides, or analogs thereof) joined by inter-nucleosidic linkages. Nucleic acid may encompass the term "polynucleotide" as well as "oligonucleotide". The linear polymer may be represented by a sequence of letters, such as "ATGCCTG," where it will be understood that the nucleotides are in 5' to 3' order from left to right and that "A" denotes deoxyadenosine, "C" denotes deoxycytidine, "G" denotes deoxyguanosine, and "T" denotes deoxythymidine, unless otherwise noted. Another natural nucleotide is "U", denoting uridine. The letters A, C, G, T and U can be used to refer to the bases themselves, to nucleosides, or to nucleotides comprising the bases, as is standard in the art. In naturally occurring nucleic acids, the inter-nucleoside linkage is typically a phosphodiester bond, and the subunits are referred to as "nucleotides." Nucleic acids may also include other inter-nucleoside linkages, such as phosphorothioate linkages, and the like. Such analogs of nucleotides that do not include a phosphate group are considered to fall within the scope of the term "nucleotide" as used herein, and nucleic acids comprising one or more inter-nucleoside linkages that are not phosphodiester linkages are still referred to as "polynucleotides", "oligonucleotides", etc.

The term "amino acid" refers to both the twenty "canonical" or "natural" amino acids, as well "non-canonical" amino acids, also referred to as "unnatural" amino acids, such as modified or synthetic amino acids, as well as amino acid analogs and amino acid mimetics that function similarly to naturally occurring amino acids. Naturally occurring amino acids are those encoded by the genetic code. Modified amino acids include, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Specific Description of Chemical Nature of Cytotoxic Compounds

Provided here is a compound is having a structure of Formula (I) or (II):

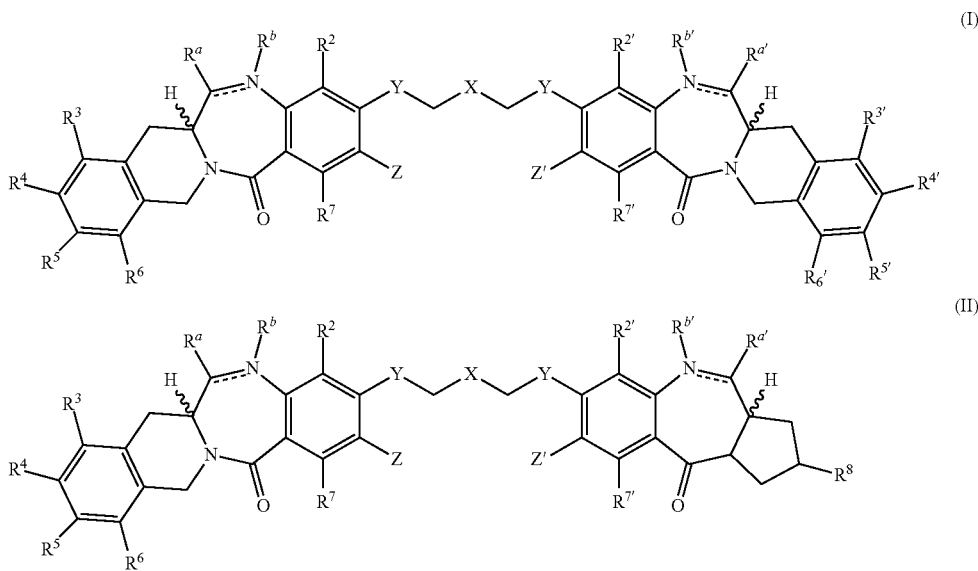

(I)

(II)

wherein the dotted bond between —C(R$^a$)— and —N(R$^b$)— or —C(R$^{a'}$)— and —N(R$^{b'}$)— is independently selected from a single bond or a double bond; when a double bond is present between —C(R$^a$)— and —N(R$^b$)—, the ring carbon —C(R$^a$)— is olefinic and has a substituent R$^a$ and the exocyclic R$^b$ of the —N(R$^b$)— is not present; when a single bond is present between —C(R$^a$)— and —N(R$^b$)—, the ring carbon —C(R$^a$)— is saturated and has a hydrogen exocyclic substituent in addition to the R$^a$ substituent and R$^b$ of the —N(R$^b$)— is present; and/or when a double bond is present between —C(R$^{a'}$)— and —N(R$^{b'}$)—, the ring carbon —C(R$^{a'}$)— is olefinic and has a substituent R$^{a'}$ and R$^{b'}$ of the —N(R$^{b'}$)— is not present; when a single bond is present between —C(R$^{a'}$)— and —N(R$^{b'}$)—, the -ring carbon C(R$^{a'}$)— is saturated and has a hydrogen substituent in addition to the R$^{a'}$ substituent and R$^{b'}$ of the —N(R$^{b'}$)— is present;

each of R$^a$ and R$^{a'}$ is independently H, OH, or —O—P, where P is a protecting group;

if either or both of R$^b$ or R$^{b'}$ is present, each of R$^b$ and R$^{b'}$ is independently H, L-R$_x$ or L-S$_c$;

R$^2$, R$^{2'}$, R$^3$, R$^{3'}$, R$^4$, R$^{4'}$, R$^6$ and R$^{6'}$ are each independently selected from H, OH, C$_1$-C$_{10}$ alkyl, C$_2$-C$_{10}$ alkenyl or C$_2$-C$_{10}$ alkynyl;

each of R$^5$ or R$^{5'}$ is independently NH$_2$, CO$_2$H, H, OH, C$_1$-C$_{10}$ alkyl, C$_1$-C$_{10}$ alkenyl or C$_1$-C$_{10}$ alkynyl, -L-R$_x$ or -L-S$_c$;

each of R$^7$ and R$^{7'}$ is H;

R$^8$ is H, NH$_2$, CO$_2$H, -L-R$_x$, or -L-S$_c$, wherein the carbon to which R$^8$ is attached also has a hydrogen substituent; or R$^8$ is an exo olefin having the structure

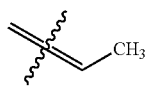

wherein the ring carbon to which R$^8$ is attached is olefinic and has no other exocyclic substituent;

X is C$_{1-12}$ alkylene, optionally wherein the alkylene chain is interrupted by one or more hetero atoms selected from the group consisting of O, S, and NH; or X is —(CH$_2$)$_m$-Q-(CH$_2$)$_p$—, wherein m and p are each independently 0, 1 or 2;

Q has a structure of formula:

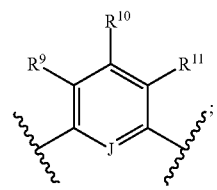

wherein each of R$^9$, R$^{10}$ and R$^{11}$ is H, NH$_2$, CO$_2$H, -L-R$_x$ or -L-S$_c$; and J is CH or N;

each of Y and Y' is independently O, S, or NH;

each of Z and Z' is independently H, R, OH, OR, SH, SR, NH$_2$, or NHR, where each R is independently unsubstituted C$_1$-C$_{12}$ alkyl, substituted C$_1$-C$_{12}$ alkyl, unsubstituted C$_3$-C$_{20}$ heterocyclyl, substituted C$_3$-C$_{20}$ heterocyclyl, unsubstituted C$_5$-C$_{20}$ aryl groups, and unsubstituted C$_5$-C$_{20}$ aryl groups;

-L-R$_x$ is a linker L attached to a reactive moiety R$_x$;

-L-S$_c$ is a linker L attached to a substance S$_c$;

L is a bond or is a moiety having 1-200 nonhydrogen atoms selected from C, N, O, S, or halogen, and optionally incorporates ether, oxo, carboxamidyl, urethanyl, branched, cyclic, unsaturated, heterocyclic, aromatic or heteroaromatic moieties;

R$_x$ is a reactive moiety;

S$_c$ is a target binding agent selected from a protein, a portion of a protein, or a peptide; and when -L-R$_x$ or -L-S$_c$ is present in the compound of formula I or II, only one of R$^b$, R$^{b'}$, R$^5$, R$^{5'}$, R$^8$, R$^9$, R$^{10}$, R$^{11}$ is L-R$_x$ or -L-S$_c$.

Also provided here is a compound of Formula I or II:

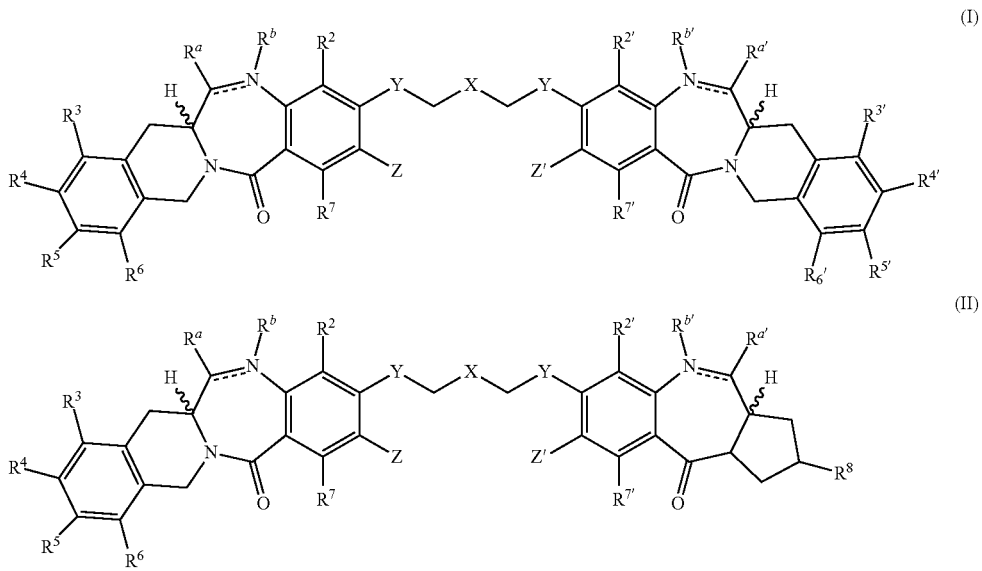

wherein: the dotted bond shown between —C($R^a$)— and —N($R^b$)— or —C($R^{a'}$)— and —N($R^{b'}$)— is independently a single bond or a double bond; each of $R^a$ and $R^{a'}$ is independently H, OH, or —O—P, where P is a protecting group; each of $R^b$ and $R^{b'}$ is not present or is independently H, or L-$R_x$;

$R^2$, $R^{2'}$, $R^3$, $R^{3'}$, $R^4$, $R^{4'}$, $R^{6'}$ and $R^6$ are each independently selected from H, OH, $C_1$-$C_{10}$ alkyl, $C_2$-$C_{10}$ alkenyl or $C_2$-$C_{10}$ alkynyl;

each of $R^5$ or $R^{5'}$ is independently $NH_2$, $CO_2H$, H, OH, $C_1$-$C_{10}$ alkyl, $C_2$-$C_{10}$ alkenyl, $C_2$-$C_{10}$ alkynyl, or -L-R;

each of $R^7$ and $R^{7'}$ is H;

$R^8$ is H, $NH_2$, $CO_2H$, or -L-$R_x$, wherein the carbon to which $R^8$ is attached also has a hydrogen substituent; or an exo olefin having the structure

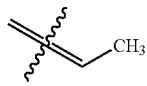

wherein the carbon to which $R^8$ is attached has no other substituent;

X is $C_{1-12}$ alkylene, optionally wherein the alkylene chain is interrupted by one or more hetero atoms selected from the group consisting of O, S, and NH; or —$(CH_2)_m$-Q-$(CH_2)_p$, wherein m and p are each independently 0, 1 or 2; Q has a structure of formula:

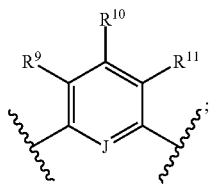

wherein each of $R^9$, $R^{10}$ and $R^{11}$ is H, $NH_2$, $CO_2H$, or -L-$R_x$; and J is CH or N;

each of Y and Y' is independently O, S, or NH;

each of Z and Z' is independently H, R, OH, OR, SH, SR, $NH_2$, or NHR, where each R is independently unsubstituted $C_1$-$C_{12}$ alkyl, substituted $C_1$-$C_{12}$ alkyl, unsubstituted $C_3$-$C_{20}$ heterocyclyl, substituted $C_3$-$C_{20}$ heterocyclyl, unsubstituted $C_6$-$C_{20}$ aryl groups, and unsubstituted $C_6$-$C_{20}$ aryl groups;

-L-$R_x$ is a linker L attached to a reactive moiety Rx;

wherein L is a bond or is a moiety having 1-200 nonhydrogen atoms selected from C, N, O, S, or halogen, and optionally incorporates ether, oxo, carboxamidyl, urethanyl, branched, cyclic, unsaturated, heterocyclic, aromatic or heteroaromatic moieties;

$R_x$ is a reactive moiety; and when -L-$R_x$ is present in the compound of formula I or II, only one of $R^b$, $R^{b'}$, $R^5$, $R^{5'}$, $R^8$, $R^9$, $R^{10}$, and $R^{11}$ is L-$R_x$.

The seven-membered lactam ring of the isoquinolidinobenzodiazepine moiety may have either a double bond or a single bond connecting —C($R^a$)— and —N($R^b$)— (left hand IQB), or equivalently —C($R^{a'}$)— and —N($R^{b'}$)— (right hand IQB). The compounds of formula I or II may independently be selected to have any combination of IQB moieties having either a single bond or a double bond in each IQB ring. In some embodiments, when a double bond is present between —C($R^a$)— and —N($R^b$)—, the ring carbon —C($R^a$)— is olefinic and has a substituent $R^a$ and the exocyclic $R^b$ of the —N($R^b$)— is not present. In embodiments when a single bond is present between —C($R^a$)— and —N($R^b$)—, the ring carbon —C($R^a$)— is saturated and has a hydrogen exocyclic substituent in addition to the $R^a$ substituent and $R^b$ of the —N($R^b$)— is present. Equivalently, a compound of formula I or II may have a double bond present between —C($R^{a'}$)— and —N($R^{b'}$)—, wherein then the ring carbon —C($R^{a'}$)— is olefinic and has a substituent $R^{a'}$ and $R^{b'}$ of the —N($R^{b'}$)— is not present. Alternatively, when a single bond is present between —C($R^{a'}$)— and —N($R^{b'}$)— for a compound of formula I or II, the ring carbon C(R$^{a'}$)— is saturated and has a hydrogen substituent in addition to the R$^{a'}$ substituent and R$^{b'}$ of the —N(R$^{b'}$)— is present. In some embodiments, the compound of formula I or II has a double bond connecting —C(R$^a$)— and —N(R$^b$) as well as a double bond connecting —C(R$^{a'}$)— and —N(R$^{b'}$)—, and neither R$^b$ or R$^{b'}$ are present. In other embodiments, the compound of formula I or II has a double bond connecting —C(R$^a$)— and —N(R$^b$) as and a single bond connecting —C(R$^{a'}$)— and —N(R$^{b'}$)—, resulting in a compound having a hydrogen substituent and R$^{a'}$ present on —C(R$^{a'}$)— and R$^{b'}$ present on —N(R$^{b'}$)—. In yet other embodiments, the compound of formula I or II has a single bond connecting —C(R$^a$)— and —N(R$^b$) and a double bond connecting —C(R$^{a'}$)— and —N(R$^{b'}$)—, resulting in a compound having a hydrogen substituent and R$^a$ present on —C(R$^a$)— and no R$^{b'}$ is present. Finally, a compound of Formula I or II may have a single bond connecting —C(R$^a$)— and —N(R$^b$) and a single bond connecting —C(R$^{a'}$)— and —N(R$^{b'}$), resulting in a compound having a hydrogen substituent as well as R$^a$ on ring carbon —C(R$^a$)—, a hydrogen substituent as well as R$^{a'}$ on ring carbon —C(R$^{a'}$)—, and R$^b$ and R$^{b'}$ are both present. An olefinic ring carbon is a ring carbon forming a double bond with one ring atom such as carbon or nitrogen, forming a single bond with another ring atom such as carbon or nitrogen, and forming a single bond with an exocyclic group such as R$^a$ or R$^{a'}$.

R$^a$ and R$^{a'}$ are independently H, OH, or —O—P, where P is a protecting group. Any suitable protecting group may be selected. In some embodiments, the protecting may be a silyl protecting group such as, but not limited to Trimethylsilyl (TMS), tributyldimethylsilyl (TBDMS, also referred to as TBS), or tributyldiphenylsilyl (TBDPS); a benzyl protecting group, methoxymethyl (MEM) or the like. A wide variety of protecting groups are known in the art and may be found for example in Greene's Protective Groups in Organic Synthesis, Fourth Edition, Wuts and Greene, John Wiley and Sons, Inc. 2006.

When R$^b$ or R$^{b'}$ is present, each of R$^b$ and R$^{b'}$ is independently H, L-R$_x$ or L-S$_c$, with the proviso that only one L-R$_x$ or L-S$_c$ may be present in the compound of formula I or II. The moieties -L-R$_x$ and L-S$_c$ are as defined below.

R$^2$, R$^{2'}$, R$^3$, R$^{3'}$, R$^4$, R$^{4'}$, R$^{6'}$ and R$^6$ are each independently selected from H, OH, C$_1$-C$_{10}$ alkyl, C$_1$-C$_{10}$ alkenyl or C$_1$-C$_{10}$ alkynyl. In some embodiments, R$^2$, R$^{2'}$, R$^3$, R$^{3'}$, R$^4$, R$^{4'}$, R$^{6'}$ and R$^6$ may be each hydrogen. In some embodiments, R$^2$, R$^{2'}$, R$^3$, R$^{3'}$, R$^4$, R$^{4'}$, R$^{6'}$ and R$^6$ may each independently selected from H, OH, C$_1$-C$_6$ alkyl, C$_1$-C$_6$ alkenyl, and C$_1$-C$_6$ alkynyl. In yet other embodiments, R$^2$, R$^{2'}$, R$^3$, R$^{3'}$, R$^4$, R$^{4'}$, R$^{6'}$ and R$^6$ may be each independently selected from H, OH, and C$_1$-C$_6$ alkyl. Alternatively, R$^2$, R$^{2'}$, R$^3$, R$^{3'}$, R$^4$, R$^{4'}$, R$^{6'}$ and R$^6$ may be each independently selected from H, OH, and C$_1$-C$_3$ alkyl. In some embodiments, a C$_1$-C$_3$ alkyl substituent for R$^2$, R$^{2'}$, R$^3$, R$^{3'}$, R$^4$, R$^{4'}$, R$^{6'}$ and R$^6$ may be methyl or ethyl.

R$^5$ or R$^{5'}$ is independently selected from NH$_2$, CO$_2$H, H, OH, C$_1$-C$_{10}$ alkyl, C$_1$-C$_{10}$ alkenyl, C$_1$-C$_{10}$ alkynyl, -L-R$_x$ or -L-S$_c$. In some embodiments, R$^5$ or R$^{5'}$ may be independently selected from H, OH, C$_1$-C$_{10}$ alkyl, C$_1$-C$_{10}$ alkenyl, C$_1$-C$_{10}$ alkynyl, -L-R$_x$ or -L-S$_c$. In yet other embodiments, R$^5$ or R$^{5'}$ may be independently selected from H, OH, C$_1$-C$_6$ alkyl, C$_1$-C$_6$ alkenyl, C$_1$-C$_6$ alkynyl, -L-R$_x$ or -L-S$_c$. In some other embodiments, R$^5$ or R$^{5'}$ may be independently selected from H, OH, C$_1$-C$_6$ alkyl, -L-R$_x$ or -L-S$_c$. In some embodiments, a C$_1$-C$_6$ alkyl substituent for R$^5$ or R$^{5'}$ may be methyl or ethyl. In yet other embodiments, R$^5$ or R$^{5'}$ may be -L-R$_x$ or -L-S$_c$, with the proviso that only one -L-R$_x$ or -L-S$_c$ is present in the compound of formula I or II. The moieties -L-R$_x$ and L-S$_c$ are as defined below.

R$^8$ is H, NH$_2$, CO$_2$H, -L-R$_x$, or -L-S$_c$, wherein the carbon to which R$^8$ is attached also has a hydrogen substituent; or R$^8$ is an exo olefin having the structure

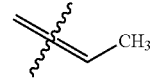 [SMILES: *=CC]

wherein the ring carbon to which R$^8$ is attached is olefinic and has no other exocyclic substituent. In some embodiments, R$^8$ may be H, NH$_2$, CO$_2$H, -L-R$_x$, or -L-S$_c$, wherein the carbon to which R$^8$ is attached also has a hydrogen substituent. In yet other embodiments, R$^8$ may be H, -L-R$_x$, or -L-S$_c$, wherein the carbon to which R$^8$ is attached also has a hydrogen substituent. In some embodiments, R$^8$ may be -L-R$_x$, or -L-S$_c$, with the proviso that the compound of formula I or II has only one -L-R$_x$, or -L-S$_c$ present in the entire molecule. The moieties -L-R$_x$ and L-S are as defined below. In yet other embodiments, R$^8$ may be an exo olefin having the structure

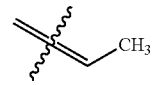 [SMILES: *=CC]

wherein the ring carbon to which R$^8$ is attached is olefinic and has no other exocyclic substituent.

X is C$_{1-12}$ alkylene, optionally wherein the alkylene chain is interrupted by one or more hetero atoms selected from the group consisting of O, S, and NH. In some embodiments, X may be methylene. In other embodiments, X may be C$_1$-C$_6$ alkylene, and may be optionally be interrupted by one heteroatom selected from O or NH.

Alternatively, X is —(CH$_2$)$_m$-Q-(CH$_2$)$_p$—, wherein m and p are each independently 0, 1 or 2. In some embodiments m and p may both selected to be 0.

Q has a structure of formula:

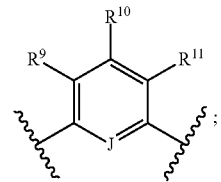

wherein each of R$^9$, R$^{10}$ and R$^{11}$ is H, NH$_2$, CO$_2$H, -L-R$_x$ or -L-S$_c$; and J is CH or N. In some embodiments, only one of R$^9$, R$^{10}$ and R$^{11}$ may be NH$_2$ or CO$_2$H, and the others of R$^9$, R$^{10}$ and R$^{11}$ may be H. In other embodiments, one of R$^9$, R$^{10}$ and R$^{11}$ may be -L-R$_x$ or -L-S$_c$, and the others of R$^9$, R$^{10}$ and R$^{11}$ may be H, with the proviso that only one -L-R$_x$ or -L-S$_c$ may be present in the compound of formula I or II. In some embodiments, R$^{10}$ may be NH$_2$ or CO$_2$H. Alternatively, R$^{10}$ may be -L-R$_x$ or -L-S$_c$ and R$^9$ and R$^{11}$ may be H. The moieties -L-R$_x$ and L-S$_c$ are as defined below Y and Y' are independently O, S, or NH. In some embodiments, Y and Y' may be O. In other embodiments, Y and Y' may be NH. Alternatively, Y and Y' may be S.

Z and Z' are independently H, R, OH, OR, SH, SR, NH$_2$, or NHR, where each R is independently unsubstituted C$_1$-C$_{12}$ alkyl, substituted C$_1$-C$_{12}$ alkyl, unsubstituted C$_3$-C$_{20}$ heterocyclyl, substituted C$_3$-C$_{20}$ heterocyclyl, unsubstituted C$_6$-C$_{20}$ aryl groups, and unsubstituted C$_6$-C$_{20}$ aryl groups. In some embodiments, Z and Z' may be independently H, R, OH, OR wherein each R may be independently unsubstituted C$_1$-C$_{12}$ alkyl or substituted C$_1$-C$_{12}$ alkyl. In some embodiments, Z and Z' may be independently H, R, OH, OR wherein each R may be independently unsubstituted C$_1$-C$_6$ alkyl or substituted C$_1$-C$_6$ alkyl. In yet other embodiments, Z and Z may be independently H, CH$_3$, CH$_2$CH$_3$, OH, OCH$_3$, or OCH$_2$CH$_3$.

Linker L is a bond or is a moiety having 1-200 nonhydrogen atoms selected from C, N, O, S, or halogen, and optionally incorporates ether, oxo, carboxyl, carboxamide, carboxamidyl, urethanyl, branched, cyclic, unsaturated, amino acid, heterocyclic, aromatic or heteroaromatic moieties. Linker L may be unbranched or branched, flexible or rigid, short or long and may incorporate any combination of moieties as deemed useful. In some embodiments, at least a portion of the linker L may have a polyalkylene oxide polymeric region, which may enhance solubility of the compound of formula I or II. In some embodiments, the linker L may have a repeating unit of ethylene glycol, and may have a number of repeating ethylene glycol units of about 1 to about 25, or any number therebetween. In some embodiments, L may include about 3 to about 20, about 4 to about 15, about 5 to about 12 or about 6 to about 10 ethylene glycol units. In some embodiments, at least a portion of Linker L may include one or more amino acid moieties which may provide enhanced solubility for the compound of formula I or II or may provide amino acid sequences to enhance target binding, enhance compatibility with a target binding agent, or enhance target binding recognition. In other embodiments, the linker L may include one or more amino acid moieties that provide a suitable substrate motif for a protease. When a set of amino acid moieties are incorporated into the linker L that provide a substrate motif specific for a selected protease, the cytotoxic drug compound of Formula I or II may be released from a target bound conjugate to provide localized cytotoxic effects. Such substrate motifs are known in the art and may be incorporated into the linker L as desired to provide selective release from the target bound conjugate. This selectivity can be based on known presence of a desired protease within the localized delivery region of the conjugate drug. Other polymeric types of moieties may be incorporated in the linker L, such as polyacids, polysaccharides, or polyamines. Other moieties such as substituted aromatic or heteroaromatic moieties may be used to enhance rigidity or provide synthetically accessible sites on substituents therein for linking to reactive moieties or to the compound of formula I or II.

For example, the linker L can include ethylene glycol repeating units, and an amino acid sequence. In some embodiments, linker L includes the formula:

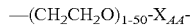

wherein X$_{AA}$ is an amino acid sequence.

Any suitable number of ethylene glycol units can be used in the linker L of the present invention. For example, the linker L can include 1, 2, 3, 4, 5, 6, 7, 8, 9, 10, 11, 12, 15, 16, 19, 20, 23, 24, 35, 36, 37, 48, 49, or more ethylene glycol units. In some embodiments, the linker L can include 8 ethylene glycol units. Several commercially available ethylene glycol groups (polyethylene glycol, PEG) are suitable in the linker L, such as H$_2$N-dPEG®$_8$-C(O)OH, having a discrete ("d") polyethylene glycol having 8 ethylene glycol repeating units. Other discrete PEG units are commercially available and known to one of skill in the art, such as by Advanced ChemTech, In some embodiments, the linker L includes the formula:

wherein PEG has 1-50 ethylene glycol units, and X$_{AA}$ is an amino acid sequence.

The amino acid portion of the linker L can include any suitable number of amino acid moieties, as described above. For example, the amino acid sequence XAA can include from 1 to 100 amino acid moieties, or from 1 to 10 amino acid moieties, or from 1 to 5 amino acid moieties. The linker L can include 1, 2, 3, 4, 5, 6, 7, 8, 9, 10, or more amino acid moieties. In some embodiments, the linker L includes 2 amino acid moieties. In some embodiments, the linker L includes the amino acid sequence Val-Ala. In some embodiments, the linker L includes the formula:

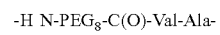

wherein PEG$_8$ has 8 ethylene glycol units.

The linker L can also include a variety of other connecting groups that connect the ethylene glycol portion to the amino acid sequence, or connect the ethylene glycol or amino acid sequence to the reactive moiety R$_x$, substance S$_c$, or the compound of Formula I or II. For example, the amino acid sequence can be connected to the compound of Formula I or II via a 4-amino benzyl carboxylate group. In some embodiments, the ethylene glycol portion ca be directly linked to the reactive moiety R$_x$ or the substance S$_c$. In some embodiments, the linker L has the formula:

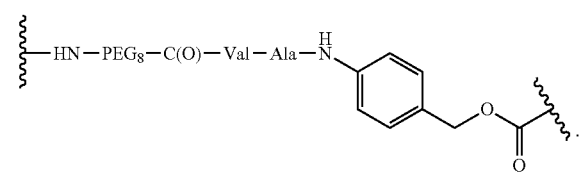

R$_x$ is a reactive moiety. R$_x$ may be any suitable reactive moiety as long as it is capable of reacting with a correspondingly reactive moiety present on the substance S$_c$, which may be a target binding agent as described herein. In various embodiments, S$_c$ is a protein or a portion of a protein, and have accessible conjugatable moieties such as:

Thiols/disulfides. Reactive moieties R$_x$ that can react with thiols or disulfides include maleimide, iodoacetamide, azide, thiazole and pyrridopyridazine. Disulfides may also be labeled by use of a bisulfone reactive moiety. Additionally malemide reactive moieties can react with engineered selenocysteine moieties.

Amines. Reactive moieties R$_x$ that may be used to couple IQB compounds to a target binding agent S$_c$ include isothiocyanate, succinimidyl ester, sulfonyl halide, carboxylic acids (in the presence of carbodiimide coupling reagents), sulfosuccinimidyl ester, 4-sulfotetrafluorophenyl ester, tetrafluorophenyl ester, and sulfodichlorophenol ester. This list is in no way limiting and other reactive moieties R$_x$ that are capable of reacting with an amine of a target binding agent S$_c$ may be used.

Aldehydes/ketones. These moieties may be introduced into a target binding agent Sc and subsequently reacted with a compound of formula I or II having a -L-Rx where the reactive moiety Rx is hydrazine, semihydrazide, carbohydrazide, or hydroxylamine. This list is in no way limiting and other reactive moieties $R_x$ that are capable of reacting with an aldehyde of a target binding agent $S_c$ may be used.

Other reactive moieties $R_x$ that are useful in the compounds of formula I and II include azides, phosphines, or alkynes which can be used in Staudinger reactions, Pictet-Spengler reactions and/or Click-type chemistry (Copper containing or not), all of which are currently under active investigation for selective labeling of proteins including antibodies and their fragments. This is a non-limiting list of reactive moieties $R_x$ useful for reacting with engineered sites on target binding agents $S_c$.

In some embodiments, $R_x$ may be maleimide, bis-sulfone, iodoacetamide, azide, isothiocyanate, succinimidyl ester, sulfonyl halide, carboxylic acids, semihydrazide, carbohydrazide, hydroxylamine, phosphine, or alkyne.

-L-$R_x$ is a linker L attached to a reactive moiety $R_x$. -L-$R_x$ may be used in a compound of formula I or II to form a reagent bearing IQB compounds that can attach to a substance $S_c$, which may be a target binding agent as described herein. Any combination of linker L and reactive moiety $R_x$ described herein may be used in the compounds of formula I or II. See FIG. 2 for some exemplary -L-$R_x$.

A number of other chemistries are known for attachment of compounds to antibodies. U.S. Pat. No. 7,595,292 (Brocchini et al.) refers to linkers that form thioesters with the sulfurs in a disulfide bond of an antibody. U.S. Pat. No. 7,985,783 (Carico et al.) refers to the introduction of aldehyde residues into antibodies, which are used to couple compounds to the antibody.

$S_c$ is a target binding agent selected from a protein, a portion of a protein, a peptide, or a nucleic acid. In some embodiments, a target-binding agent that is a protein may include an antibody, an antibody fragment, or an antibody single-chain fragment variable ("scFV"). The target-binding agent may bind to a tumor-associated antigen, a cancer-stem-cell associated antigen or a viral antigen.

In various embodiments, the target-binding agent $S_c$ may bind to a target selected from an acute myeloid leukemia (AML M4) cell, an acute promyelocytic leukemia cell, an acute lymphoblastic leukemia cell, an acute lymphocytic leukemia cell, a chronic lymphocytic leukemia cell, a chronic myeloid leukemia cell, a chronic T-cell lymphocytic leukemia, a myelodysplastic syndromic cell, a multiple myeloma cell, a prostate carcinoma cell, a renal cell adenocarcinoma cell, a pancreatic adenocarcinoma cell, a lung carcinoma cell or a gastric adenocarcinoma cell, a gastric adenocarcinoma cell, a breast cancer cell, a colon cancer cell, a melanoma cell, a thyroid cancer cell, an ovarian cancer cell, a bladder cancer cell, a liver cancer cell, a head and neck cancer cell, an esophageal cancer cell, a hodgkin lymphoma cell, a non-hodgkin lymphoma cell, a mesothelioma cell, a neuroblastoma cell, a neuroendocrine tumor cell, a neurofibromatosis type 1 (NF1) cell, a neurofibromatosis type 2 (NF2) or an osteosarcoma cell.

In some other embodiments, the target-binding agent $S_c$ may bind a target selected from CLL-1, IL1RAP, TIM-3, CD19, CD20, CD22, ROR1, mesothelin, CD33, CD123/IL3Ra, GPR114, c-Met, PSMA, prostatic acid phosphatase (PAP), CEA, CA-125, Muc-1, AFP, Glycolipid F77, EGFRvIII, GD-2, NY-ESO-1 TCR, tyrosinase, TRPI/gp75, gp100/pmeI-17, Melan-A/MART-1, Her2/neu, WT1, EphA3, telomerase, HPV E6, HPV E7, EBNA1, BAGE, GAGE and MAGE A3 TCRSLITRK6, ENPP3, Nectin-4, CD27, SLC44A4, CAIX, Cripto, CD30, MUC16, GPNMB, BCMA, Trop-2, Tissue Factor (TF), CanAg, EGFR, αv-integrin, CD37, Folate Receptor-α, CD138, CEACAM5, CD56, CD70, CD74, GCC, 5T4, CD79b, Steap1, Napi2b, Lewis Y Antigen, LIV, c-RET, DLL3, EFNA4, Endosialin/CD248.

In yet other embodiments, the target-binding agent $S_c$ may be a bi-specific antibody/antibody fragment. In some embodiments, the bi-specific antibody/antibody fragment binds to one or two targets selected from CLL-1, IL1 RAP, TIM-3, CD19, CD20, CD22, ROR1, mesothelin, CD33, CD123/IL3Ra, GPR114, c-Met, PSMA, prostatic acid phosphatase (PAP), CEA, CA-125, Muc-1, AFP, Glycolipid F77, EGFRvIII, GD-2, NY-ESO-1 TCR, tyrosinase, TRPI/gp75, gp100/pmeI-17, Melan-A/MART-1, Her2/neu, WT1, EphA3, telomerase, HPV E6, HPV E7, EBNA1, BAGE, GAGE and MAGE A3 TCRSLITRK6, ENPP3, Nectin-4, CD27, SLC44A4, CAIX, Cripto, CD30, MUC16, GPNMB, BCMA, Trop-2, Tissue Factor (TF), CanAg, EGFR, αv-integrin, CD37, Folate Receptor, CD138, CEACAM5, CD56, CD70, CD74, GCC, 5T4, CD79b, Steap1, Napi2b, Lewis Y Antigen, LIV, c-RET, DLL3, EFNA4, Endosialin/CD248.

-L-$S_c$ is a linker L attached to a substance $S_c$. -L-$S_c$ may be used in a compound of formula I or II to form a conjugated species bearing IQB compounds that are attached to a substance $S_c$ which may be a target binding agent as described above and throughout this disclosure. Any combination of linker L and substance $S_c$ described herein may be used in the compounds of formula I or II.

When -L-$R_x$ or -L-$S_c$ is present in the compound of formula I or II, only one of $R^b$, $R^{b'}$, $R^5$, $R^{5'}$, $R^8$, $R^9$, $R^{10}$, $R^{11}$ is -L-$R_x$ or -L-$S_c$. Only one linker containing a reactive moiety or a linker attached to substance $S_c$ may be present in the compound of formula I or II. In some embodiments, neither -L-$R_x$ or -L-$S_c$ is present in the compound of formula I or II.

In some embodiments, the compound of formula I or II has a formula wherein Y and Y' are each O and none of $R^b$, $R^{b'}$, $R^5$, $R^{5'}$, $R^8$, $R^9$, $R^{10}$, $R^{11}$ is -L-$R_x$ or -L-S.

In some embodiments, the compound of formula I or II has a formula where Y and Y' are each O and Z and Z' are each independently selected from H and $C_1$-$C_3$ alkoxy.

In other embodiments, the compound of formula I or II has a formula where Y and Y' are each O; Z and Z' are each independently selected from H and $C_1$-$C_3$ alkoxy, and X is —$CH_2$—.

In some embodiments, the compound of formula I or II has a formula where Y and Y' are each O; Z and Z' are each independently selected from H and $C_1$-$C_3$ alkoxy; X is Q and J is CH.

In some embodiments, the compound of formula I or II has a formula where Y and Y' are each O; Z and Z' are each independently selected from H and $C_1$-$C_3$ alkoxy; and one of $R^9$, $R^{10}$ or $R^{11}$ is -L-$R_x$ or -L-$S_c$.

In some embodiments, the compound of formula I or II has a formula where Y and Y' are each O; Z and Z' are each independently selected from $C_1$-$C_3$ alkoxy; and one of $R^5$ or $R^{5'}$ is -L-$R_x$ or -L-$S_c$.

In some embodiments, the compound of formula I or II has a formula where Y and Y' are each O; Z and Z' are each independently selected from H and $C_1$-$C_3$ alkoxy; and when $R^b$ or $R^{b'}$ is present, then one of $R^b$ or $R^{b'}$ is -L-$R_x$ or -L-$S_c$.

In some embodiments, the compound of formula I or II has a formula where Y and Y' are each O; Z and Z' are each independently selected from $C_1$-$C_3$ alkoxy; and $R^8$ is -L-$R_x$ or -L-$S_c$.

In some embodiments, a compound of formula I and II includes:
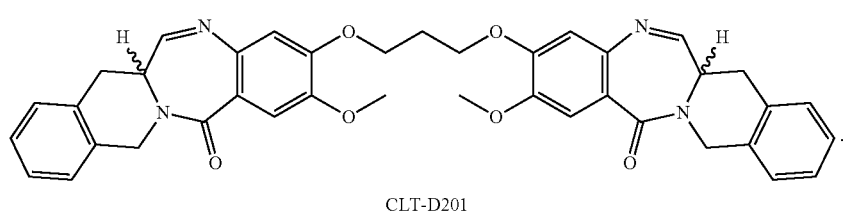
CLT-D201
In other embodiments, a compound of formula I and II includes:
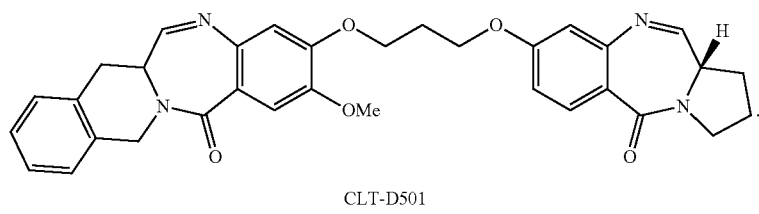 [SMILES: COc1cc2c(cc1OCCCOc1ccc3c(c1)N=C[C@@H]1CCCN1C3=O)N=CC1Cc3ccccc3CN1C2=O]
CLT-D501
In other embodiments, a compound of formula I and II includes:
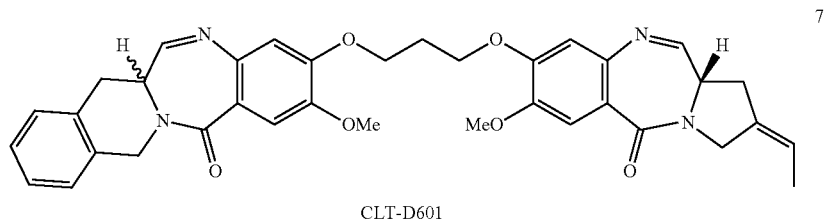 [SMILES: C/C=C1/C[C@H]2C=Nc3cc(OCCCOc4cc5c(cc4OC)C(=O)N4Cc6ccccc6CC4C=N5)c(OC)cc3C(=O)N2C1]
CLT-D601

In some other embodiments, a compound of formula I has the following structure:

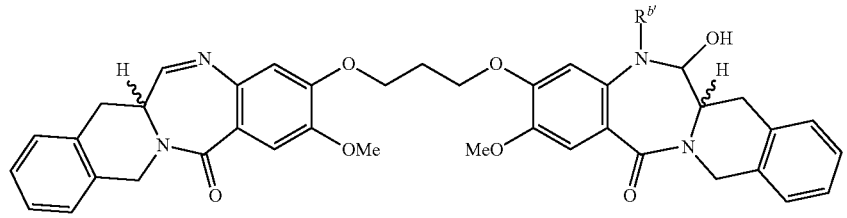

wherein $R^{b'}$ is -L-$R_x$.

In yet other embodiments, a compound of formula I or II, having a substituent -L-$R_x$ is the following compound:

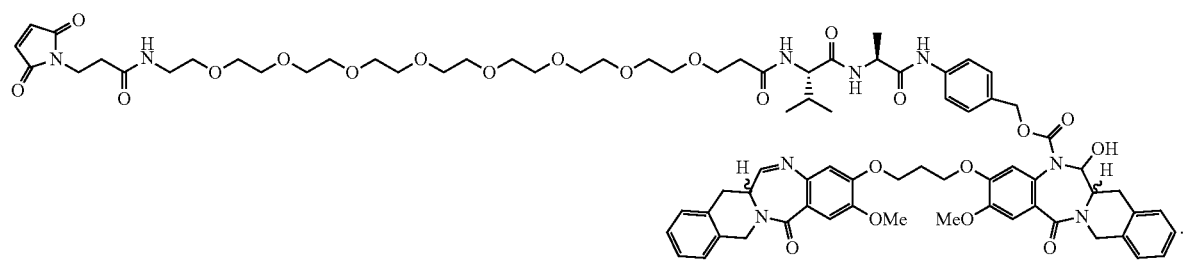 [SMILES: COc1cc2c(cc1OCCCOc1cc3c(cc1OC)C(=O)N1Cc4ccccc4CC1C(O)N3C(=O)OCc1ccc(NC(=O)[C@H](C)NC(=O)[C@@H](NC(=O)CCOCCOCCOCCOCCOCCOCCOCCOCCNC(=O)CCN3C(=O)C=CC3=O)C(C)C)cc1)N=CC1Cc3ccccc3CN1C2=O]

In yet other embodiments, a compound of formula I or II, having a substituent -L-$R_x$ is the following compound:

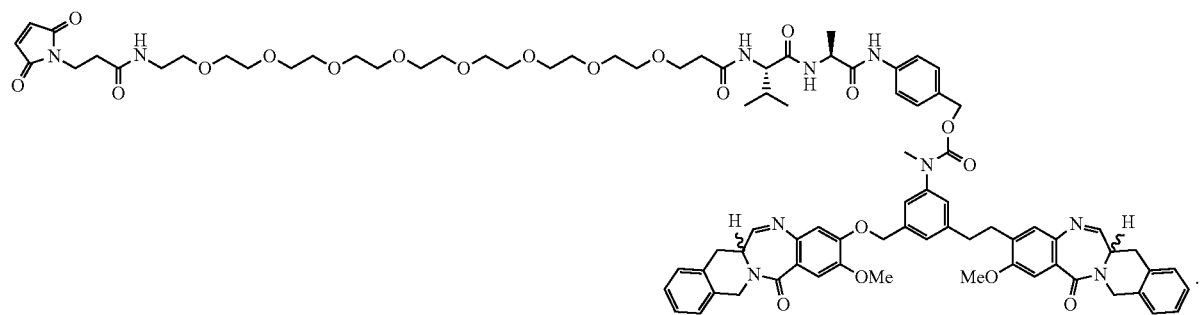 [SMILES: COc1cc2c(cc1CCc1cc(COc3cc4c(cc3OC)C(=O)N3Cc5ccccc5CC3C=N4)cc(N(C)C(=O)OCc3ccc(NC(=O)[C@H](C)NC(=O)[C@@H](NC(=O)CCOCCOCCOCCOCCOCCOCCOCCOCCNC(=O)CCN4C(=O)C=CC4=O)C(C)C)cc3)c1)N=CC1Cc3ccccc3CN1C2=O]

In other embodiments, a compound of formula I or II, having a substituent -L-$R_x$ is the following compound:

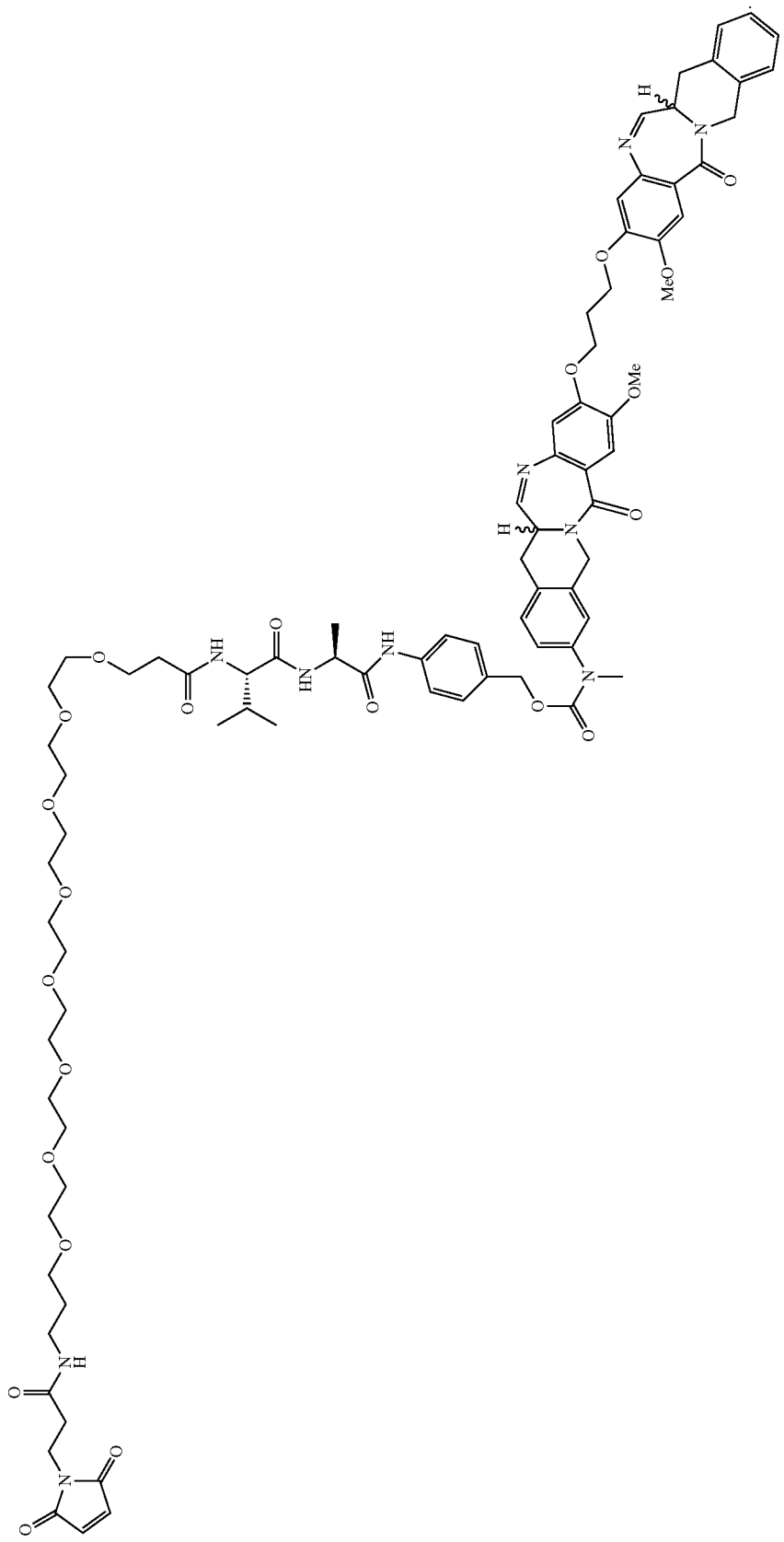

In other embodiments, a compound of formula I or II, having a substituent -L-R$_x$ is the following compound:
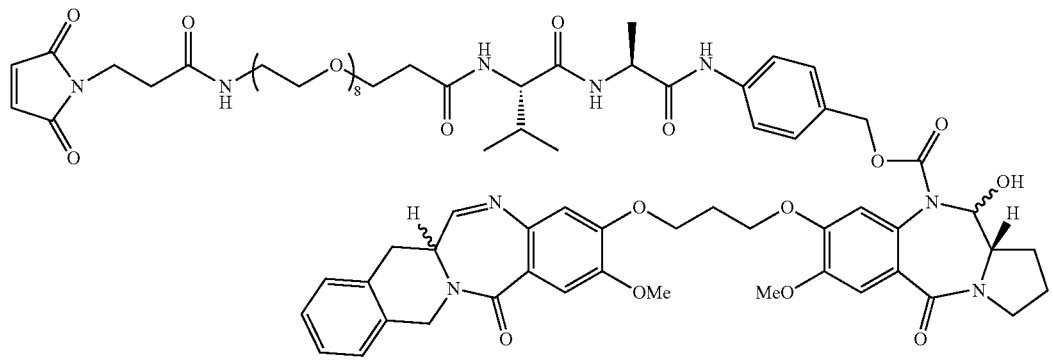
In other embodiments, a compound of formula I or II, having a substituent -L-R$_x$ is the following compound:
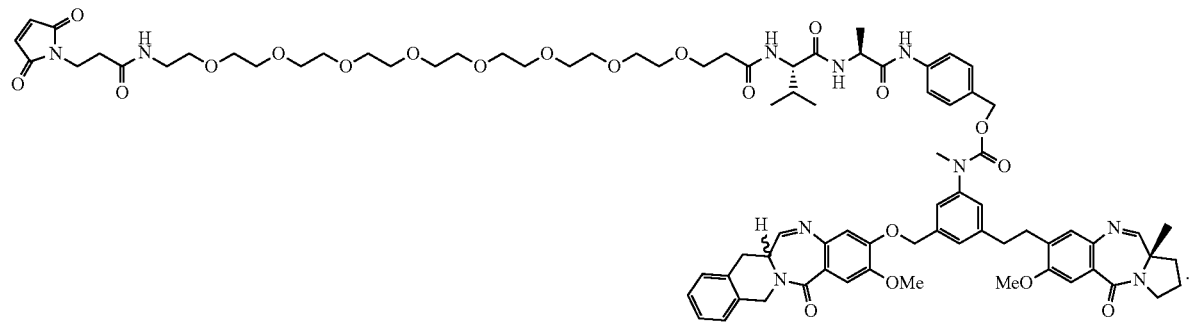 [SMILES: COc1cc2c(cc1CCc1cc(COc3cc4c(cc3OC)C(=O)N3Cc5ccccc5CC3C=N4)cc(N(C)C(=O)OCc3ccc(NC(=O)[C@H](C)NC(=O)[C@@H](NC(=O)CCOCCOCCOCCOCCOCCOCCOCCOCCNC(=O)CCN4C(=O)C=CC4=O)C(C)C)cc3)c1)N=C[C@]1(C)CCCN1C2=O]
In other embodiments, a compound of formula I or II, having a substituent -L-R, is the following compound:

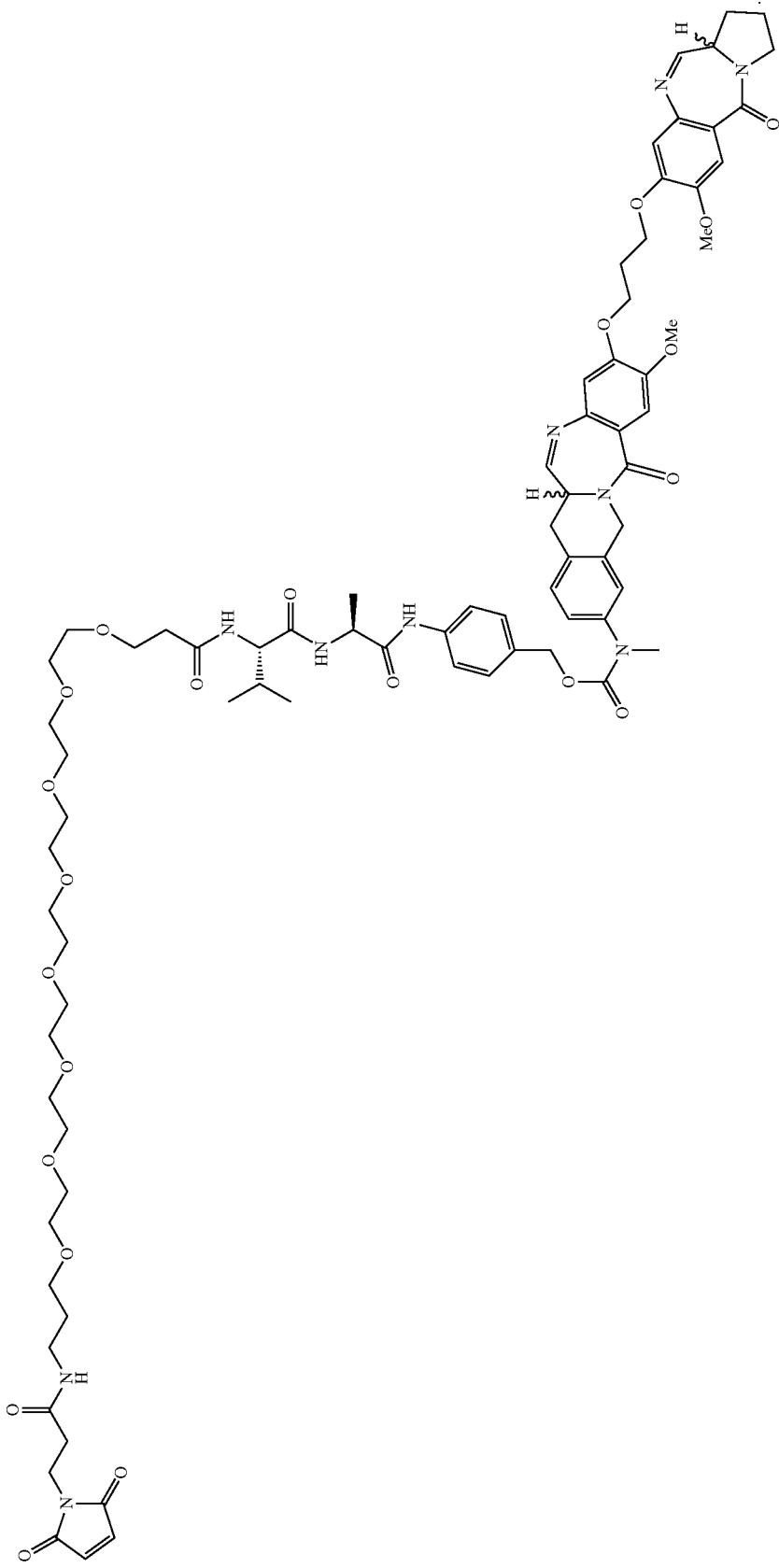

In other embodiments, a compound of formula I or II, having a substituent -L-R$_x$ is the following compound:
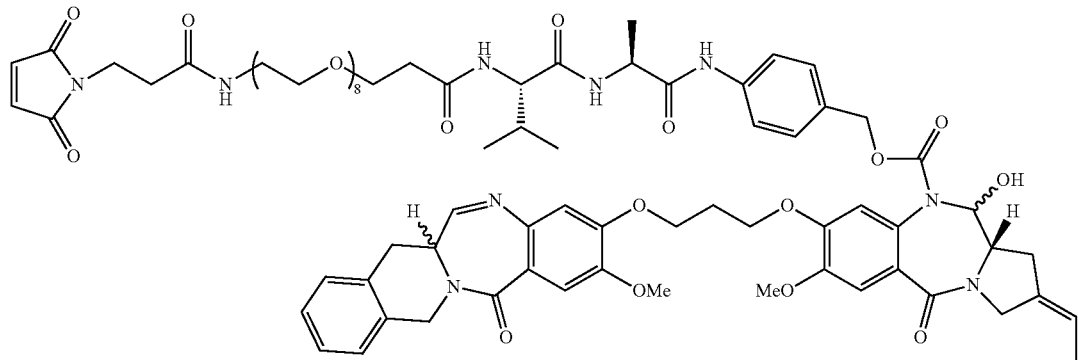
In other embodiments, a compound of formula I or II, having a substituent -L-R, is the following compound:
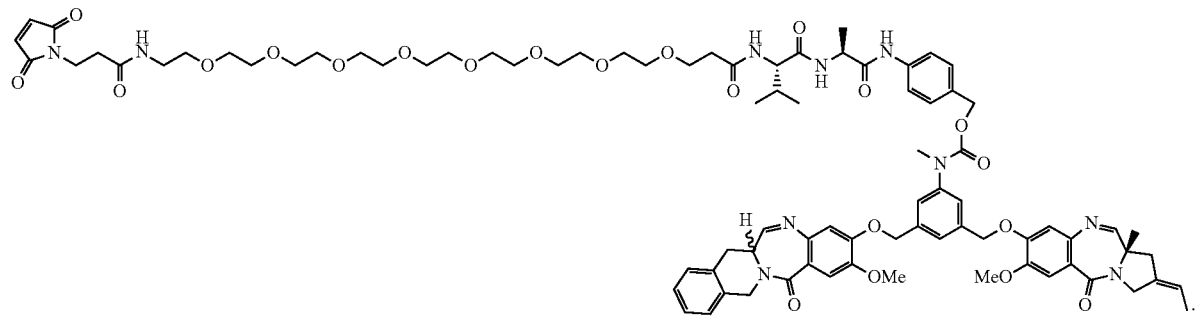 [SMILES: C/C=C1\CN2C(=O)c3cc(OC)c(OCc4cc(COc5cc6c(cc5OC)C(=O)N5Cc7ccccc7CC5C=N6)cc(N(C)C(=O)OCc5ccc(NC(=O)[C@H](C)NC(=O)[C@@H](NC(=O)CCOCCOCCOCCOCCOCCOCCOCCOCCNC(=O)CCN6C(=O)C=CC6=O)C(C)C)cc5)c4)cc3N=C[C@]2(C)C1]
In other embodiments, a compound of formula I or II, having a substituent -L-R$_x$ is the following compound:

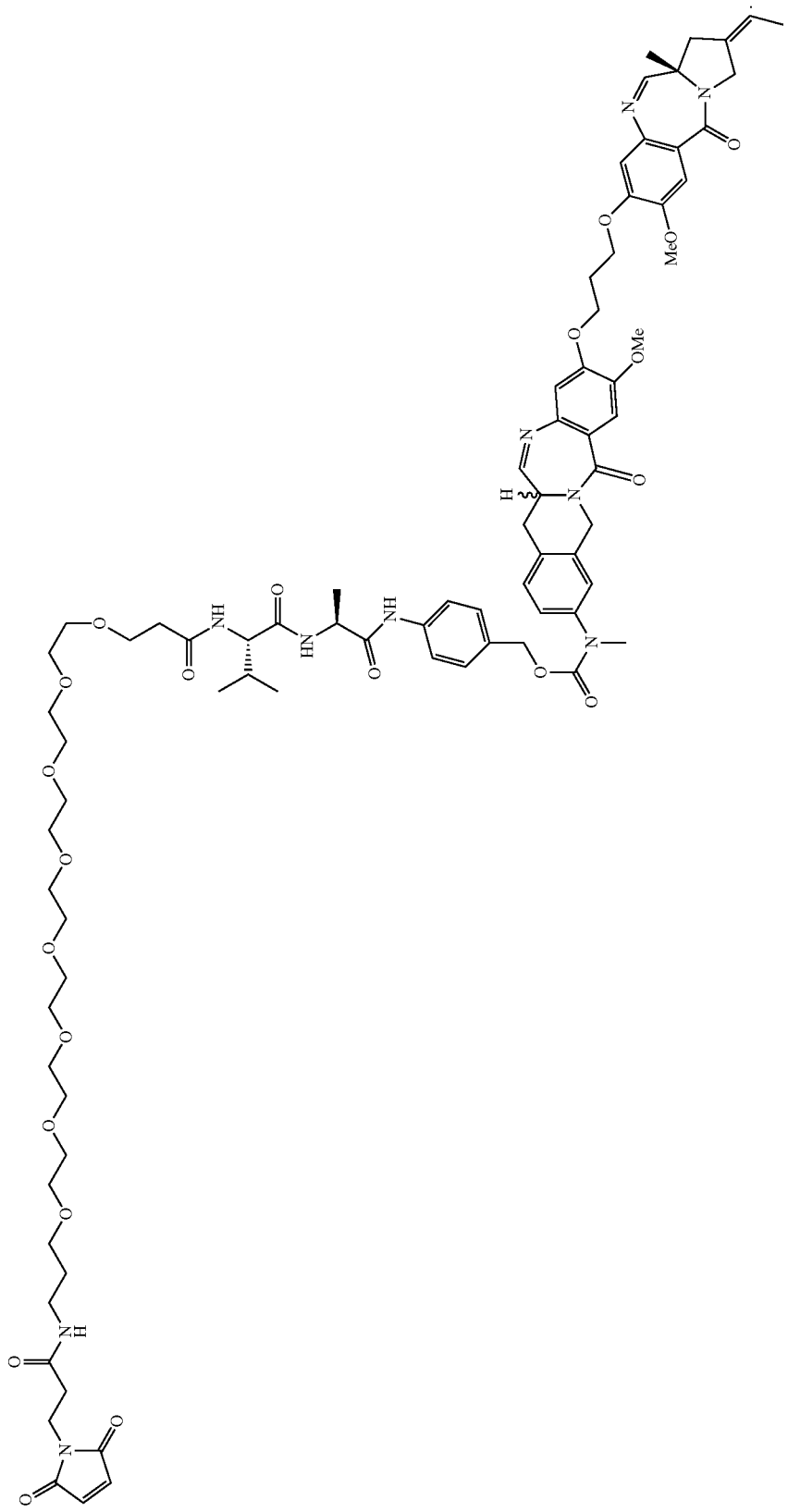

A. Description of how to Obtain Compounds

Figure 3:
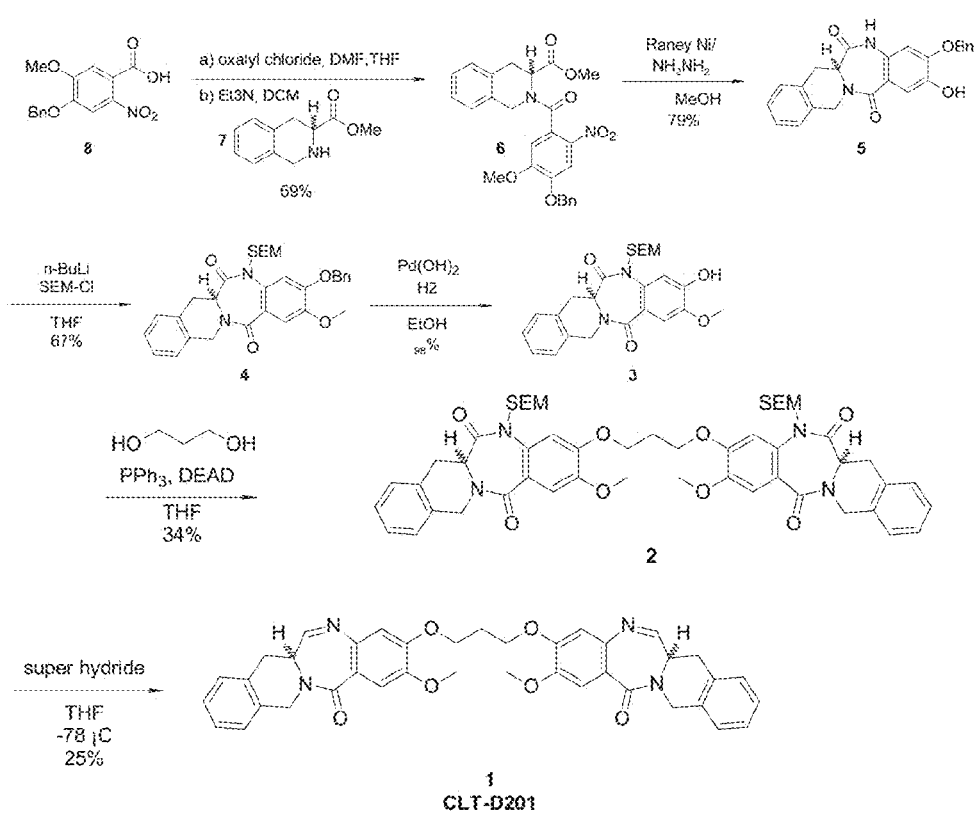
FIG. 3 shows an experimental scheme for the chemical synthesis of CLT-D201.
Figure 4:
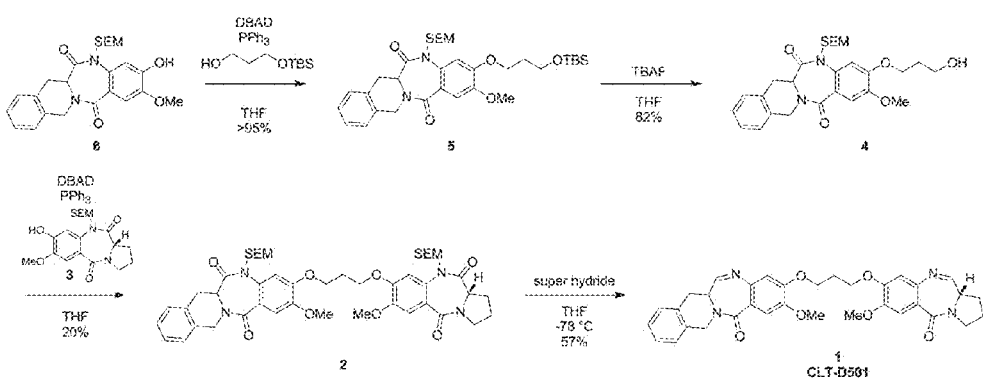
FIG. 4 shows an experimental scheme for the chemical synthesis of CLT-D501.
Figure 5:
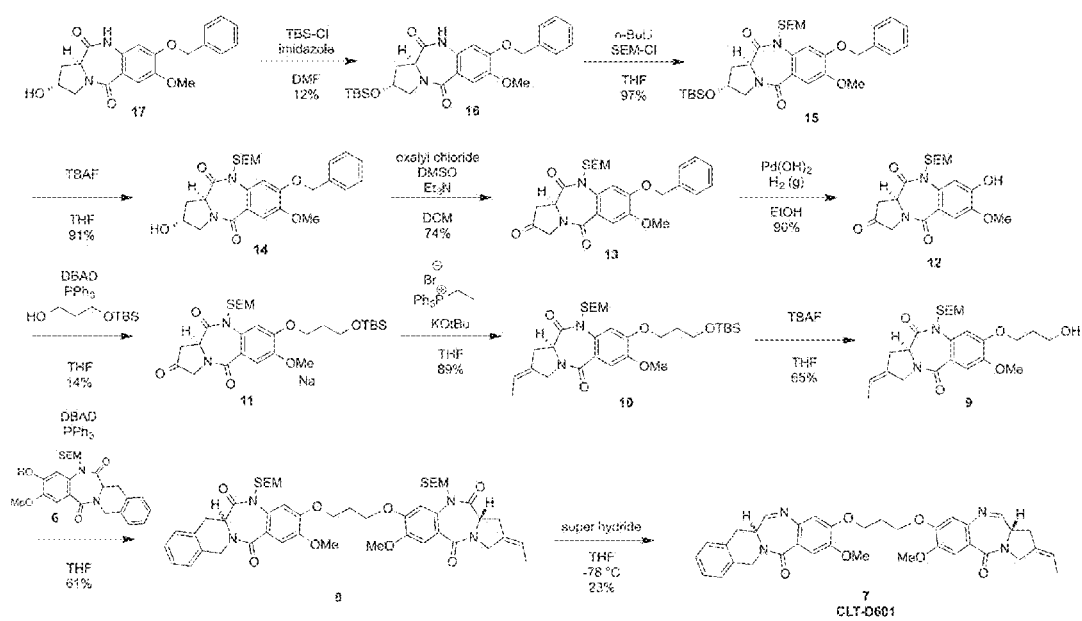
FIG. 5 shows an experimental scheme for the chemical synthesis of CLT-D601.

The IQB compounds can be synthesized via numerous routes. One exemplary route to an IQB compound, referred to as CLT-D201, is shown in FIG. 3, in the steps condensing isoquinolidinyl compound 7 with ortho-nitrobenzoic acid 8 followed by further chemical transformations to form an isoquinolidino-benzodiazepine 3. The deprotected isoquinolidinobenzodiazepine 3 can be coupled to another benzodiazepine derivative, which is either the same or may be different from compound 3 by performing a Mitsonobu reaction using diethylazidodicarboxylate and triphenyl phosphine to form diaryl ether linked benzodiazepine 2, which can be transformed to the reduced form compound 1. FIG. 4 shows a similar process where the two benzodiazepines are not the same (precursor 4 is an isoquinolidinobenzodiazepine while precursor 3, while having a benzodiazepine moiety, does not have an isoquinolidinyl moiety. The two differing benzodiazepine groups are coupled similarly to the process shown in FIG. 4, using Mitsonobu chemistry again to introduce stepwise the aryl ether bridge linking the two benzodiazepine groups. FIG. 5 shows a synthetic sequence to provide yet another class of IQB. It can be seen from these two synthetic sequences that a large variety of different benzodiazepinyl moieties can be incorporated into the IQB compounds of formula I and II.

Additionally, the precursor to the linking aryl di-ether bridge can incorporate many varieties of substitutions and additions. For example, as shown in the Compound A shown below, a diol incorporating an amino substituted benzyl moiety is used to form the aryl di-ether bridge. A wide variety of diol intermediates are envisioned to be useful in the compounds of formula I or II.

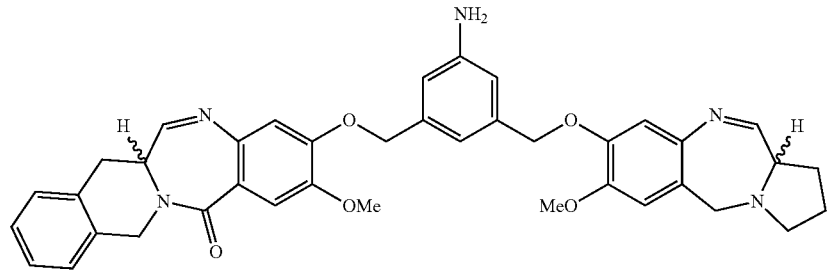

Compound A

As shown in compound A, the amino moiety may be used to attach to the Linker L and further elaborated to form a compound of formula I or II having a -L-$R_x$, which can then be reacted with a target binding agent $S_c$ to form a conjugate compound of formula I or II having a -L-$S_c$. Many differing linkers-L- and $R_x$ may be may be provided using this synthetic approach.

One example is shown below:

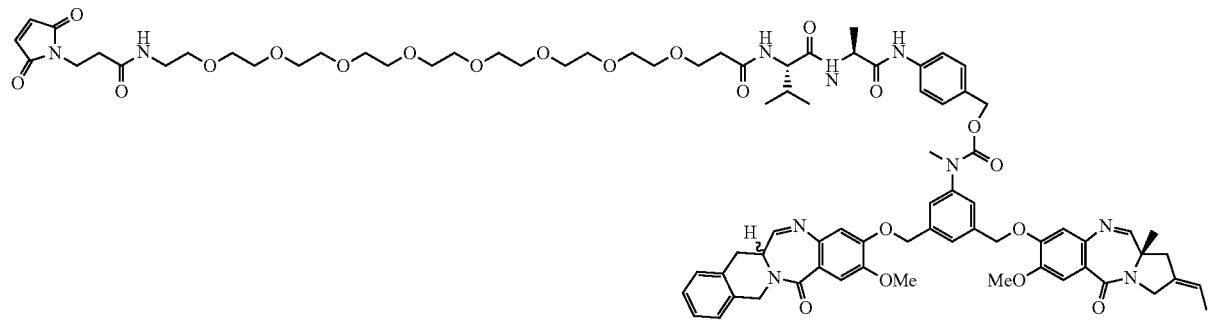 [SMILES: C/C=C1\CN2C(=O)c3cc(OC)c(OCc4cc(COc5cc6c(cc5OC)C(=O)N5Cc7ccccc7CC5C=N6)cc(N(C)C(=O)OCc5ccc(NC(=O)[C@H](C)NC(=O)[C@@H](NC(=O)CCOCCOCCOCCOCCOCCOCCOCCOCCNC(=O)CCN6C(=O)C=CC6=O)C(C)C)cc5)c4)cc3N=C[C@]2(C)C1]

Linkers including a reactive moiety, $R_x$, can be attached at positions $R^5$, $R^{5'}$, $R^b$, $R^{b'}$ or X through synthetic schemes depicted in FIGS. 7A-7C, 8, 9A and 9B.

Figure 7A:
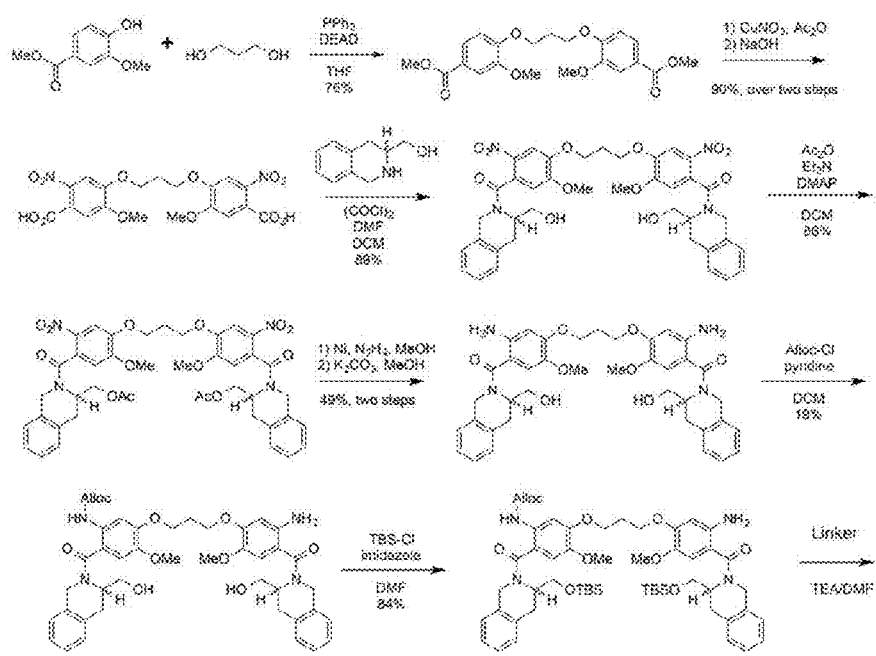
FIG. 7A, FIG. 7B and FIG. 7C show an experimental scheme for the chemical synthesis of CLT-D202, including linker synthesis.
Figure 7B:
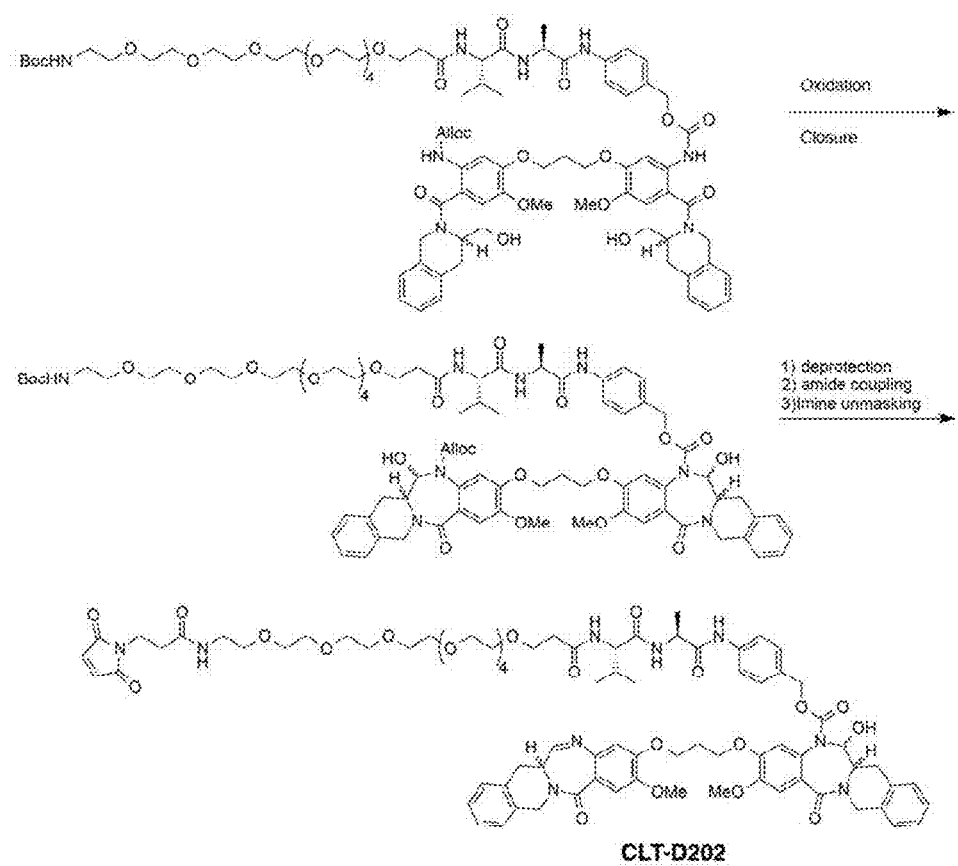
Figure 7C:
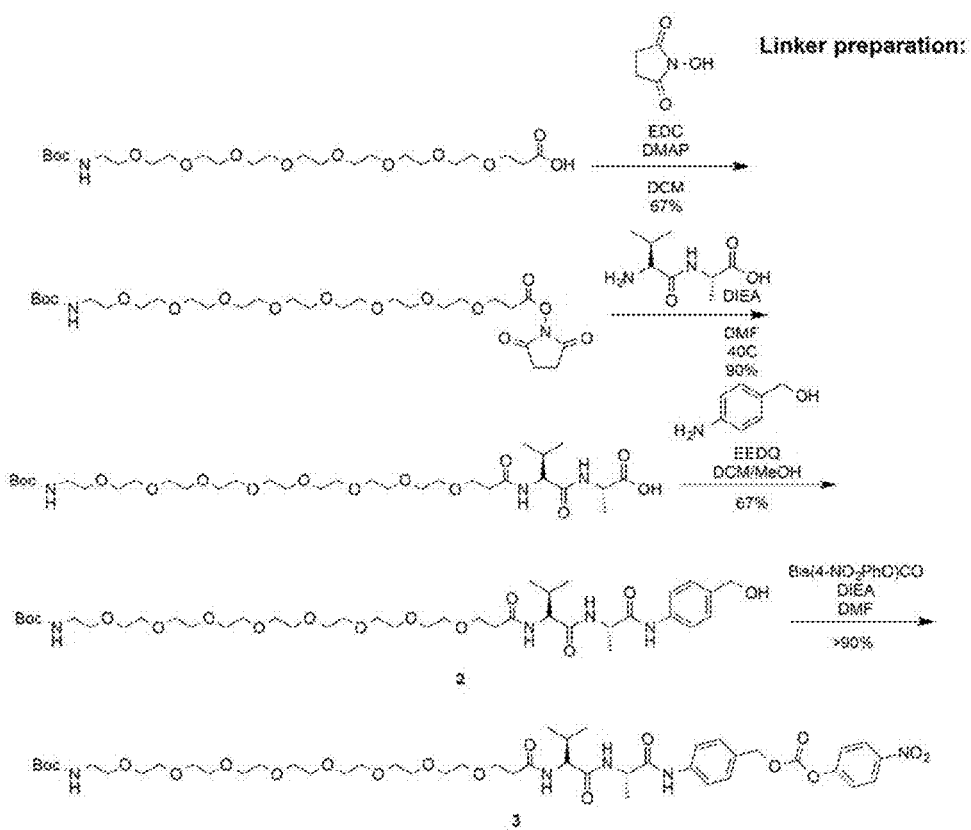

In FIG. 7C of the synthetic scheme of FIGS. 7A-7C, the synthesis of linker 3 is shown. A N-tert-butoxycarbonate (Boc)-protected amino-polyethylene glycol (PEG) substituted acetic acid is converted to a succinimide ester, using a carbodiimide coupling reagent, EDC, and succinimide in the presence of 4-dimethylaminopyridine (DMAP). This activated succinimide ester is then coupled to the N-terminal amino of the dipeptide valinylalanine in the presence of diisopropylethyl amine (DIEA) in dimethylformamide (DMF). The carboxylic acid of the resulting Boc-amino-PEG-dipeptide is subsequently coupled to the amino group of p-aminobenzyl alcohol via a carbodiimide catalyzed coupling, using N-ethoxycarbonyl-2-ethoxy-1,2-dihydroquinoline (EEDQ), to produce the linker 3 precursor having a synthetically accessible benzyl alcohol functionality. That benzyl alcohol moiety is converted to an activated para-nitrophenyl carbonate ester by reaction with the bis (4-nitrophenyl carbonate ester in the presence of DIEA in DMF to provide the linker 3, which has a activated nitrophenyl carbonate ester capable of being displaced by an amino functionality of an IQB compound of formula I or II.

In FIG. 7A, the synthesis of an exemplary compound of formula I or II, is shown, following a general synthetic route as described above, but specifically showing introduction of nitro groups into the bis aryl ethers, prior to introduction of the isoquinolidinyl rings. After acetylating the hydroxyl groups of the isoquinolidinyl moieties, the nitro substituents are reduced to amino groups in a two step transformation. Selectively producing only one of the two amino substituents permits, after introducing silyl protecting groups onto hydroxyl groups, introduction of the linker 3 to only one substituent position, at the unprotected amino substituent position, as shown in the first structure of FIG. 7B. The remainder of the IQB ring nucleus is then completed by cyclization after oxidation. The reactive moiety, maleimide, is introduced in the last series of three steps, including removal of the Boc-protecting group, and introduction of a 3-maleimidyl propionyl moiety coupled to the free amine, thus providing CLT-D202, an example of a compound of formula I having a -L-$R_x$ substituent at $R^{b'}$, which is configured to react with a target binding agent $S_c$.

Figure 8:
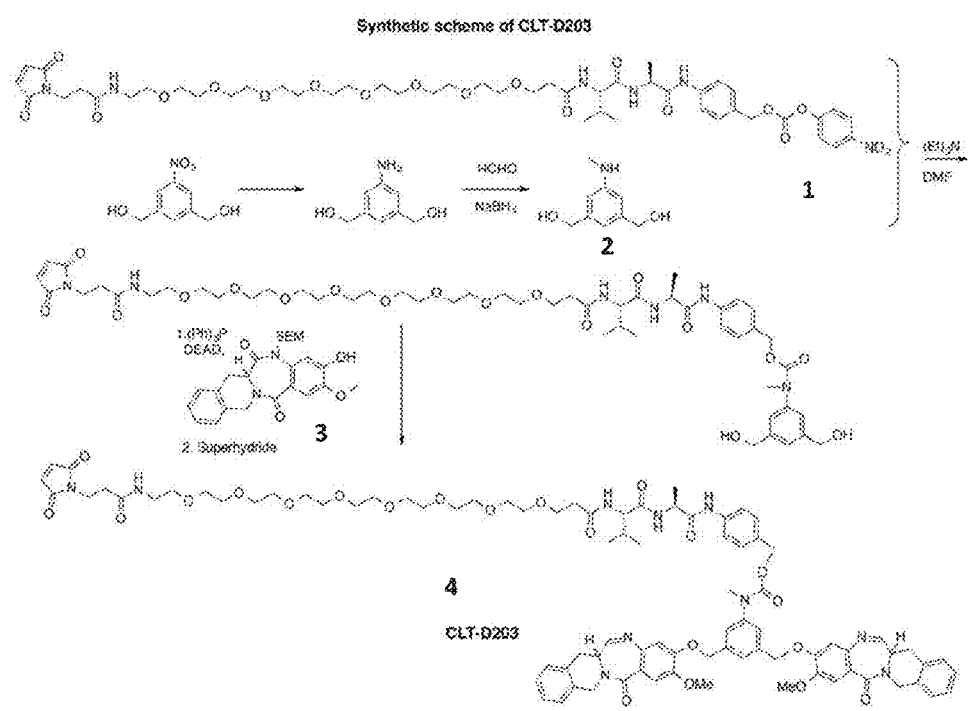
FIG. 8 shows an experimental scheme for the chemical synthesis of CLT-D203.

In FIG. 8, linker 1, which is synthesized similarly as discussed for linker 3, is coupled to 1-methylamino-2, 4, di-(hydroxymethyl) benzene (compound 2), via the activated nitrophenyl carbonate ester form moiety X. This, in turn, is bis-coupled to isoquinolidino compound 3 to provide the product compound 4, another exemplar of a compound of formula I having a -L-$R_x$ at $R^{10}$ of moiety Q, when X of formula I is Q. Compound 4 has a reactive moiety $R_x$ that is maleimide.

Figure 9A:
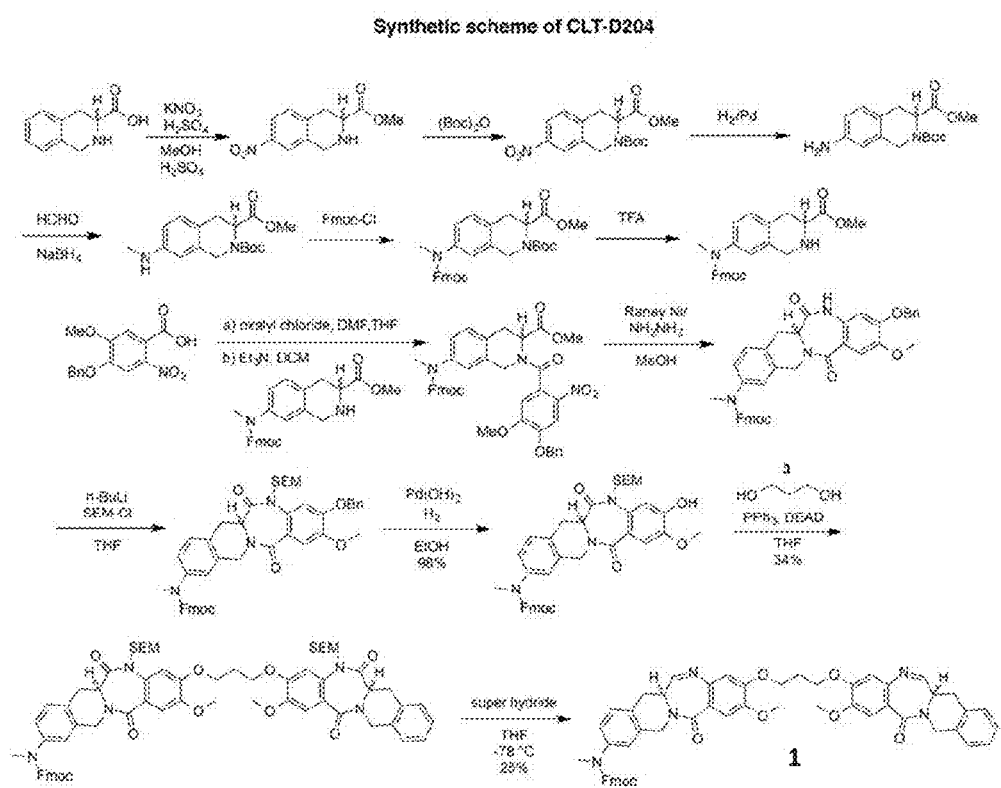
FIG. 9A and FIG. 9B show an experimental scheme for the chemical synthesis of CLT-D204.
Figure 9B:
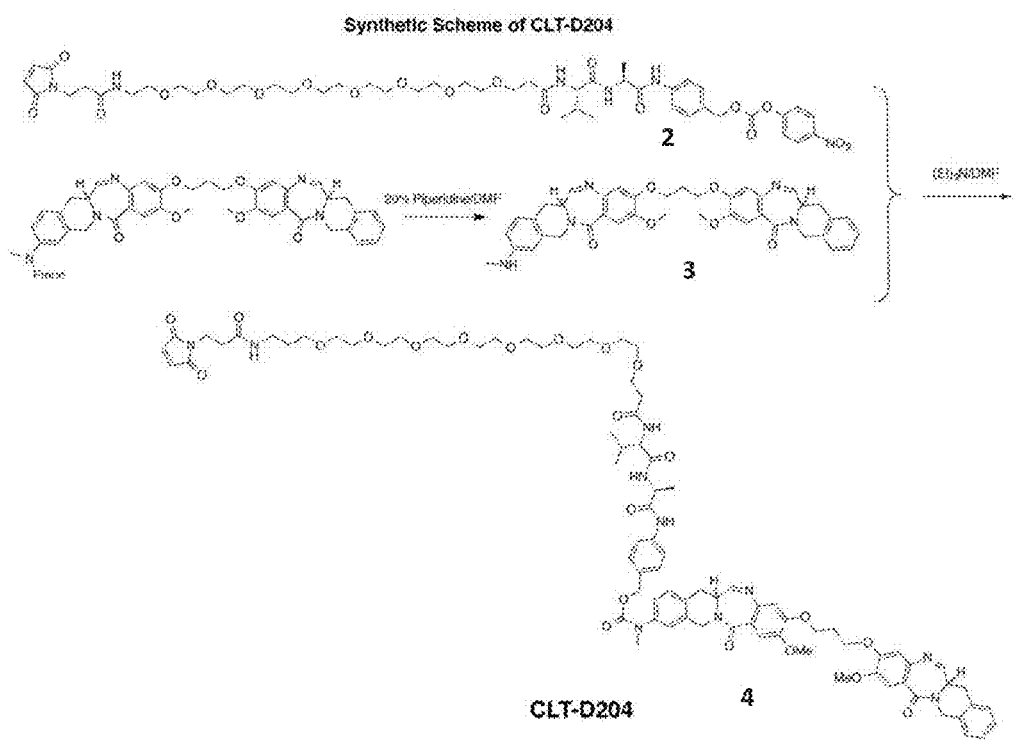

In FIGS. 9A and 9B, linker 2 bearing an activated nitrophenyl carbonate ester moiety is attached to dimer 3 through an amino group at position 5 of Formula I. The synthesis of the dimer 3 is shown in FIG. 9A and is similar to the general method described above, but specifically shows introduction of a nitro substituent in the isoquinolidinyl precursor which is reduced to an amino substituent and carried thru the remainder of the synthesis of the IQB ring system as a protected amino group. Dimer 3 is formed using one equivalent of the amino-bearing IQB moiety and one equivalent of an unsubstituted IQB moiety. FIG. 9B shows coupling of the linker 2 with the dimer 3 to form CLT-D204, an exemplar of a compound of formula I, having -L-$R_x$ at $R^5$, with malemide as the reactive moiety $R_x$.

II. Conjugates

Target binding moieties can be attached to an IQB of this disclosure using a variety of known cross-linking agents. Methods for covalent or non-covalent attachment of moieties to polypeptides are well known in the art. Such methods may include, but are not limited to, use of chemical cross-linkers, photoactivated cross-linkers and/or bifunctional cross-linking reagents. Exemplary methods for cross-linking molecules are disclosed in U.S. Pat. No. 5,603,872 and U.S. Pat. No. 5,401,511. Non-limiting examples of cross-linking reagents include glutaraldehyde, bifunctional oxirane, ethylene glycol diglycidyl ether, carbodiimides such as 1-ethyl-3-(3-dimethylaminopropyl) carbodiimide or dicyclohexylcarbodiimide, bisimidates, dinitrobenzene, N-hydroxysuccinimide ester of suberic acid, disuccinimidyl tartarate, dimethyl-3,3'-dithio-bispropionimidate, azidoglyoxal, N-succinimidyl-3-(2-pyridyldithio)propionate and 4-(bromoadminoethyl)-2-nitrophenylazide.

In some embodiments, the target binding moiety comprises an antibody. The term "antibody" refers to a polypeptide comprising a framework region from an immunoglobulin gene, or fragments thereof ("antibody fragment"), that specifically bind and recognize an antigen. Typically, the "variable region" contains the antigen-binding region of the antibody (or its functional equivalent) and is most critical in specificity and affinity of binding. An exemplary immunoglobulin (antibody) structural unit comprises a tetramer. Each tetramer is composed of two identical pairs of polypeptide chains, each pair having one "light" (about 25 kD) and one "heavy" chain (about 50-70 kD).

An "isotype" is a class of antibodies defined by the heavy chain constant region. Light chains are classified as either kappa or lambda. Heavy chains are classified as gamma, mu, alpha, delta, or epsilon, which in turn define the isotype classes, IgG, IgM, IgA, IgD and IgE, respectively. Antibodies can exist as intact immunoglobulins or as any of a number of well-characterized fragments that include specific antigen-binding activity, e.g., F(ab)'$_2$, or an Fab' monomer.

A "monoclonal antibody" refers to a clonal preparation of antibodies with a single binding specificity and affinity for a given epitope on an antigen. A "polyclonal antibody" refers to a preparation of antibodies that are raised against a single antigen, but with different binding specificities and affinities. A "chimeric antibody" is an antibody molecule in which (a) the constant region, or a portion thereof, is altered, replaced or exchanged so that the antigen binding site (variable region, CDR, or portion thereof) is linked to a constant region of a different or altered class, effector function and/or species, or an entirely different molecule which confers new properties to the chimeric antibody (e.g., an enzyme, toxin, hormone, growth factor, drug, etc.); or (b) the variable region, or a portion thereof, is altered, replaced or exchanged with a variable region having a different or altered antigen specificity (e.g., CDR and framework regions from different species).

A "humanized antibody" refers to an immunoglobulin molecule antibodies in which the antigen binding loops, i.e., CDRs, obtained from the $V_H$ and $V_L$ regions of a non-human antibody are grafted to a human framework sequence. Humanization, i.e., substitution of non-human CDR sequences for the corresponding sequences of a human antibody, can be performed following the methods described in, e.g., U.S. Pat. Nos. 5,545,806; 5,569,825; 5,633,425; 5,661,016; Riechmann et al., *Nature* 332:323-327 (1988); Marks et al., *Bio/Technology* 10:779-783 (1992); Morrison, *Nature* 368:812-13 (1994); Fishwild et al., *Nature Biotechnology* 14:845-51 (1996). Transgenic mice, or other organisms such as other mammals, may also be used to express humanized or human antibodies, as disclosed in U.S. Pat. No. 6,673,986.

The term "cysteine substituted antibody," as used herein, refers to an antibody comprising at least one non-naturally occurring constant region immunoglobulin amino acid residue that has been substituted with cysteine. A non-naturally occurring substitution is one that is not isotypic. In one embodiment, the substituted residues are heavy chain constant regions.

The terms "antigen", "antibody target", and like terms refer to a molecule, compound, or complex that is recognized by an antibody, i.e. can be specifically bound by the antibody. The antibody binds to an "epitope" on the antigen.

The terms "specific for," "specifically binds," and like terms refer to a molecule (e.g., antibody or antibody fragment) that binds to a target with at least 2-fold greater affinity than non-target compounds, e.g., at least any of 4-fold, 5-fold, 6-fold, 7-fold, 8-fold, 9-fold, 10-fold, 20-fold, 25-fold, 50-fold, or 100-fold greater affinity. For example, an antibody that specifically binds a primary antibody will typically bind the primary antibody with at least a 2-fold greater affinity than a non-primary antibody target (e.g., an antibody from a different species or of a different isotype, or a non-antibody target).

The term "captures" with respect to an antibody target (e.g., antigen, analyte, immune complex), typically indicates that an antibody binds a majority of the antibody targets in a pure population (assuming appropriate molar ratios). For example, an antibody that binds a given antibody target typically binds to at least ⅔ of the antibody targets in a solution (e.g., at least any of 75, 80, 85, 90, 91, 92, 93, 94, 95, 96, 97, 98, 99, or 100%). One of skill will recognize that some variability will arise depending on the method and/or threshold of determining binding.

Antibodies or fragments thereof may have functional groups which may be attractive targets for conjugation by compounds of formula I or II having a -L-Rx, as described above. A compound incorporating -L-Rx where maleimide is the reactive moiety may react with thiols of cysteine residues or disulfides formed from two cysteine side chains, where accessible on the antibody or fragment thereof. Alternatively, azido or iodoacetamidyl reactive moieties attached to a linker of the compound of formula I or II can also form a conjugate with a thiol of cysteine residues or disulfides formed intramolecularly. Disulfides can be specifically targeted by use of a compound of formula I or II having -L-Rx where the reactive moiety is a bis-sulfone, which can attach to both side chains at once.

Lysine side chains of antibodies or fragments thereof can be conjugated with a compound of formula I or II having a -L-$R_x$ where the reactive moiety is selected but not limited to isothiocyanate, succinimidyl ester, sulfonyl halide, carboxylic acid, sulfosuccinimidyl ester, 4-sulfotetrafluorophenyl ester, tetrafluorophenyl ester, and sulfodichlorophenol ester. When a carboxylic acid is the reactive moiety, the attachment reaction to the lysine side chain amino moiety is performed in the presence of a coupling reagent such as carbodiimide, which activates the carboxylic acid in situ.

Glutamine side chains may be targeted by an IQB having -L-$R_x$ where the reactive moiety is an aminoalkyl moiety. The amino moiety can be a substrate for modified transglutaminase to provide a glutaminyl conjugated IQB.

Aldehydes or ketones may be produced on a target binding agent such as an antibody or a fragment thereof, by oxidative treatments, often of the glycan portion of the antibody. Periodate or other oxidizing agents can be used to produce these carbonyl containing sites which may be targeted by a compound of formula I or II having a -L-Rx, where the reactive moiety is hydrazine, semihydrazide, carbohydrazide, or hydroxylamine.

Engineered functional moieties on the target binding agent, such as an antibody or fragment thereof, may also be conjugated by the compounds of formula of I or II having a -L-$R_x$. Selenocysteine may be incorporated ribosomally in engineered antibody fragments, which may afford a highly discriminating conjugation reaction with an IQB having a maleimide reactive moiety.

Azido or cyclooctyne moieties may be engineered into a target binding agent which can then permit the opposite reactive moiety, cyclooctynyl or azidyl reactive groups of an IQB having a -L-R, using copper-free click chemistry.

Introduction of unnatural amino acids via ribosomal incorporation can introduce a para-acetyl phenylalanine into a target binding agent. The acetyl group can be conjugated with an IQB having a -L-Rx where the reactive moiety is an aminooxy reactive group, providing an oxime conjugation product of the target binding agent. Another unnatural amino acid introduced via this process, can provide an azidyl-derivative of lysine which can be reacted with an IQB having a -L-$R_x$ where the reactive moiety is a cyclooctyne, and copper-free click chemistry is used.

These examples are in no way limiting; many other approaches to defined conjugation of a target binding agent such as an antibody or fragment thereof are envisioned by the use of the compounds of formula I and II having -L-$R_x$ to form conjugates of formula I and II having -L-$S_c$.

In some embodiments, an antibody-drug conjugate may have a structure of Formula III:

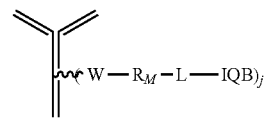

Formula III wherein:

is an antibody or antibody fragment;

W—$R_M$ is the linking moiety formed by W and $R_x$, where W is a moiety attached to a natural or unnatural amino acid residue of the antibody/antibody fragment and $R_x$ is a reactive moiety linking L-IQB to the antibody;

L is a linker, wherein L is a bond or is a moiety having 1-200 nonhydrogen atoms selected from C, N, O, S, or halogen, and optionally incorporates ether, oxo, carboxamidyl, urethanyl, branched, cyclic, unsaturated, heterocyclic, aromatic or heteroaromatic moieties;

j is a from 1 to 10; and,

IQB is a compound having a structure of Formula (I) or (II).

In some embodiments, an antibody-drug conjugate may have a structure of Formula III:

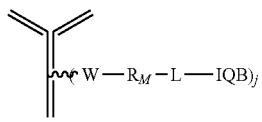

wherein:

is an antibody or antibody fragment;
W—$R_M$ is a linking moiety formed by W and $R_x$, wherein W is a moiety attached to a natural or unnatural amino acid residue of the antibody/antibody fragment and $R_x$ is a succinimidyl, maleimidyl, cylooctynyl, aminooxy, bisulfonyl, sulfonyl, or isothiocyanate moiety, such that W—$R_M$ is a disulfide, a thiolated succinimidyl, an amino substituted succinimidyl, a (cyclooctyl)-1,4 triazolyl, oxime substituted N-glycan, oxime, a substituted bis-sulfopropyl, a sulfonamidyl, an amide, or a thiocarbamate moiety; L is a linker, wherein L is a bond or is a moiety having 1-200 nonhydrogen atoms selected from C, N, O, S, or halogen, and optionally incorporates ether, oxo, carboxamidyl, urethanyl, branched, cyclic, unsaturated, heterocyclic, aromatic or heteroaromatic moieties; j is a number of 1 to 10; and, IQB is a compound having a structure of Formula (I) or (II):

alkenyl, $C_2$-$C_{10}$ alkynyl, a bond linked to linker L; each of $R^7$ and $R^{7'}$ is H; $R^8$ is: H, $NH_2$, $CO_2H$, or a bond linked to linker L, wherein the carbon to which $R^8$ is attached also has a hydrogen substituent; or an exo olefin having the structure

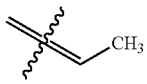 [SMILES: *=CC]

wherein the carbon to which $R^8$ is attached has no other substituent; X is: $C_{1-12}$ alkylene, optionally wherein the alkylene chain is interrupted by one or more hetero atoms selected from the group consisting of O, S, and NH; or —$(CH_2)_m$-Q-$(CH_2)_p$—, wherein m and p are each independently 0, 1 or 2; Q has a structure of formula:

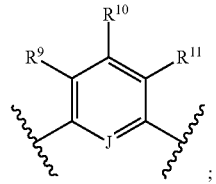

wherein each of $R^9$, $R^{10}$ and $R^{11}$ is H, $NH_2$, $CO_2H$, a bond linked to linker L; and J is CH or N; each of Y and Y' is independently O, S, or NH; each of Z and Z' is independently H, R, OH, OR, SH, SR, $NH_2$, or NHR, where each R is independently unsubstituted $C_1$-$C_{12}$ alkyl, substituted $C_1$-$C_{12}$ alkyl, unsubstituted $C_3$-$C_{20}$ heterocyclyl, substituted

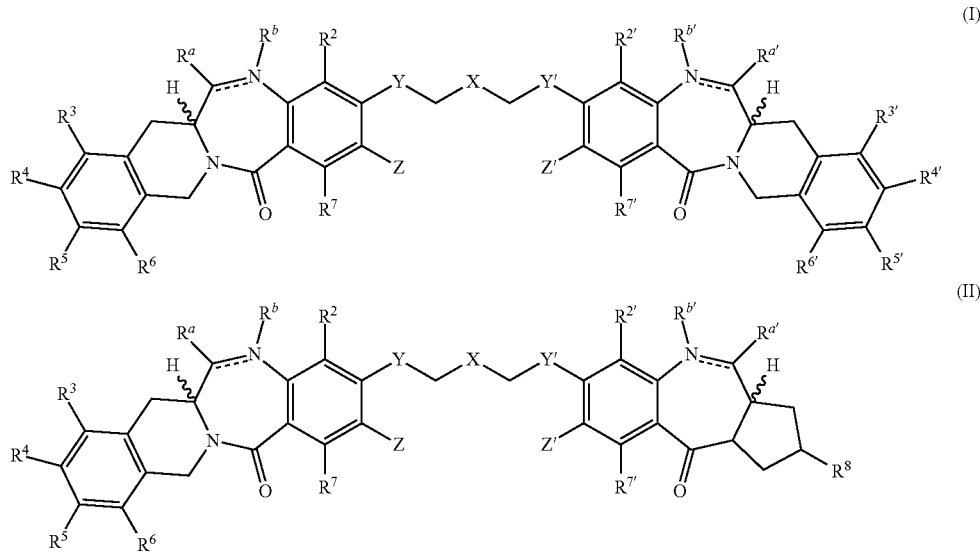

wherein: the dotted bond shown between —C($R^a$)— and —N($R^b$)— or —C($R^{a'}$)— and —N($R^{b'}$)— is independently a single bond or a double bond; each of $R^a$ and $R^{a'}$ is independently H, OH, or —O—P, where P is a protecting group; if present, each of $R^b$ and $R^{b'}$ is independently H, or a bond linked to linker L; $R^2$, $R^{2'}$, $R^3$, $R^{3'}$, $R^4$, $R^{4'}$, $R^6$ and $R^6$ are each independently selected from H, OH, $C_1$-$C_{10}$ alkyl, $C_2$-$C_{10}$ alkenyl or $C_2$-$C_{10}$ alkynyl; each of $R^5$ or $R^{5'}$ is independently $NH_2$, $CO_2H$, H, OH $C_1$-$C_{10}$ alkyl, $C_2$-$C_{10}$ $C_3$-$C_{20}$ heterocyclyl, unsubstituted $C_6$-$C_{20}$ aryl groups, and unsubstituted $C_6$-$C_{20}$ aryl groups; and wherein only one of $R^b$, $R^{b'}$, $R^5$, $R^{5'}$, $R^8$, $R^9$, $R^{10}$, and $R^{11}$ is a bond linked to linker L.

W may be attached directly or indirectly to the amino acid residue of the antibody. In some non-limiting examples, W may be a thiol of a cysteine residue, an amino group of a lysine residue, an azide group substituted on an amino acid, e.g. p-azidomethylphenylalanine, or an aldehyde or ketone substituted on an amino acid. Any of the moieties described above or any other suitable moiety as is known in the art may be used for reaction with a reactive moiety $R_x$ to introduce the IQB compound. In some other embodiments, W may be indirectly attached to the amino acid residue of the antibody, such as, but not limited to N-glycans engineered into the antibody as described herein.

$R_M$ is the portion of the reactive moiety $R_x$ that remains incorporated within the antibody-drug conjugate upon completion of the reaction between the W moiety and $R_x$. Some non-limiting examples of $R_x$ include a succinimidyl, maleimidyl, cylooctynyl, aminooxy, bisulfonfonyl, sulfonyl, or isothiocyanate moiety but may be any suitable $R_x$ as is known in the art. In one non-limiting example, $R_M$ may be a succimidyl moiety, substituted by a thio ether, which is the product of reacting a maleimidyl $R_x$ moiety with a thiol W moiety of a cysteine residue. $R_M$ may be any $R_M$ which is the product of any $R_x$ and suitable antibody substituent W as described herein, or any other suitable $R_M$ as is known in the art. In some embodiments, W—$R_M$ may be a disulfide, a thiolated succinimidyl, an amino substituted succinimidyl, a (cyclooctyl)-1, 4 triazolyl, oxime substituted N-glycan, oxime, a substituted bis-sulfopropyl, a sulfonamidyl, an amide, or a thiocarbamate moiety. The linker L may be any combination of elements as described herein.

The IQB of the antibody-drug conjugate may be any compound of Formula I or II as described herein. In one embodiment, the IQB compound is a compound of the formula:

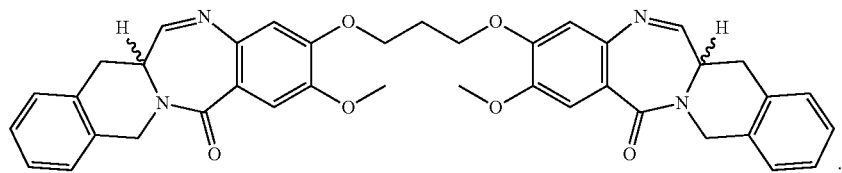

1
CLT-D201

The —W—$R_M$-L-IQB moiety attached to the antibody may have any combination of W moiety attached directly or indirectly to the antibody; any RM resulting from the reaction of any suitably cross-reactive Rx with W; any linker L connecting the RM to the IQB compound and any IQB as described herein.

In other embodiments, IQB is a moiety having the structure:

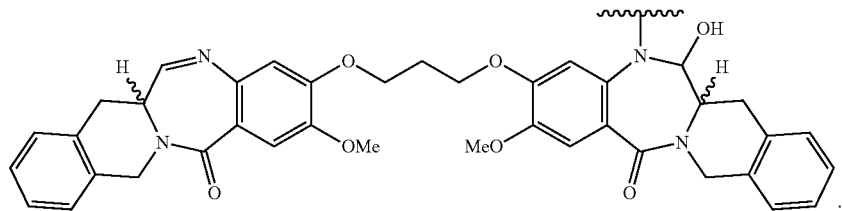 [SMILES: *N1c2cc(OCCCOc3cc4c(cc3OC)C(=O)N3Cc5ccccc5CC3C=N4)c(OC)cc2C(=O)N2Cc3ccccc3CC2C1O]

In some embodiments, a —W—$R_M$-L-IQB may have a structure of Formula IV:

Formula IV

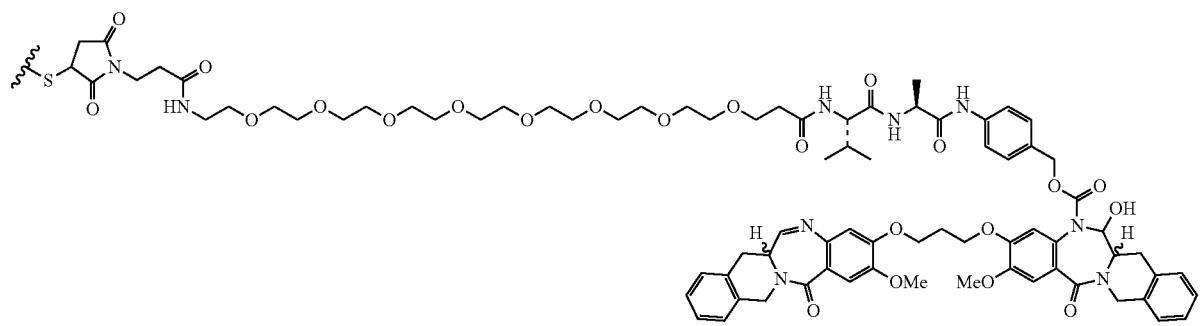

The —W—R$_M$-L-IQB moiety may be attached to a thiol W group of a non-natural cysteine. There may be 1 or more of the —W—R$_M$-L-IQB moieties attached to the antibody or antibody fragment. In some embodiments there may be from 1 to about 3-W—R$_M$-L-IQB moieties attached to the antibody. In other embodiments there may be more than 1 but less than about 2-W—R$_M$-L-IQB moieties. The number of —W—R$_M$-L-IQB moieties may be a fractional number as the population of antibodies being conjugate with the —W—R$_M$-L-IQB moieties may not fully react or may react at other sites besides the non-natural cysteine residue. In some embodiments, the antibody or antibody fragment is anti-CLL1. In some embodiments, the antibody or antibody fragment is anti-CLL1 and IQB is a moiety having the structure:

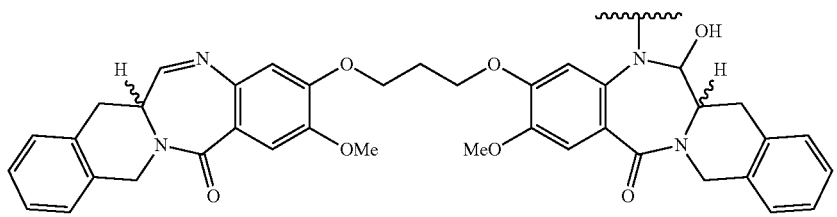

In some embodiments, the antibody-drug conjugate is the compound of formula III, wherein the antibody or antibody fragment is anti-CLL1; W—R$_M$ is a thiolated succinimidyl; and IQB is a moiety having the structure:

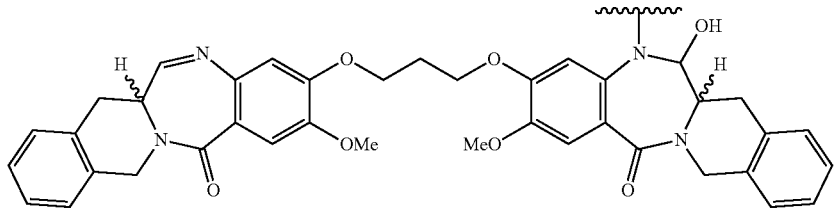

The antibody of the conjugate may be any antibody or antibody fragment as described herein. The antibody/antibody fragment may bind specifically to cancerous myeloproliferative cells and/or leukemic cancer stem cells and may not bind to normal hematopoietic stem cells.

III. Pharmaceutical Compositions

Dosage forms containing isoquinolidinobenzodiazepines as the active ingredient may be advantageously used to treat or prevent proliferative diseases. The dosage forms may be administered or applied singly, or in combination with other agents. The formulations may also deliver an isoquinolidinobenzodiazepine to a subject in combination with another pharmaceutically active agent, including another isoquinolidinobenzodiazepines.

The formulations, for human medical use, of the present disclosure comprise an active ingredient in association with a pharmaceutically acceptable carrier therefor and optionally other therapeutic ingredient(s). The carrier(s) must be "acceptable" in the sense of being compatible with the other ingredients of the formulations and not deleterious to the recipient thereof.

The terms "effective amount," "effective dose," "therapeutically effective amount," etc. refer to that amount of the therapeutic agent sufficient to ameliorate a disorder, as described above. For example, for the given parameter, a therapeutically effective amount will show an increase or decrease of therapeutic effect at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosage forms can be prepared for mucosal (e.g., nasal, sublingual, vaginal, buccal, or rectal), parenteral (e.g., subcutaneous, intravenous, intramuscular, or intraarterial injection, either bolus or infusion), oral, or transdermal administration to a subject. Examples of dosage forms include, but are not limited to: dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a subject, including suspensions (e.g., aqueous or non-aqueous liquid suspensions, oil-in-water emulsions, or a water-in-oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject.

Injectable (e.g., intravenous) compositions can comprise a solution of the antibody or antibody-targeted composition suspended in an acceptable carrier, such as an aqueous carrier. Any of a variety of aqueous carriers can be used, e.g., water, buffered water, 0.4% saline, 0.9% isotonic saline, 0.3% glycine, 5% dextrose, and the like, and may include glycoproteins for enhanced stability, such as albumin, lipoprotein, globulin, etc. Often, normal buffered saline (135-150 mM NaCl) will be used. The compositions can contain pharmaceutically acceptable auxiliary substances to approximate physiological conditions, such as pH adjusting and buffering agents, tonicity adjusting agents, wetting agents, e.g., sodium acetate, sodium lactate, sodium chloride, potassium chloride, calcium chloride, sorbitan monolaurate, triethanolamine oleate, etc. In some embodiments, the composition can be formulated in a kit for intravenous administration.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, granules, and tablets. In the practice of the present invention, compositions can be administered, for example, by intravenous infusion, topically, intraperitoneally, intravesically, or intrathecally. Parenteral administration and intravenous administration are the preferred methods of administration. The formulations of targeted compositions can be presented in unit-dose or multi-dose sealed containers, such as ampoules and vials.

The pharmacologically active compounds of the disclosure are useful in the manufacture of pharmaceutical compositions comprising an effective amount thereof in conjunction or admixture with the excipients or carriers suitable for either enteral or parenteral application. Preferred are tablets and gelatin capsules comprising the active ingredient together with one or more of the following: (a) diluents, such as lactose, dextrose, sucrose, mannitol, sorbitol, cellulose, glycine and the like; (b) lubricants, such as silica, talcum, stearic acid, its magnesium or calcium salt, polyethyleneglycol and the like; for tablets also; (c) binders, such as magnesium aluminum silicate, starch paste, gelatin, tragacanth, methylcellulose, sodium carboxymethyl-cellulose or polyvinylpyrrolidone and the like; and, if desired, (d) disintegrants, such as effervescent mixtures and the like; and (e) absorbents, colorants, flavors, and sweeteners and the like.

The formulations may conveniently be presented in unit dosage form and may be prepared by any of the methods well-known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Said pharmaceutical compositions may be sterilized and/or contain adjuvants, such as preserving, stabilizing, wetting or emulsifying agents, solution promoters, salts for regulating the osmotic pressure, and/or buffers. In addition, they may also contain other therapeutically valuable substances. Said compositions are prepared according to conventional mixing, granulating, or coating methods, respectively, and contain about 0.1 to 75%, preferably about 1 to 50%, of the active ingredient.

The concentration of the active agent in the formulation can vary a great deal, and will depend on a variety of factors, including the disease or condition to be treated, the nature and activity of the active agent, the desired effect, possible adverse reactions, the ability and speed of the active agent to reach its intended target, and other factors within the particular knowledge of the subject and physician. The formulations will typically contain on the order of about 0.5 wt % to 50 wt % active agent, preferably about 0.5 wt % to 5 wt % active agent, optimally about 5 wt % to 20 wt % active agent.

An IQB conjugate can also be formulated to provide more than one active compound, e.g., additional chemotherapeutic or cytotoxic agents, cytokines, or growth inhibitory agents. The active ingredients may also prepared as sustained-release preparations (e.g., semi-permeable matrices of solid hydrophobic polymers (e.g., polyesters, hydrogels (for example, poly (2-hydroxyethyl-methacrylate), or poly (vinylalcohol)) or polylactides). The antibodies and immunocongugates can be entrapped in a nanoparticle prepared, for example, by coacervation techniques or by interfacial polymerization, for example, hydroxymethylcellulose or gelatin microcapsules and poly-(methylmethacylate) microcapsules, respectively, in colloidal drug delivery systems (for example, liposomes, albumin microspheres, microemulsions, nano-particles and nanocapsules) or in macroemulsions.

IQBs of this disclosure may take the form of a pharmaceutically acceptable salt, e.g., a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, butyric acid, propionic acid, hexanoic acid, cyclopentanepropionic acid, glycolic acid, pyruvic acid, lactic acid, valeric acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like, made by conventional chemical means; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like, made by conventional chemical means.

IV. Methods of Use

A. Treatment of Proliferative Disease

Isoquinolidinobenzodiazepines of this disclosure inhibit cell growth (proliferation), and thus are useful in pharmaceutical compositions to treat a subject, e.g., a vertebrate, e.g., a mammal, e.g., a human. IQBs can be administered alone or as conjugates wherein they are conjugated to a cell targeting agent such as an antibody.

"Subject," "patient," "individual" and like terms are used interchangeably and refer to, except where indicated, mammals such as humans and non-human primates, as well as rabbits, rats, mice, goats, pigs, and other mammalian species. The term does not necessarily indicate that the subject has been diagnosed with a particular disease, but typically "patient" refers to an individual under medical supervision. A patient can be an individual that is seeking treatment, monitoring, adjustment or modification of an existing therapeutic regimen, etc. A "cancer patient" can refer to an individual that has been diagnosed with cancer, is currently following a therapeutic regimen, or is at risk of recurrence, e.g., after surgery to remove a tumor. In some embodiments, the cancer patient has been diagnosed with cancer and is a candidate for therapy. Cancer patients can include individuals that have not received treatment, are currently receiving treatment, have had surgery, and those that have discontinued treatment.

The terms "therapy," "treatment," and "amelioration" refer to any reduction in the severity of symptoms. In the case of treating cancer, treatment can refer to, e.g., reducing tumor size, number of cancer cells, growth rate, metastatic activity, reducing cell death of non-cancer cells, reduced nausea and other chemotherapy or radiotherapy side effects, etc. In the case of treating an inflammatory condition, the treatment can refer to, e.g., reducing blood levels of inflammatory cytokines, pain, swelling, recruitment of immune cells, etc. As used herein, the terms "treat" and "prevent" are not intended to be absolute terms. Treatment and prevention can refer to any delay in onset, amelioration of symptoms, improvement in patient survival, increase in survival time or rate, etc. Treatment and prevention can be complete (undetectable levels of neoplastic cells) or partial, such that fewer neoplastic cells are found in a patient than would have occurred without the present invention. The effect of treatment can be compared to an individual or pool of individuals not receiving the treatment, or to the same patient prior to treatment or at a different time during treatment. In some aspects, the severity of disease is reduced by at least 10%, as compared, e.g., to the individual before administration or to a control individual not undergoing treatment. In some aspects the severity of disease is reduced by at least 25%, 50%, 75%, 80%, or 90%, or in some cases, no longer detectable using standard diagnostic techniques.

Compositions of this disclosure are useful in the treatment of proliferative diseases such as cancer. "Cancer", "tumor," "transformed" and like terms include precancerous, neoplastic, transformed, and cancerous cells, and can refer to a solid tumor, or a non-solid cancer (see, e.g., Edge et al. AJCC Cancer Staging Manual (7th ed. 2009); Cibas and Ducatman Cytology: Diagnostic principles and clinical correlates (3rd ed. 2009)). Cancer includes both benign and malignant neoplasms (abnormal growth). "Transformation" refers to spontaneous or induced phenotypic changes, e.g., immortalization of cells, morphological changes, aberrant cell growth, reduced contact inhibition and anchorage, and/or malignancy (see, Freshney, Culture of Animal Cells a Manual of Basic Technique (3rd ed. 1994)). Although transformation can arise from infection with a transforming virus and incorporation of new genomic DNA, or uptake of exogenous DNA, it can also arise spontaneously or following exposure to a carcinogen.

The term "cancer" can refer to carcinomas, sarcomas, adenocarcinomas, lymphomas, leukemias, solid and lymphoid cancers, etc. Examples of different types of cancer include, but are not limited to, lung cancer (e.g., non-small cell lung cancer or NSCLC), ovarian cancer, prostate cancer, colorectal cancer, liver cancer (i.e., hepatocarcinoma), renal cancer (i.e., renal cell carcinoma), bladder cancer, breast cancer, thyroid cancer, pleural cancer, pancreatic cancer, uterine cancer, cervical cancer, testicular cancer, anal cancer, pancreatic cancer, bile duct cancer, gastrointestinal carcinoid tumors, esophageal cancer, gall bladder cancer, appendix cancer, small intestine cancer, stomach (gastric) cancer, cancer of the central nervous system, skin cancer, choriocarcinoma; head and neck cancer, blood cancer, osteogenic sarcoma, fibrosarcoma, neuroblastoma, glioma, melanoma, B-cell lymphoma, non-Hodgkin's lymphoma, Burkitt's lymphoma, Small Cell lymphoma, Large Cell lymphoma, myelodisplastic syndromes (MDS), monocytic leukemia, myelogenous leukemia, acute lymphocytic leukemia, acute myelocytic leukemia (AML), chronic myeloid leukemia (CML), and multiple myeloma. In some embodiments, the compositions and methods of the present invention are useful for treating cancer.

Cancers that can be targeted include, for example, leukemia (e.g., acute lymphoblastic leukemia (ALL), acute myeloid leukemia (AML), chronic lymphocytic leukemia (CLL) and chronic myeloid leukemia (CML)), breast cancer, prostate cancer, colorectal cancer, brain cancer, esophageal cancer, head and neck cancer, bladder cancer, gynecological cancer, liposarcoma, and multiple myeloma. In some embodiments, the target binding domain within the CAR of the disclosed disclosure is capable of binding any of a broad group of targets, including but not limited to, GPR114, CLL-1, IL1RAP, TIM-3, CD19, CD20, CD22, ROR1, mesothelin, CD33, CD123/IL3Ra, c-Met, PSMA, prostatic acid phosphatase (PAP), CEA, CA-125, Muc-1, AFP, Glycolipid F77, EGFRvIII, GD-2, NY-ESO-1 TCR, tyrosinase, TRPI/gp75, gp100/pmeI-17, Melan-A/MART-1, Her2/neu, WT1, EphA3, telomerase, HPV E6, HPV E7, EBNA1, BAGE, GAGE and MAGE A3 TCRSLITRK6, ENPP3, Nectin-4, CD27, SLC44A4, CAIX, Cripto, CD30, MUC16, GPNMB, BCMA, Trop-2, Tissue Factor (TF), CanAg, EGFR, αv-integrin, CD37, Folate Receptor, CD138, CEACAM5, CD56, CD70, CD74, GCC, 5T4, CD79b, Steap1, Napi2b, Lewis Y Antigen, LIV, c-RET, DLL3, EFNA4, Endosialin/CD248 and other targets known to one of skill in the art.

A "cancer target" or "cancer marker" is a molecule that is differentially expressed or processed in cancer, e.g., on a cancer cell or in the cancer milieu. Exemplary cancer targets are cell surface proteins such as IL1RAP (also, e.g., cell adhesion molecules and receptors), intracellular receptors, hormones, and molecules such as proteases that are secreted by cells into the cancer milieu. Markers for specific cancers are known in the art, e.g., MUC1 expression on colon and colorectal cancers, bombesin receptors in lung cancer, and prostate specific membrane antigen (PSMA) on prostate cancer.

The terms "overexpressed" or "upregulated" interchangeably refer to a protein or nucleic acid, generally a biomarker, that is transcribed or translated at a detectably greater than control level. The term includes overexpression due to transcription, post transcriptional processing, translation, post-translational processing, cellular localization (e.g., organelle, cytoplasm, nucleus, cell surface), and RNA and protein stability. Overexpression can be detected using conventional techniques for detecting biomarkers, whether mRNA (i.e., RT-PCR, hybridization) or protein (i.e., flow cytometry, imaging, ELISA, immunohistochemical techniques). Overexpression can be at least any of 10%, 20%, 30%, 40%, 50%, 60%, 70%, 80%, 90% or more in comparison to a normal cell.

In some embodiments, the cancer target can be associated with a certain type of cancer cell, e.g., leukemia, myeloma, lymphoma, AML, CML, non-small cell lung cancer cells, prostate cancer, colorectal cancer, breast cancer or ovarian cancer. A cell type specific target is typically expressed at levels at least 2 fold greater in that cell type than in a reference population of cells. In some embodiments, the cell type specific marker is present at levels at least 3, 4, 5, 6, 7, 8, 9, 10 20, 50, 100, or 1000 fold higher than its average expression in a reference population. Thus, the target can be detected or measured to distinguish the cell type or types of interest from other cells.

A cancer stem cell (CSC) is a cell found in a tumor or blood cancer that can give rise to the cells that make up the bulk of the cancer. The CSC can also be self-renewing, similar to a normal (non-cancer) stem cell. CSCs can thus mediate metastasis by migrating to a non-tumor tissue in an individual and starting a "new" tumor. CSCs make up a very small percentage of any given cancer, depending on the stage that the cancer is detected. For example, the average frequency of CSCs in a sample of AML cells is believed to be about 1:10,000.

Hematopoietic CSCs can be identified as CD34+, similar to normal hematopoietic stem cells (HSCs). Other CSC associated markers include CD44 (breast), CD133 (glial cancers), and Notch (e.g., myelomas and neuroblastoma).

One non-limiting example of a cancer target for which the IQBs described herein can be incorporated within an antibody-drug conjugate, is C type Lectin Like molecule ("CLL-1"). CLL-1 is expressed on AML blasts and LSCs, but not on normal hematopoietic stem cells. CLL-1 is expressed on leukemic cells within both the bone marrow and blood compartments. The target antigen is present across all AML French American British (FAB) classifications and cytogenetic risk categories and is expressed independent of FLT-3 status. The target is expressed in de novo and recurrent disease states. Expression of CLL-1 antigen in combination with multidrug resistance (MDR) is associated with poor disease prognosis and greater probability of relapse.

In addition to being expressed in AML, CLL-1 is expressed in MDS and other myeloproliferative disorders (e.g., polycythemia vera, essential thrombocythemia and polymyelofibrosis).

C-type Lectin-Like molecule 1 (CLL-1), also known as CLEC12A, DCAL-2, and MICL, is a type II membrane protein (ITIM domain-TM domain-stalk domain-lectin-like domain). The extracellular domain of CLL-1 is highly glycosylated, and it is expressed exclusively in cells of myeloid lineage.

The nucleotide and protein sequences of CLL-1 are known for many species. For example, the human sequences can be found at Genbank accession number AF247788.1 and Uniprot accession number Q5QGZ9. For the human CLL-1 protein, the extracellular domain comprises approximately amino acids 65-265, the transmembrane domain comprises approximately amino acids 44-64, and the cytoplasmic domain comprises approximately amino acids 1-43. The stalk domain of human CLL-1 spans amino acids 65-139, and the C lectin domain spans amino acids 140-249. One of skill will understand that CLL-1 variants (e.g., species homologs, allelic variants, etc.) can be optimally aligned, e.g., for identification of conserved residues and domains.

The terms "CLL-1 specific antibody," "anti-CLL-1 antibody," "CLL-1 antibody," "CLL-1 ADC" and "anti-CLL-1" are used synonymously herein to refer to an antibody (or antibody conjugate, depending on context) that specifically binds to CLL-1, including variously glycosylated forms of CLL-1. The CLL-1 antibodies described herein specifically bind the CLL-1 polypeptide expressed, e.g., on the surface of certain cancer cells, but not to HSCs. As discussed in more detail below, the present anti-CLL-1 antibodies can bind CLL-1 expressing cells, bind a larger percentage of AML cells compared to other AML-targeting antibodies, inhibit AML cell proliferation, and mediate their destruction.

A "CLL-1 associated disorder" (or CLL-1 related disorder, CLL-1 disorder, CLL-1 related condition or disease, etc.) refers to conditions and diseases correlated with elevated or reduced cell surface expression of CLL-1 as compared to CLL-1 expression in a standard control (e.g., a normal, non-disease, non-cancer cell). Elevated CLL-1 levels are associated with cancer cells, in particular, leukemias such as AML (acute myelogenous leukemia), MDS (myelodysplastic syndrome), and CML (chronic myelogenous leukemia), and in hematopoietic CSCs (e.g., LSCs).

One non-limiting example of an antibody that may be useful to target AML and cancer stem cells of involved lineages is an anti-CLL-1 antibody, and more specifically, a humanized anti-CLL1 antibody. Such antibodies are described, for example, in US 2013/0295118 and provisional application 62/359,100, both incorporated herein by reference.) In some embodiments, the anti-CLL-1 antibody is optionally a chimeric (e.g., humanized) antibody and comprises light chain and heavy chain variable regions of SEQ ID NO: 1 and 2, respectively. In certain embodiments, the antibody can include substitutions of a cysteine residue for another residue. Compositions of this disclosure can be attached to the antibodies through the cysteine residue. In one example, a serine residue at position 239 is substituted with cysteine (S239C). More than one IQB compound may be incorporated into antibodies so modified. In some embodiments, the number of IQB compounds attached to an antibody may be any number in the range from 1 to about 10, or any number in between, including a fractional number. In some embodiments, the number of IQB compounds attached to the antibody is in the range from 1 to about 3. Such an antibody incorporating the IQBs described herein have been found to be effective in in-vitro and in-vivo applications as described below.

B. Dosage

The amount of isoquinolidinobenzodiazepines that will be effective in the treatment or prevention of proliferative disorders in a subject will depend on the specific nature of the condition, and can be determined by standard clinical techniques known in the art. In addition, in vitro or in vivo assays may optionally be employed to help identify optimal dosage ranges. The specific dose level for any particular individual will depend upon a variety of factors including the relative activity of the isoquinolidinobenzodiazepines, the age, body weight, general physical and mental health, genetic factors, environmental influences, sex, diet, time of administration, route of administration, rate of excretion, and the severity of the particular problem being treated.

The terms "dose" and "dosage" are used interchangeably herein. A dose refers to the amount of active ingredient given to an individual at each administration. For the present invention, the dose can refer to the concentration of the antibody or associated components, e.g., the amount of therapeutic agent or dosage of radiolabel. The dose will vary depending on a number of factors, including frequency of administration; size and tolerance of the individual; severity of the condition; risk of side effects; the route of administration; and the imaging modality of the detectable moiety (if present). One of skill in the art will recognize that the dose can be modified depending on the above factors or based on therapeutic progress. The term "dosage form" refers to the particular format of the pharmaceutical, and depends on the route of administration. For example, a dosage form can be in a liquid, e.g., a saline solution for injection.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of benefit and/or side effects). Controls can be designed for in vitro applications. One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

In certain embodiments, the isoquinolidinobenzodiazepines of the disclosure will be conjugated to a target binding moiety, such as an antibody. The target binding moiety can be specific to targets on cells targeted for elimination in order to treat a subject suffering from a condition caused by the presence of such cells. The target can be any biomolecule on a target cell. Target cells can include cancer cells. Therefore, the target can comprise, for example, a polypeptide expressed on a cancer cell, e.g., a tumor-associated antigen. In another embodiment, the target binding moiety can be a chimeric antigen receptor ("CAR") that can bind an antigen determinant comprising amino acids within the extracellular domain of a tumor-associated antigen, a viral antigen or a viral associated antigen or a fragment of such a polypeptide.

Suitable dosage ranges for oral administration are dependent on the potency of the particular isoquinolidinobenzodiazepine or isoquinolidinobenzodiazepine antibody conjugates, but are generally about 0.001 mg to about 500 mg of drug per kilogram body weight, preferably from about 0.1 mg to about 200 mg of drug per kilogram body weight, and more preferably about 1 to about 100 mg/kg-body wt. per day. Dosage ranges may be readily determined by methods known to the skilled artisan. The amount of active ingredient that may be, for instance, combined with carrier materials to produce a single dosage form will vary depending upon the subject treated and the particular mode of administration. Dosage unit forms will generally contain between about 1 mg to about 500 mg of active ingredient.

Administration can be periodic. Depending on the route of administration, the dose can be administered, e.g., once every 1, 3, 5, 7, 10, 14, 21, or 28 days or longer (e.g., once every 2, 3, 4, or 6 months). In some cases, administration is more frequent, e.g., 2 or 3 times per day. The subject can be monitored to adjust the dosage and frequency of administration depending on therapeutic progress and any adverse side effects, as will be recognized by one of skill in the art.

Thus in some embodiments, additional administration is dependent on subject progress, e.g., the subject is monitored between administrations. For example, after the first administration or round of administrations, the subject can be monitored for rate of tumor growth, recurrence (e.g., in the case of a post-surgical subject), or general disease-related symptoms such as weakness, pain, nausea, etc.

C. Methods of Administration

The antibody conjugate compositions may be administered by any other convenient route, for example, by infusion or bolus injection, or by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer the antibody conjugate compositions. Methods of administration include, but are not limited to, intradermal, intramuscular, intraperitoneal, intravenous, subcutaneous, intranasal, epidural, intranasal, and intracerebral.

The amount of isoquinolidinobenzodiazepine antibody conjugates that will be effective in the treatment or prevention of proliferative disorders in a subject will depend on the specific nature of the condition, and can be determined by standard clinical techniques known in the art. In addition, in vitro or in vivo assays may optionally be employed to help identify optimal dosage ranges. The specific dose level for any particular individual will depend upon a variety of factors including the relative activity of the isoquinolidinobenzodiazepine antibody conjugates, the age, body weight, general physical and mental health, genetic factors, environmental influences, sex, diet, time of administration, route of administration, rate of excretion, and the severity of the particular problem being treated.

The IQB or IQB conjugate can be administered by injection or infusion through any suitable route including but not limited to intravenous, subcutaneous, intramuscular or intraperitoneal routes. An example of administration of a pharmaceutical composition includes storing the composition at 10 mg/ml in sterile isotonic aqueous saline solution for injection at 4° C., and diluting it in either 100 ml or 200 ml 0.9% sodium chloride for injection prior to administration to the subject. The composition is administered by intravenous infusion over the course of 1 hour at a dose of between 0.2 and 10 mg/kg. In other embodiments, the composition is administered by intravenous infusion over a period of between 15 minutes and 2 hours. In still other embodiments, the administration procedure is via sub-cutaneous bolus injection.

The following examples are offered by way of illustration and not by way of limitation.

EXAMPLES

General Methods used in Examples 1-3: $^1$H NMR spectra were recorded on a Bruker Avance III 500 MHz NMR instrument and/or on a Varian Inova 300 MHz spectrometer. Chromatographic purities were determined on an Agilent 1100 Series LC/MS system using a Merck Chromolith RP-18e analytical HPLC column (monolithic, 50×2 mm) and the following analytical HPLC method: injection volume 5-15 µL; flow rate 1.0 mL/min; 5-95% acetonitrile in water (0.05% AcOH as modifier) over 5 minutes; Agilent diode array detector at A=280, 254 and 220 nm; room temperature. For all analyses, the mass spectrometry system used was an Agilent 1100 and/or 1200 LC/MSD (SL).

All normal phase purifications were performed using RediSep® Rf Gold columns (Teledyne ISCO; Lincoln, Nebr.) in concert with a Teledyne ISCO CombiFlash Rf 200 and using a solvent gradient comprised of A→B. The specific identity of A and B, and the gradient used, will be indicated for each unique example below.

All reverse phase purifications were performed using RediSep® Rf reversed phase C18 columns (Teledyne ISCO) in concert with a Teledyne ISCO CombiFlash Rf 200 and using a solvent gradient comprised of A: $H_2O$ (0.05% AcOH) and B: acetonitrile (0.05% AcOH). The specific size of column used and particular solvent gradient will be indicated for each unique example below.

The water used in the following experiments was ultrapure (18 MΩ), purified via Veolia ELGA PURELAB flex purification system (ELGA LLC; Woodridge, Ill.).

Example 1

Synthesis of CLT-D201

2-(4-Benzyloxy-5-methoxy-2-nitro-benzoyl)-1,2,3,4-tetrahydro-isoquinoline-3-carboxylic acid methyl ester (6)

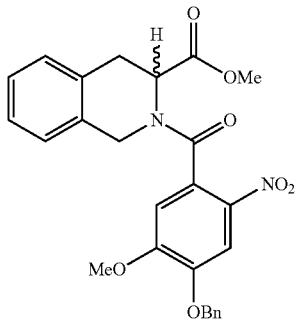

Referring to FIG. 3, to an argon-purged solution of 4-benzyloxy-5-methoxy-2-nitro-benzoic acid (8) (4.00 g, 13.2 mmol) in tetrahydrofuran (THF) (16 mL) at 22° C., oxalyl chloride (1.68 mL, 19.8 mmol) was added, followed by dimethyl formamide (DMF) (0.2 mL). The reaction was stirred at 22° C. overnight, under an atmosphere of Ar. The mixture was then concentrated in vacuo, re-dissolved in THF and concentrated again to provide the crude acid chloride.

In a separate flask, 1,2,3,4-tetrahydro-isoquinoline-3-carboxylic acid methyl ester (7) (3.78 g, 19.8 mmol) and triethylamine (4.60 mL, 33.0 mmol) were purged with Ar, dissolved in dichloromethane (DCM) (20 mL), and cooled to −30° C. To this mixture, under Ar, the crude acid chloride in DCM (15 mL) was added dropwise while keeping the internal temperature of the mixture ≤−20° C. The cold bath was then removed and the reaction was allowed to stir for 3 hr while warming to ambient temperature, at which point the reaction was complete. The mixture was then concentrated and partitioned between ethyl acetate (EtOAc) and H$_2$O. The reaction was extracted with EtOAc (3×50 mL) and the combined organics were then washed with H$_2$O (50 mL), dried over anhydrous magnesium sulfate, filtered and concentrated. The resulting residue was partially purified via column chromatography (0→10% methanol (MeOH) in DCM) to provide impure (3) as a yellow foam (4.34 g, 69% yield, 9.11 mmol) in >85% purity by LC/MS. LC/MS: retention time 3.39 min. LC/MS (ES$^+$) calc. for C$_{26}$H$_{25}$N$_2$O$_7$: [M+H]$^+$ 477. found 477.

2-Benzyloxy-3-methoxy-11,11a-dihydro-6H,13H-5a,13-diaza-benzo[4,5]cyclohepta[1,2-b]naphthalene-5,12-dione (5)

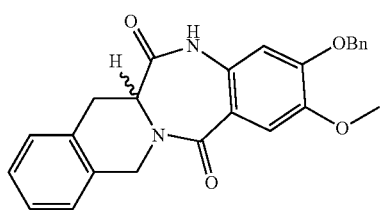

To a solution of impure 2-(4-benzyloxy-5-methoxy-2-nitro-benzoyl)-1,2,3,4-tetrahydro-isoquinoline-3-carboxylic acid methyl ester (6) (3.3 g, 6.9 mmol) in MeOH (230 mL), a spatula tips of Raney® Ni was added. The mixture was then heated to reflux and hydrazine hydrate (4.3 mL, 139 mmol) in MeOH (40 mL) was added dropwise. Rapid effervescence was observed upon addition of hydrazine. Once the addition of hydrazine was completed, no further effervescence was observed upon further addition of Raney Ni. The reaction was then refluxed an additional 30 min and the reaction was judged complete by LC/MS. (Note: Longer reaction times lead to undesired debenzylation). The reaction was removed from heat, filtered through celite, and washed with MeOH. The filtrate was concentrated in vacuo, and azeotroped with DCM. The resulting solids were triturated with DCM to afford a white precipitate. The remaining filtrate residue was purified via column chromatography (0→10% MeOH in DCM). The washed filter cake still contained product, and was suspended in 100 mL of 1:1 acetonitrile (ACN)/H$_2$O, the solids were filtered through fresh celite and the filtrate was lyophilized. All three batches of clean material (triturated precipitate, lyophilized material, and the clean fraction from column chromatography) were combined to afford (4) as a white crystalline solid (2.26 g, 79% yield, 5.44 mmol). $^1$H NMR (500 MHz, CDCl$_3$): δ 7.43-7.36 (m, 9H), 7.34-7.22 (m, 2H), 6.37 (bs, 1H), 5.18 (bs, 2H), 5.12 (d, J=15.1 Hz, 1H), 4.48 (d, J=15.1 Hz, 1H), 4.19 (t, J=6.8 Hz, 1H), 3.92 (s, 3H), 3.49 (dd, J=15.4, 7.1 Hz, 1H), 3.00 (dd, J=15.4, 6.1 Hz, 1H). LC/MS: retention time 2.92 min. (ES$^+$) calc. for C$_{25}$H$_{23}$N$_2$O$_4$: [M+H]$^+$ 415. found 415.

2-Benzyloxy-3-methoxy-13-(2-trimethylsilanyl-ethoxymethyl)-11,11a-dihydro-6H,13H-5a,13-diaza-benzo[4,5]cyclohepta[1,2-b]naphthalene-5,12-dione (4)

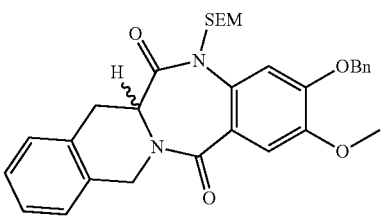

To an argon-purged solution of 2-benzyloxy-3-methoxy-11,11a-dihydro-6H,13H-5a,13-diaza-benzo[4,5]cyclohepta[1,2-b]naphthalene-5,12-dione (5) (2.26 g, 5.44 mmol) in THF (60 mL), cooled to −40° C. in a dry ice/ACN bath, was added n-butyllithium (nBuLi)(4.25 mL of a 1.6 M solution in hexane, 6.80 mmol) drop wise. The mixture was allowed to stir at −40° C. for 1 hr, then a solution of 2-trimethylsilyl)ethoxymethyl chloride (1.20 mL, 6.80 mmol) in 20 mL THF was added dropwise. The resulting mixture was allowed to slowly warm up to ambient temperature overnight. The reaction was then concentrated in vacuo and the residue was partitioned between EtOAc and H$_2$O. The reaction was extracted with EtOAc (3×50 mL) and the combined organics were then washed with brine (50 mL), dried over anhydrous magnesium sulfate, filtered and concentrated. The resulting residue was purified via column chromatography (0→50% EtOAc in Hex) to provide (4) as a yellow foam (1.99 g, 67% yield, 3.66 mmol). $^1$H NMR (500 MHz, CDCl$_3$): δ 7.45-7.42

(m, 2H), 7.38-7.34 (m, 2H), 7.34-7.28 (m, 4H), 7.28-7.24 (m, 3H), 5.42 (d, J=9.8 Hz, 1H), 5.20 (s, 2H), 5.13 (d, J=15.6 Hz, 1H), 4.58 (d, J=9.8 Hz, 1H), 4.40 (d, J=15.6 Hz, 1H), 4.26 (dd, J=7.3, 6.4 Hz, 1H), 3.91 (s, 3H), 3.69 (dt, J=10.3, 9.8 Hz, 1H), 3.62-3.56 (m, 1H), 3.53 (dd, J=15.4, 7.6 Hz, 1H), 2.98 (dd, J=15.6, 6.4 Hz, 1H), 0.98-0.94 (m, 2H), 0.04 (s, 9H). LC/MS: retention time 3.97 min. (ES$^+$) calc. for $C_{31}H_{37}N_2O_5Si$: [M+H]$^+$ 545. found 545.

2-Hydroxy-3-methoxy-13-(2-trimethylsilanyl-ethoxymethyl)-11,11a-dihydro-6H,13H-5a, 13-di-aza-benzo[4,5]cyclohepta[1,2-b]naphthalene-5,12-dione (3)

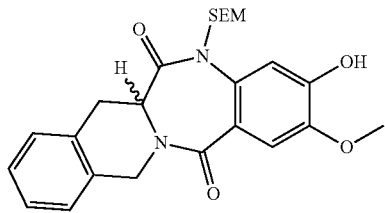

3

A solution of 2-benzyloxy-3-methoxy-13-(2-trimethylsilanyl-ethoxymethyl)-11,11a-dihydro-6H,13H-5a, 13-diaza-benzo[4,5]cyclohepta[1,2-b]naphthalene-5,12-dione (4) (1.99 g, 3.66 mmol) in EtOH (40 mL), was purged with Ar (3×), then Pd(OH)$_2$ (400 mg) was added. The mixture was purged with Ar (3×), then with H$_2$ (3×). The resulting mixture was stirred under H$_2$ (1 atm) at ambient temperature for 30 min, at which point the reaction was judged complete by TLC and LC/MS. After purging with Ar (3×), the reaction was filtered through celite, washed with MeOH, the filtrate was concentrated in vacuo, and the resulting residue was purified via column chromatography (0→75% EtOAc in Hex) to provide (6) as a yellow solid (1.63 g, 98% yield, 3.58 mmol). $^1$H NMR (500 MHz, CDCl$_3$): δ 7.33-7.28 (m, 3H), 7.28-7.24 (m, 3H), 5.93 (s, 1H), 5.44 (d, J=9.8 Hz, 1H), 5.15 (d, J=15.1 Hz, 1H), 4.69 (d, J=9.8 Hz, 1H), 4.40 (d, J=15.6 Hz, 1H), 4.28 (dd, J=7.6, 6.6 Hz, 1H), 3.93 (s, 3H), 3.74-3.68 (m, 1H), 3.66-3.60 (m, 1H), 3.56 (dd, J=15.4, 7.6 Hz, 1H), 2.99 (dd, J=15.4, 6.6 Hz, 1H), 0.99 (t, J=8.3 Hz, 2H), 0.02 (s, 9H). LC/MS: retention time 3.30 min. (ES$^+$) calc for $C_{24}H_{29}N_2O_5Si$: [M−H]$^-$ 453. found 453.

Bis SEM-CLT-D201 (2)

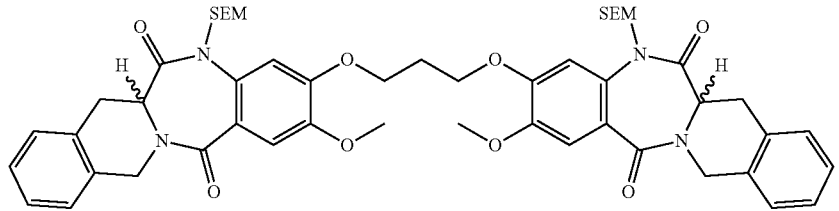

2

To an argon-purged solution of 2-hydroxy-3-methoxy-13-(2-trimethylsilanyl-ethoxymethyl)-11,11a-dihydro-6H,13H-5a, 13-diaza-benzo[4,5]cyclohepta[1,2-b]naphthalene-5,12-dione (3) (300 mg, 0.660 mmol) in THF (2.4 mL), was added triphenylphosphine (260 mg, 0.990 mmol). The mixture was then cooled to 0° C., and diethyl azodicarboxylate (114 µL, 0.726 mmol) was added dropwise. The resulting mixture was stirred at 0° C. for 45 min, then 1,3-propane diol (23 µL, 0.317 mmol) was added to the cold reaction and the mixture was allowed to slowly warm to ambient temperature overnight. The mixture was concentrated in vacuo, and the resulting residue was purified via column chromatography (0→75% EtOAc in Hex) to provide (2) as a yellow solid (103 mg, 34% yield, 0.109 mmol). $^1$H NMR (500 MHz, CDCl$_3$): δ 7.33-7.28 (m, 8H), 7.28-7.24 (m, 2H), 7.22 (s, 2H), 5.47 (d, J=9.8 Hz, 2H), 5.14 (d, J=15.1 Hz, 2H), 4.71 (dd, J=10.3, 1.0 Hz, 2H), 4.41 (d, J=15.6 Hz, 2H), 4.29-4.20 (m, 6H), 3.86 (s, 6H), 3.76 (dt, J=9.8, 6.8 Hz, 2H), 3.67 (dt, J=9.8, 7.1 Hz, 2H), 3.57 (dd, J=15.4, 7.6 Hz, 2H), 2.99 (ddd, J=15.6, 6.4, 4.4 Hz, 2H), 2.41 (p, J=5.9 Hz, 2H), 0.95 (ddd, J=9.8, 6.8, 2.9 Hz, 4H), 0.01 (s, 18H). LC/MS: retention time 4.39 min. (ES$^+$) calc. for C$_{51}$H$_{65}$N$_4$O$_{10}$Si$_2$: [M+H]$^+$ 949. found 949.

CLT-D201

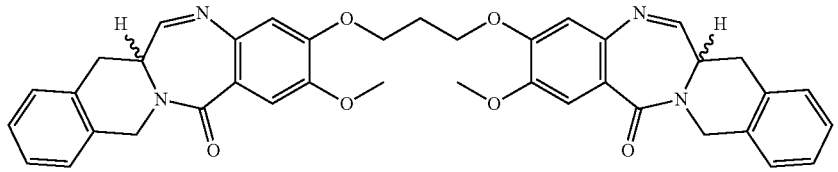

CLT-D201

To an oven-dried 4 mL vial containing a stir bar was added Bis SEM-CLT-D201 (2) (50.0 mg, 0.526 mmol). The solid was placed under argon, then dissolved in anhydrous THF (1.5 mL) and the resultant solution was cooled to −78° C. in a dry ice/acetone cooling bath. To the cooled solution, lithium triethylborohydride (110 µL, 0.111 mmol, 1.0 M solution in THF) was added drop-wise over five minutes. The reaction was allowed to stir at −78° C. for 90 minutes, at which point 1.0 mL H$_2$O was added via syringe and the solution was removed from the cooling bath and allowed to reach ambient temperature. The THF was removed under reduced pressure and to the resultant aqueous suspension was added 1.0 mL DMSO. This solution was loaded directed onto a pre-equilibrated 30 g RediSep® Rf reversed phase C18 column. The product was eluted using a gradient of 5-95% acetonitrile in H$_2$O (0.05% AcOH). The pure fractions were combined and lyophilized to give 8.7 mg (25% yield) of the desired product (1) as a fluffy white solid. $^1$H NMR (500 MHz, CDCl$_3$): δ 7.51 (d, J=5.5 Hz, 2H), 7.47 (d, J=5.5, 1H), 7.44 (d, J=5.5 Hz, 2H), 7.38-7.28 (m, 8H), 6.83 (d, J=11.5 Hz, 2H), 5.00 (d, J=15.5 Hz, 2H), 4.54 (dd, J=13.5, 3.0 Hz, 2H), 4.33-4.20 (m, 4H), 3.93 (s, 3H), 3.92 (s, 3H), 3.94-3.88 (m, 1H), 3.30-3.21 (m, 2H), 3.18-3.11 (m, 2H), 2.41 (sextet, J=5.5 Hz, 2H). LC/MS: retention time 2.77 min. (ES$^+$) calc. for C$_{39}$H$_{37}$N$_4$O$_6$: [M+H]$^+$ 657. found 657.

CLT-D201 Cytotoxicity

The cytotoxicity of the compounds was evaluated using the CellTiter-Glo Luminescent Cell Viability Assay (Promega Cat#G7573) as described in the manufacturer's instructions (Arduengo, M., Cell Notes, 2003, 5:15-17). This assay contains a reagent that lyses cells and generates a "glow-type" luminescent signal proportional to the amount of adenosine triphosphate (ATP) present, which is a measure of cell growth.

Cells were seeded at 1000 cells per well in 50 µL of culture media into tissue culture 96-well flat-bottom plates. The perimeter wells of the plate were not used and 200 µL of media was added to the perimeter wells to prevent evaporation during incubation. 50 µL of the compound tested at twice the final concentration were then added to the wells in triplicate. Plates were incubated at 37° C., 5% CO$_2$ for 72 hours before adding 100 µL CellTiter-Glo reagent to each well (excluding perimeter wells). Plates were then incubated at room temperature on a shaker for 10 minutes. After incubation, 100 µL of the supernatants were transferred to a solid white 96-well plate and luminescence was measured with a spectrophotometer. Percent viability was calculated based on untreated control: % viability=(treated/untreated)*100.

GI$_{50}$: Concentration of compound required for 50% cell growth inhibition.

Example 2

Synthesis of CLT-D501

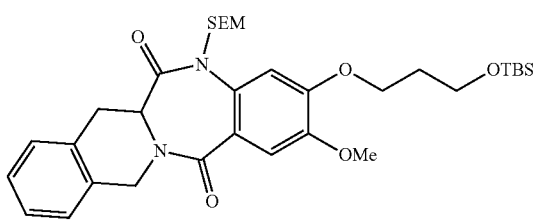

2-[3-(t-Butyl-dimethyl-silanyloxy)-propoxy]-3-methoxy-13-(2-trimethylsilanyl-ethoxymethyl)-11, 11a-dihydro-6H, 13H-5a, 13-diaza-benzo[4,5]cyclohepta[1,2-b]naphthalene-5,12-dione (5)

Referring to FIG. 4, to an Ar purged solution of 2-hydroxy-3-methoxy-13-(2-trimethylsilanyl-ethoxymethyl)-11, 11a-dihydro-6H,13H-5a, 13-diaza-benzo[4,5]cyclohepta[1, 2-b]naphthalene-5,12-dione (6) (400 mg, 0.880 mmol) in THF (8.8 mL) at 22° C., added triphenylphosphine (462 mg, 1.76 mmol) and di-t-butyl azadicarboxylate (405 mg, 1.76 mmol). The mixture was stirred for 1 h, then 3-(t-butyl-dimethyl-silanyloxy)-propan-1-ol (282 μL, 1.32 mmol) was added to the reaction mixture. The reaction was stirred at 22° C. overnight, under Ar. The mixture was then concentrated in vacuo and purified via column chromatography (0→50% EtOAc in Hexanes to provide (5) as an off-white foam in >95% yield. $^1$H NMR (500 MHz, CDCl3): δ 7.33-7.28 (m, 3H), 7.28-7.24 (m, 3H), 5.49 (d, J=9.8 Hz, 1H), 5.15 (d, J=15.1 Hz, 1H), 4.65 (d, J=9.8 Hz, 1H), 4.41 (d, J=15.1 Hz, 1H), 4.28 (dd, J=7.3, 6.4 Hz, 1H), 4.18-3.99 (m, 2H), 3.88 (s, 3H), 3.82 (t, J=5.9 Hz, 2H), 3.77 (td, J=9.8, 6.8 Hz, 1H), 3.66 (td, J=9.8, 6.8 Hz, 1H), 3.56 (dd, J=15.1, 7.3 Hz, 1H), 3.00 (dd, J=15.6, 6.4 Hz, 1H), 2.06 (p, J=6.4 Hz, 2H), 1.54 (s, 6H), 0.98 (sep, J=3.4 Hz, 2H), 0.87 (s, 9H), 0.03 (s, 9H). LC/MS: retention time 4.71 min. (ES+) calc for C33H51N2O6Si2: [M+H]+ 627. found 627.

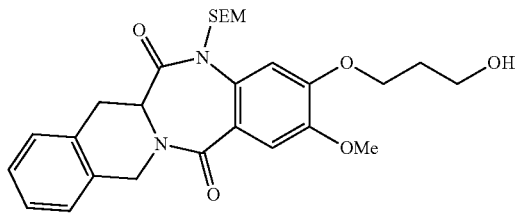

2-(3-Hydroxy-propoxy)-3-methoxy-13-(2-trimethyl-silanyl-ethoxymethyl)-11,11a-dihydro-6H,13H-5a, 13-diaza-benzo[4,5]cyclohepta[1,2-b]naphthalenene-5,12-dione (4)

To a solution of 2-[3-(t-butyl-dimethyl-silanyloxy)-propoxy]-3-methoxy-13-(2-trimethylsilanyl-ethoxymethyl)-11,11a-dihydro-6H,13H-5a, 13-diaza-benzo[4,5]cyclohepta [1,2-b]naphthalene-5,12-dione (5) (615 mg, 0.98 mmol) in THF (9.8 mL), tetrabutylammonium fluoride (1.23 mL of a 1.0M solution in THF, 1.23 mmol) was added under Ar. The mixture was allowed to stir at 22° C. for 2 h, at which time the reaction was judged complete by TLC and LC/MS. The mixture was quenched by pouring onto sat. NH4Cl (aq) (20 mL) and extracting with EtOAc (3×20 mL). The combined organics were washed with brine (50 mL), dried over MgSO4, filtered, concentrated and purified by column chromatography in 0-100% EtOAc in Hexanes to afford (4) as a white crystalline solid (411 mg, 82% yield, 0.802 mmol). $^1$H NMR (500 MHz, CDCl3): δ 7.33-7.29 (m, 3H), 7.29-7.24 (m, 3H), 5.50 (d, J=10.3 Hz, 1H), 5.15 (d, J=15.6 Hz, 1H), 4.67 (d, J=9.8 Hz, 1H), 4.42 (d, J=15.6 Hz, 1H), 4.30-4.18 (m, 3H), 3.90-3.86 (m, 2H), 3.88 (s, 3H), 3.79 (td, J=9.8, 6.4 Hz, 1H), 3.66 (td, J=9.3, 6.8 Hz, 1H), 3.57 (dd, J=15.1, 6.8 Hz, 1H), 3.00 (dd, J=9.3, 6.4 Hz, 1H), 2.22 (t, J=5.9 Hz, 1H), 2.10 (p, J=5.9 Hz, 1H), 1.02-0.92 (m, 2H), 0.03 (s, 9H). LC/MS: retention time 3.26 min. (ES+) calc for C27H37N2O6Si: [M+H]+ 513. found 513.

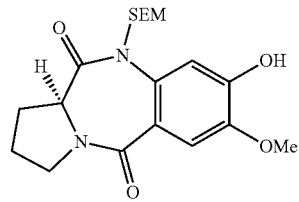

8-Hydroxy-7-methoxy-10-(2-trimethylsilanyl-ethoxymethyl)-1,2,3,11a-tetrahydro-10H-benzo[e]pyrrolo[1,2-a][1,4]diazepine-5,11-dione (3)

Figure 6:
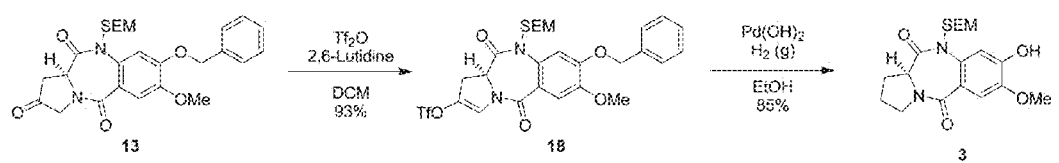
FIG. 6 shows an experimental scheme for the chemical synthesis of an intermediate in the synthesis of CLT-D501.

To a solution of trifluoro-methanesulfonic acid 8-benzyloxy-7-methoxy-5,11-dioxo-10-(2-trimethylsilanyl-ethoxymethyl)-5,10,11,11a-tetrahydro-1H-benzo[e]pyrrolo [1,2-a][1,4]diazepin-2-yl ester (18, from FIG. 6) (650 mg, 1.03 mmol) in EtOH (20 mL), purged with Ar (3×), added Pd(OH)2/C (300 mg). The reaction mixture was then purged with Ar (3×) then with H2 (3×) and allowed to stir at 22° C., under H2 (1 atm) for 3 h, at which point the reaction was judged complete by TLC and LC/MS. The mixture was filtered through celite, which was washed with MeOH. The combined organics were concentrated and the resulting residue was purified by column chromatography in 0-100% EtOAc in Hexanes to afford (3) as a white solid (345 mg, 85% yield). $^1$H NMR (500 MHz, CDCl3): δ 7.37 (s, 1H), 7.26 (s, 1H), 5.45 (d, J=9.8 Hz, 1H), 4.69 (d, J=10.3 Hz, 1H), 4.19 (d, J=6.8 Hz, 1H), 3.96 (s, 3H), 3.79-3.69 (m, 2H), 3.67-3.60 (m, 1H), 3.59-3.52 (m, 1H), 2.76-2.69 (m, 1H), 2.14-2.05 (m, 1H), 2.05-1.94 (m, 2H), 1.71 (bs, 1H), 0.99 (t, J=8.3 Hz, 2H), 0.03 (s, 9H). LC/MS: retention time 2.85 min. (ES+) calc for C19H29N2O5Si: [M+H]+ 393. found 393.

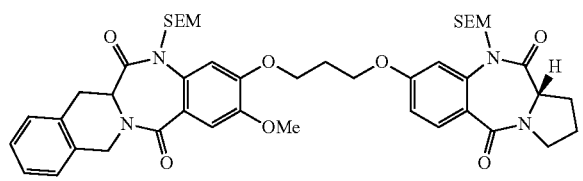

Bis-SEM-CLT-D501

To an Ar purged solution of triphenylphosphine (171 mg, 0.650 mmol) in THF (2 mL) at 22° C., added and di-t-butyl azadicarboxylate (150 mg, 0.650 mmol). The mixture was allowed to stir for 30 min, then 8-hydroxy-7-methoxy-10-(2-trimethylsilanyl-ethoxymethyl)-1,2,3,11a-tetrahydro-10H-benzo[e]pyrrolo[1,2-a][1,4]diazepine-5,11-dione (3) (107 mg, 0.325 mmol) in THF (2 mL) was added to the formed slurry. The resulting mixture was stirred for an additional 30 min before 2-(3-hydroxy-propoxy)-3-methoxy-13-(2-trimethylsilanyl-ethoxymethyl)-11,11a-dihydro-6H,13H-5a, 13-diaza-benzo[4,5]cyclohepta[1,2-b] naphthalenene-5,12-dione (4) (200 mg, 0.390 mmol) in THF (3 mL) was introduced to the mixture. The reaction was stirred at 22° C. overnight, under Ar. The mixture was then concentrated in vacuo and purified via column chromatography (0→100% EtOAc in Hex) to provide impure (2). The impure material was then purified by reverse phase C18 to afford (2) as a white fluffy powder (58 mg, 20%, 0.0652 mmol). $^1$H NMR (500 MHz, CDCl3): δ 7.35 (d, J=2.4 Hz, 1H), 7.33-7.28 (m, 3H), 7.28-7.24 (m, 2H), 7.24-7.21 (m, 2H), 5.48 (dd, J=10.3, 3.9 Hz, 2H), 5.15 (dd, J=15.1, 3.4 Hz, 1H), 4.71 (td, J=10.3, 2.9 Hz, 2H), 4.39 (dd, J=15.1, 2.0 Hz, 1H), 4.30-4.18 (m, 5H), 4.10 (td, J=7.8, 2.0 Hz, 1H), 3.89 (d, J=1.5 Hz, 3H), 3.86 (d, J=1.0 Hz, 3H), 3.79-3.72 (m, 3H), 3.69 (q, J=7.8 Hz, 2H), 2.99 (dq, J=15.1, 2.9 Hz, 1H), 2.72-2.70 (m, 1H), 2.41 (q, J=5.9 Hz, 2H), 2.16-2.04 (m, 1H), 2.04-1.95 (m, 2H), 1.02-0.92 (m, 4H), 0.00 (s, 18H). LC/MS: retention time 4.16 min. (ES+) calc for C46H63N4O10Si2: [M+H]+ 888. found 888.

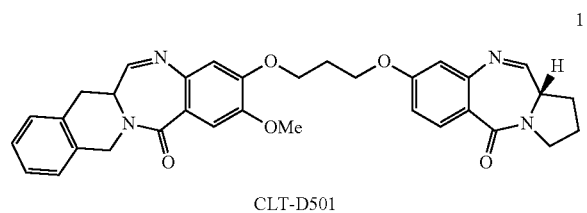 [SMILES: COc1cc2c(cc1OCCCOc1ccc3c(c1)N=C[C@@H]1CCCN1C3=O)N=CC1Cc3ccccc3CN1C2=O]

CLT-D501

To an oven-dried 4 mL vial containing a stirbar was added Bis SEM-CLT-D501 (2) (47.0 mg, 0.529 mmol). The solid was placed under argon, then dissolved in anhydrous THF (1.5 mL) and the resultant solution was cooled to −78° C. in a dry ice/acetone cooling bath. To the cooled solution, super hydride (110 μL, 0.110 mmol, 1.0 M solution in THF) was added drop-wise over five minutes. The reaction was allowed to stir at −78° C. for 75 minutes, at which point 1.0 mL H$_2$O was added via syringe and the solution was removed from the cooling bath and allowed to reach ambient temperature. The THF was removed under reduced pressure and to the resultant aqueous suspension was added 1.0 mL DMSO. This solution was loaded directed onto a pre-equilibrated 30 g RediSep® Rf reversed phase C18 column. The product was eluted using a gradient of 5-95% Acetonitrile in H$_2$O (0.05% AcOH). The pure fractions were combined and lyophilized to give 17.7 mg (57% yield) of the desired product (1) as a fluffy white solid. $^1$H NMR (500 MHz, CDCl3): δ 7.64 (dd, J=11.0, 4.5 Hz, 1H), 7.52 (d, J=5.0 Hz, 1H), 7.50 (d, J=10.0 Hz, 1H), 7.46 (dd, J=12.5, 4.5 Hz, 1H), 7.38-7.29 (m, 4H), 6.84 (d, J=10.5 Hz, 2H), 5.00 (d, J=15 Hz, 1H), 4.55 (dd, J=16.0, 8.0 Hz, 1H), 4.34-4.22 (m, 4H), 3.94-3.92 (m, 6H), 3.86-3.78 (m, 2H), 3.71-3.66 (m, 1H), 3.60-3.54 (m, 1H), 3.26 (dt, J=15.5, 6.0 Hz, 1H), 3.15 (dq, J=16.0, 4.5 Hz, 1H), 2.41 (sextet, J=6.0 Hz, 2H), 2.34-2.27 (m, 2H), 2.09-2.00 (m, 2H). LC/MS: retention time 2.43 min. (ES+) calc for C35H34N4O6: [M+H]+ 595. found 595.

Example 3

Synthesis of CLT-D601

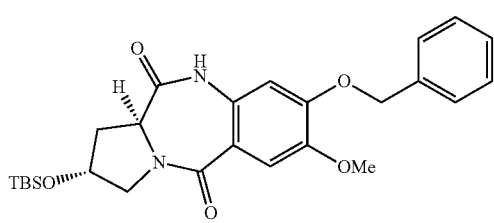

8-Benzyloxy-2-(tert-butyl-dimethyl-silanyloxy)-7-methoxy-1,2,3,11a-tetrahydro-10H-benzo[e]pyrrolo [1,2-a][1,4]diazepine-5,11-dione (16)

Referring to FIG. 5, to 8-benzyloxy-2-hydroxy-7-methoxy-1,2,3,11a-tetrahydro-10OH-benzo[e]pyrrolo[1,2-a][1,4]diazepine-5,11-dione (17 from FIG. 5) (4.00 g, 10.86 mmol), under Ar, added DMF (100 mL) followed by imidazole (8.87 g, 130 mmol). The mixture was stirred at 22° C. for 1 h, then TBSCl (8.18 g, 54.3 mol) was added and the resulting mixture was stirred at 22° C. for 18 h. The reaction mixture was then poured onto H$_2$O and extracted with EtOAc (3×100 mL). The combined organics were washed with H$_2$O (100 mL), then brine (100 mL), dried over MgSO$_4$, filtered and concentrated. The resulting residue was purified via column chromatography in 0-75% EtOAc in Hexane to afford (16) as a white solid (630 mg, 12%, 1.30 mmol). $^1$H NMR (500 MHz, CDCl3): δ 7.46 (s, 1H), 7.43-7.38 (m, 4H), 7.36-7.31 (m, 2H), 6.38 (s, 1H), 5.19 (s, 2H), 4.52 (p, J=5.4 Hz, 1H), 4.18 (dd, J=4.4, 3.9 Hz, 1H), 3.95 (s, 3H), 3.69 (qd, J=11.7, 5.9 Hz, 2H), 2.82 (td, J=12.7, 5.4 Hz, 1H), 2.05 (m, 1H), 0.88 (s, 9H), 0.10 (s, 6H). LC/MS: retention time 3.65 min. (ES+) calc for C26H35N2O5Si: [M+H]+ 483. found 483.

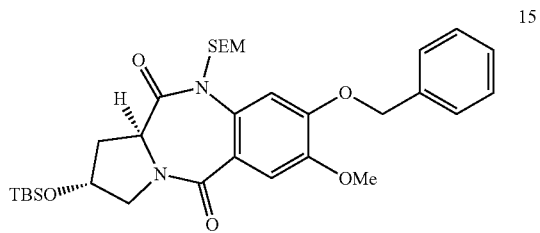 [SMILES: COc1cc2c(cc1OCc1ccccc1)N(COCC[Si](C)(C)C)C(=O)[C@@H]1C[C@@H](O[Si](C)(C)C(C)(C)C)CN1C2=O]

8-Benzyloxy-2-(tert-butyl-dimethyl-silanyloxy)-7-methoxy-10-(2-trimethylsilanyl-ethoxymethyl)-1,2, 3,11a-tetrahydro-10 OH-benzo[e]pyrrolo[1,2-a][1,4] diazepine-5,11-dione (15)

A purged solution of 8-benzyloxy-2-(tert-butyl-dimethyl-silanyloxy)-7-methoxy-1,2,3,11a-tetrahydro-10H-benzo[e] pyrrolo[1,2-a][1,4]diazepine-5,11-dione (16) in THF (15 mL) was cooled to −40° C. in a dry ice/acetonitrile bath. n-BuLi (1.02 mL of a 1.6M solution in Hexanes, 1.63 mmol) was then added drop wise and the resulting mixture was stirred for 1 h, at which time SEMCl (288 L, 1.63 mmol) in THF (5 mL) was added drop wise. The resulting reaction mixture was allowed to stir while slowly warming up to 22° C. over 18 h. The mixture was then partitioned between EtOAc and H$_2$O. The mixture was extracted with EtOAc (3×20 mL). The combined organics were washed with brine (20 mL), dried over MgSO4, filtered and concentrated. The isolated residue was purified via column chromatography in 0-50% EtOAc in Hexanes to afford (15) as a pale yellow foam (774 mg, 97%, 1.26 mmol). $^1$H NMR (500 MHz, CDCl3): δ 7.45-7.41 (m, 2H), 7.38-7.34 (m, 3H), 7.34-7.29 (m, 1H), 7.24 (s, 1H), 5.42 (d, J=9.8 Hz, 1H), 5.20 (s, 2H), 4.56 (p, J=5.9 Hz, 1H), 4.48 (d, J=9.8 Hz, 1H), 4.20 (q, J=3.9 Hz, 1H), 3.95 (s, 3H), 3.73 (dd, J=12.2, 5.9 Hz, 2H), 3.69 (td, J=9.3, 7.3 Hz, 1H), 3.59 (td, J=9.3, 7.3 Hz, 1H), 3.54 (dd, J=5.4 Hz, 1H), 2.83 (qd, J=12.7, 3.9 Hz, 1H), 2.01 (ddd, J=14.7, 12.7, 7.8 Hz, 1H), 0.96 (ddd, J=9.8, 6.8, 2.4 Hz, 2H), 0.87 (s, 9H), 0.09 (s, 6H), 0.04 (s, 9H). LC/MS: retention time 4.63 min. (ES+) calc for C32H49N2O6Si2: [M+H]+ 613. found 613.

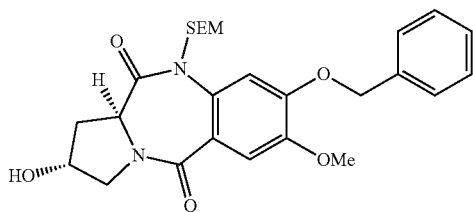

8-Benzyloxy-2-hydroxy-7-methoxy-10-(2-trimethyl-silanyl-ethoxymethyl)-1,2,3,11a-tetrahydro-10OH-benzo[e]pyrrolo[1,2-a][1,4]diazepine-5,11-dione (14)

To a solution of 8-benzyloxy-2-(t-butyl-dimethyl-silanyloxy)-7-methoxy-10-(2-trimethylsilanyl-ethoxymethyl)-1,2,3,11a-tetrahydro-10 OH-benzo[e]pyrrolo[1,2-a][1,4]diazepine-5,11-dione (15) (1.61 g, 2.37 mmol) in THF (40 mL), tetrabutylamonium fluoride (3.28 mL of a 1.0M solution in THF, 3.28 mmol) was added under Ar. The mixture was allowed to stir at ambient temperature for 18 h, at which time the reaction was judged complete by TLC and LC/MS. The mixture was quenched by pouring onto sat. NH4Cl (aq) (50 mL) and extracting with EtOAc (3×50 mL). The combined organics were washed with brine (100 mL), dried over MgSO4, filtered, concentrated and purified by column chromatography in 0-100% EtOAc in Hexanes to afford (14) as a white crystalline solid (1.18 g, 91% yield, 2.37 mmol). ¹H NMR (500 MHz, CDCl3): δ 7.45-7.42 (m, 2H), 7.39-7.35 (m, 3H), 7.34-7.30 (m, 1H), 7.25 (s, 1H), 5.43 (d, J=9.8 Hz, 1H), 5.21 (s, 2H), 4.65 (q, J=4.4 Hz, 1H), 4.50 (d, J=9.8 Hz, 1H), 4.28 (dd, J=7.8, 5.4 Hz, 1H), 3.95 (s, 3H), 3.84 (ddd, J=12.7, 3.9, 1.5 Hz, 1H), 3.72-3.63 (m, 2H), 3.60 (td, J=9.8, 6.4 Hz, 1H), 2.96 (dt, J=13.7, 5.4 Hz, 1H), 2.10 (dddd, J=13.7, 7.8, 4.4, 1.5 Hz, 1H), 1.71 (d, J=3.4 Hz, 1H), 0.96 (ddd, J=9.8, 6.8, 2.9 Hz, 2H), 0.04 (s, 9H). LC/MS: retention time 3.32 min. (ES+) calc for C26H35N2O6Si: [M+H]+ 499. found 499.

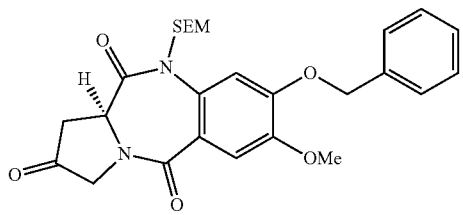

8-Benzyloxy-7-methoxy-10-(2-trimethylsilanyl-ethoxymethyl)-1,11a-dihydro-1 OH-benzo[e]pyrrolo[1,2-a][1,4]diazepine-2,5,11-trione (13)

To an Ar purged solution of oxalyl chloride (301 ⁻l, 3.56 mmol) in DCM (1.8 mL), cooled to −78° C., added dry DMSO (505 µL, 7.11 mmol) in DCM (20 mL), drop wise. Allowed the mixture to stir at −78° C. for 2 h, then added 8-benzyloxy-2-hydroxy-7-methoxy-10-(2-trimethylsilanyl-ethoxymethyl)-1,2,3,11a-tetrahydro-1 OH-benzo[e]pyrrolo[1,2-a][1,4]diazepine-5,11-dione (14) (1.18 g, 2.37 mmol) in DCM (50 mL) drop wise over 45 min. The resulting mixture was stirred for 45 min, then Et3N (2.31 mL, 16.59 mmol) was added drop wise to the reaction mixture. After an additional 30 min of stirring, the cold bath was removed and the reaction was allowed to slowly rise to 22° C. over ~1.5 h, at which time the reaction was judged complete by TLC and LC/MS. Diluted with DCM (50 mL), and washed organics with 1 N HCl (75 mL), sat. NaHCO3 (aq) (75 mL), H2O (75 mL), and brine (75 mL). The organics were then dried over MgSO4, filtered, concentrated and the resulting residue was purified by column chromatography in 0-100% EtOAc in Hexanes to afford (13) as an off-white foam (873 mg, 74% yield, 1.76 mmol). ¹H NMR (500 MHz, CDCl3): δ 7.46-7.42 (m, 2H), 7.40-7.36 (m, 2H), 7.34 (s, 1H), 7.34-7.29 (m, 1H), 7.28 (s, 1H), 5.46 (d, J=9.8 Hz, 1H), 5.22 (d, J=2.5 Hz, 2H), 4.62 (dd, J=9.8, 2.9 Hz, 1H), 4.55 (d, J=9.8 Hz, 1H), 4.23 (d, J=20.0 Hz, 1H), 3.96 (s, 3H), 3.89 (d, J=20.0 Hz, 1H), 3.70 (dt, J=10.3, 6.4 Hz, 1H), 3.60 (dt, J=16.6, 6.4 Hz, 1H), 3.58-3.52 (m, 1H), 2.77 (qd, J=19.1, 1.0 Hz, 1H), 1.02-0.92 (m, 2H), 0.04 (s, 9H). LC/MS: retention time 3.57 min. (ES+) calc for C26H32N2NaO6Si: [M+Na]+ 519. found 519.

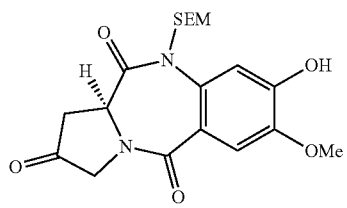

8-Hydroxy-7-methoxy-10-(2-trimethylsilanyl-ethoxymethyl)-1,11a-dihydro-10H-benzo[e]pyrrolo[1,2-a][1,4]diazepine-2,5,11-trione (12)

To a solution of 8-benzyloxy-7-methoxy-10-(2-trimethylsilanyl-ethoxymethyl)-1,11a-dihydro-10H-benzo[e]pyrrolo[1,2-a][1,4]diazepine-2,5,11-trione (13) (866 mg, 1.75 mmol) in EtOH (20 mL), purged with Ar (3×), added Pd(OH)2/C (180 mg, 0.2% w/w). The reaction mixture was then purged with Ar (3×) then with H2 (3×) and allowed to stir at 22° C., under H2 (1 atm) for 30 min, at which point the reaction was judged complete by TLC and LC/MS. The mixture was filtered through celite, which was washed with MeOH. The combined organics were concentrated and the resulting residue was purified by column chromatography in 0-100% EtOAc in Hexanes to afford (12) as a white solid (642 mg, 90% yield, 1.58 mmol). ¹H NMR (500 MHz, CDCl3): δ 7.35 (s, 1H), 7.30 (s, 1H), 6.00 (s, 1H), 5.48 (d, J=9.8 Hz, 1H), 4.75 (d, J=9.8 Hz, 1H), 4.63 (dd, J=9.8, 2.9 Hz, 1H), 4.23 (d, J=20.0 Hz, 1H), 3.98 (s, 3H), 3.90 (d, J=20.0 Hz, 1H), 3.72 (td, J=16.6, 7.3 Hz, 1H), 3.64 (td, J=16.6, 7.8 Hz, 1H), 3.62-3.55 (m, 1H), 2.78 (qd, J=9.3, 1.0 Hz, 1H), 0.99 (ddd, J=8.3, 6.8, 6.8 Hz, 2H), 0.02 (s, 9H). LC/MS: retention time 2.80 min. (ES+) calc for C19H25N2O6SiN: [M−H]− 405. found 405.

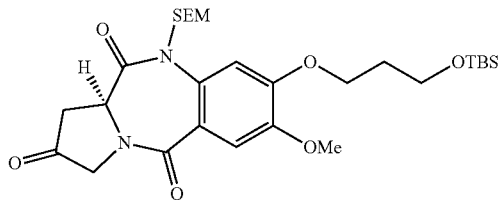

8-[3-(tert-Butyl-dimethyl-silanyloxy)-propoxy]-7-methoxy-10-(2-trimethylsilanyl-ethoxymethyl)-1,11a-dihydro-1 OH-benzo[e]pyrrolo[1,2-a][1,4]diazepine-2,5,11-trione (11)

To an Ar purged solution of 8-hydroxy-7-methoxy-10-(2-trimethylsilanyl-ethoxymethyl)-1,11a-dihydro-10H-benzo[e]pyrrolo[1,2-a][1,4]diazepine-2,5,11-trione (12) (642 mg, 1.58 mmol) in THF (16 mL) cooled to 0° C., added triphenylphosphine (621 mg, 2.37 mmol) and diethyl azadicarboxylate (298 µL, 1.89 mmol), drop wise. The mixture was stirred for 1 h, then 3-(t-butyl-dimethyl-silanyloxy)-propan-1-ol (370 µL, 1.73 mmol) was added to the reaction mixture. The reaction was stirred and allowed to warm up to 22° C. overnight, under Ar. The mixture was then concentrated in vacuo and purified via column chromatography (0-100% EtOAc in Hex) to afford (11) as a white foam (127 mg, 14%, 0.221 mmol). $^1$H NMR (500 MHz, CDCl3): δ 7.33 (s, 1H), 7.26 (s, 1H), 5.53 (d, J=9.8 Hz, 1H), 4.71 (d, J=10.3 Hz, 1H), 4.64 (dd, J=9.8, 2.9 Hz, 1H), 4.24 (d, J=20.0 Hz, 1H), 4.19-4.11 (m, 2H), 3.92 (s, 3H), 3.90 (d, J=21.5 Hz, 1H), 3.83 (t, J=5.9 Hz, 2H), 3.77 (td, J=9.8, 6.4 Hz, 1H), 3.67 (td, J=9.8, 6.8 Hz, 1H), 3.61-3.55 (m, 1H), 2.79 (qd, J=9.8, 1.0 Hz, 1H), 2.11-2.04 (m, 2H), 0.94 (m, 2H), 0.88 (s, 9H), 0.04 (d, J=2.0 Hz, 6H), 0.03 (s, 9H). LC/MS: retention time 4.33 min. (ES+) calc for C28H46N2NaO7Si2: [M+Na]+601. found 601.

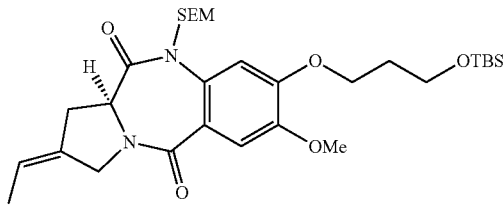

8-[3-(tert-Butyl-dimethyl-silanyloxy)-propoxy]-2-ethylidene-7-methoxy-10-(2-trimethylsilanyl-ethoxymethyl)-1,2,3,11a-tetrahydro-10 OH-benzo[e]pyrrolo[1,2-a][1,4]diazepine-5,11-dione (10)

To a solution of (ethyl)-triphenylphosphonium bromide (237 mg, 0.639 mmol) in THF (1 mL), under Ar, added potassium t-butoxide (0.64 mL of a 1.0 M solution in THF, 0.64 mmol). The mixture was allowed to stir for 1 h, then 8-[3-(t-butyl-dimethyl-silanyloxy)-propoxy]-7-methoxy-10-(2-trimethylsilanyl-ethoxymethyl)-1,11a-dihydro-1 OH-benzo[e]pyrrolo[1,2-a][1,4]diazepine-2,5,11-trione (11) (185 mg, 0.320 mmol) in THF (2 mL) was added to the reaction mixture and the mixture was allowed to stir at 22° C. for 1 h, at which time the reaction was judged complete by TLC and LC/MS. The reaction was quenched with H2O (2 mL), and extracted with EtOAc (3×5 mL). The combined organics were washed with H2O (5 mL), dried over MgSO4, filtered and concentrated. The isolated residue was purified by column chromatography in 0-50% EtOAc in Hexanes to afford (10) as an off-white foam (146 mg, 89% yield, 0.285 mmol) in ~10:1 Z/E regioselectivity. $^1$H NMR (500 MHz, CDCl3) (Z isomer): δ 7.34 (s, 1H), 7.24 (s, 1H), 5.59-5.53 (m, 1H), 5.50 (d, J=10.3 Hz, 1H), 4.63 (d, J=9.8 Hz, 1H), 4.24 (dd, J=8.8, 2.0 Hz, 3H), 4.18-4.09 (m, 3H), 3.92 (s, 3H), 3.91 (d, J=3.9 Hz, 1H), 3.82 (t, J=5.9 Hz, 2H), 3.78 (td, J=9.8, 6.4 Hz, 1H), 3.67 (td, J=9.8, 7.3 Hz, 1H), 3.36 (bd, J=15.6 Hz, 1H), 2.80-2.72 (m, 1H), 2.10-2.03 (m, 3H), 1.68-1.63 (m, 3H), 0.98 (ddd, J=9.8, 6.8, 3.4 Hz, 2H), 0.87 (s, 9H), 0.03 (d, J=2.0 Hz, 6H), 0.02 (s, 6H). LC/MS: retention time 4.64 min. (ES+) calc for C30H51N2O6Si2: [M+H]+ 591. found 591.

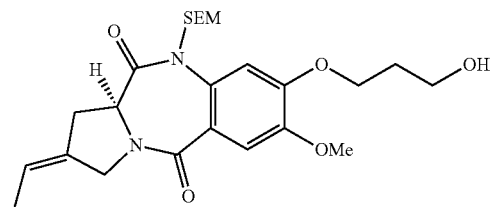

2-Ethyl idene-8-(3-hydroxy-propoxy)-7-methoxy-10-(2-trimethylsilanyl-ethoxymethyl)-1,2,3,11a-tetrahydro-10H-benzo[e]pyrrolo[1,2-a][1,4]diazepine-5,11-dione (9)

To a solution of 8-[3-(t-butyl-dimethyl-silanyloxy)-propoxy]-2-ethylidene-7-methoxy-10-(2-trimethylsilanyl-ethoxymethyl)-1,2,3,11a-tetrahydro-10H-benzo[e]pyrrolo[1,2-a][1,4]diazepine-5,11-dione (10) (220 mg, 0.372 mmol) in THF (3.7 mL), tetrabutylammonium fluoride (0.47 mL of a 1.0M solution in THF, 0.47 mmol) was added under Ar. The mixture was allowed to stir at 22° C. for 75 min, at which time the reaction was judged complete by TLC and LC/MS. The mixture was quenched by pouring onto sat. NH4Cl (aq) (5 mL) and extracting with EtOAc (3×5 mL). The combined organics were washed with brine (10 mL), dried over MgSO4, filtered, concentrated and the resulting residue was purified by column chromatography in 0-100% EtOAc in Hexanes to afford (9) as a white crystalline solid (115 mg, 65% yield, 0.240 mmol). $^1$H NMR (500 MHz, CDCl3): δ 7.35 (s, 1H), 7.25 (s, 1H), 5.60-5.53 (m, 1H), 5.51 (d, J=10.3 Hz, 1H), 4.65 (d, J=10.3 Hz, 1H), 4.30-4.18 (m, 5H), 3.93-3.86 (m, 5H), 3.79 (td, J=10.3, 6.8 Hz, 1H), 3.68 (td, J=9.8, 7.3 Hz, 1H), 3.37 (bd, J=16.1 Hz, 1H), 2.81-2.73 (m, 1H), 2.24 (t, J=5.9 Hz, 1H), 2.11 (p, J=5.9 Hz, 2H), 1.67-1.63 (m, 2H), 0.98 (ddd, J=9.8, 6.4, 4.4 Hz, 2H), 0.03 (s, 9H). LC/MS: retention time 3.09 min. (ES+) calc for C24H37N2O6Si: [M+H]+ 477. found 477.

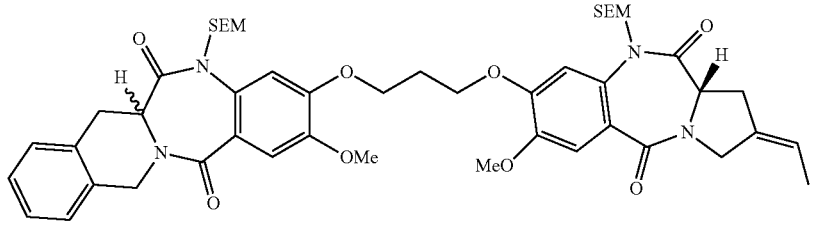

Bis-SEM CLT-D601

To an Ar purged solution of triphenylphosphine (105 mg, 0.400 mmol) in THF (1 mL) at 22° C., added and di-t-butyl azadicarboxylate (92 mg, 0.400 mmol). The mixture was allowed to stir for 30 min, then 2-hydroxy-3-methoxy-13-(2-trimethylsilanyl-ethoxymethyl)-11,11a-dihydro-6H, 13H-5a, 13-diaza-benzo[4,5]cyclohepta[1,2-b]naphthalene-5,12-dione (6) (65 mg, 0.200 mmol) in THF (1.5 mL) was added to the formed slurry. The resulting mixture was stirred for an additional 30 min before 2-ethylidene-8-(3-hydroxy-propoxy)-7-methoxy-10-(2-trimethylsilanyl-ethoxymethyl)-1,2,3,11a-tetrahydro-10 OH-benzo[e]pyrrolo[1,2-a][1,4]diazepine-5,11-dione (9) (115 mg, 0.240 mmol) in THF (2 mL) was introduced to the mixture. The reaction was stirred at 22° C. overnight, under Ar. The mixture was then concentrated in vacuo and purified via column chromatography (0→75% EtOAc in Hex) to afford (8) as a white crystalline solid (111 mg, 61% yield, 0.122 mmol). $^1$H NMR (500 MHz, CDCl3): δ 7.34 (d, J=2.5 Hz, 1H), 7.32-7.28 (m, 3H), 7.28-7.24 (m, 2H), 7.24-7.22 (m, 2H), 5.59-5.52 (m, 1H), 5.48 (dd, J=10.3, 2.9 Hz, 2H), 5.15 (dd, J=15.1, 2.9 Hz, 1H), 4.73-4.67 (m, 2H), 4.41 (dd, J=16.6, 1.5 Hz, 1H), 4.30-4.18 (m, 8H), 3.89 (d, J=2.4 Hz, 3H), 3.86 (d, J=1.0 Hz, 3H), 3.76 (td, J=9.8, 6.4 Hz, 2H), 3.69-3.62 (m, 2H), 3.55 (dd, J=15.6, 7.8 Hz, 1H), 3.36 (dd, J=15.6, 1.5 Hz, 1H), 2.99 (qd, J=15.6, 2.9 Hz, 1H), 2.80-2.71 (m, 1H), 2.41 (p, J=5.9 Hz, 2H), 1.65 (dd, J=6.8, 1.0 Hz, 3H), 0.96 (ddd, J=9.3, 5.9, 2.9 Hz, 4H), 0.01 (s, 9H), 0.00 (s, 9H). LC/MS: retention time 4.35 min. (ES+) calc for C48H64N4O10Si2: [M+H]+ 913. found 913.

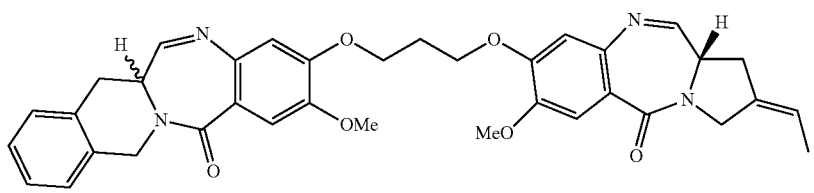

CLT-D601

To an oven-dried 4 mL vial containing a stirbar was added Bis SEM-CLT-D601 (8) (65.0 mg, 0.711 mmol). The solid was placed under argon, then dissolved in anhydrous THF (1.5 mL) and the resultant solution was cooled to −78° C. in a dry ice/acetone cooling bath. To the cooled solution, super hydride (146 µL, 0.146 mmol, 1.0 M solution in THF) was added drop-wise over five minutes. The reaction was allowed to stir at −78° C. for 75 minutes, at which point 1.0 mL H2O was added via syringe and the solution was removed from the cooling bath and allowed to reach ambient temperature. The THF was removed under reduced pressure and to the resultant aqueous suspension was added 1.0 mL DMSO. This solution was loaded directed onto a pre-equilibrated 30 g RediSep® Rf reversed phase C18 column. The product was eluted using a gradient of 5-95% Acetonitrile in H2O (0.05% AcOH). The pure fractions were combined and lyophilized to give 10.2 mg (23% yield) of the desired product (7) as a fluffy white solid. $^1$H NMR (500 MHz, CDCl3): δ 7.64 (dd, J=12.0, 4.5 Hz, 1H), 7.52 (d, J=5.0 Hz, 1H), 7.49 (d, J=6.0 Hz, 1H), 7.47-7.44 (m, 1H), 7.39-7.28 (m, 4H), 6.83 (d, J=11.0 Hz, 2H), 5.60-5.54 (m, 1H), 5.00 (d, J=15.5 Hz, 1H), 4.55 (dd, J=16.0, 6.0 Hz, 1H), 4.36-4.14 (m, 6H), 3.94-3.92 (m, 6H), 3.89-3.72 (m, 2H), 3.26 (dt, J=15.5, 6.0 Hz, 1H), 3.15 (dt, J=15.0, 4.0 Hz, 1H), 3.10-3.00 (m, 1H), 2.95-2.84 (m, 1H), 2.41 (sextet, J=6.5 Hz, 2H), 1.69 (d, J=7.0 Hz, 3H). LC/MS: retention time 2.64 min. (ES+) calc for C36H37N4O6: [M+H]+ 621. found 621.

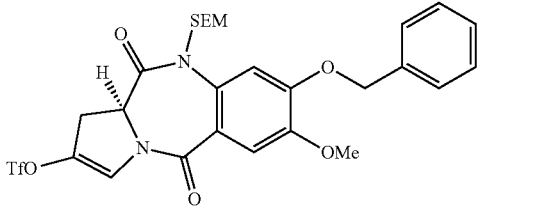

Trifluoro-methanesulfonic acid 8-benzyloxy-7-methoxy-5,11-dioxo-10-(2-trimethylsilanyl-ethoxymethyl)-5,10,11,11a-tetrahydro-1H-benzo[e]pyrrolo[1,2-a][1,4]diazepin-2-yl ester (18)

To an Ar purged solution of 8-benzyloxy-7-methoxy-10-(2-trimethylsilanyl-ethoxymethyl)-1,11a-dihydro-1 OH-benzo[e]pyrrolo[1,2-a][1,4]diazepine-2,5,11-trione (13) (8.3 g, 16.7 mmol) in DCM (200 mL), cooled to −45° C. in a dry ice/acetonitrile bath, added 2,6-lutidine (6.0 mL, 51.8 mmol) followed by the dropwise addition of triflic anhydride (8.4 mL, 50.1 mmol) while maintaining an internal temperature <−40° C. The reaction was stirred at −45° C. for 1 h, at which time the reaction was judged complete by TLC and LC/MS. The cold reaction mixture was diluted with DCM (200 mL), then washed with H₂O (100 mL), 5% citric acid (aq) (200 mL), sat. NaHCO3 (aq) (200 mL), and brine (100 mL). The organics were then dried over MgSO4, filtered, concentrated and the resulting residue was purified by column chromatography in 0-30% EtOAc in Hexanes to afford (18) as an off-white foam (9.8 g, 93% yield, 15.6 mmol). $^1$H NMR (500 MHz, CDCl3): δ 7.45-7.42 (m, 2H), 7.39-7.35 (m, 2H), 7.35-7.30 (m, 2H), 7.27 (s, 1H), 7.13 (t, J=2.0 Hz, 1H), 5.46 (d J=9.8 Hz, 1H), 5.21 (d, J=2.9 Hz, 2H), 4.61 (dd, J=11.0, 3.7 Hz, 1H), 4.54 (d, J=10.3 Hz, 1H), 3.95 (s, 3H), 3.90 (dq, J=16.1, 2.0 Hz, 1H), 3.71 (td, J=9.8, 7.3 Hz, 1H), 3.61 (td, J=9.8, 7.3 Hz, 1H), 3.14 (ddd, J=16.1, 10.7, 2.4 Hz, 1H), 2.57 (d, J=6.4 Hz, 1H), 0.97 (sep, J=3.4 Hz, 2H), 0.04 (s, 9H). LC/MS: retention time 4.20 min. (ES+) calc for C27H31F3N2NaO8SSi: [M+Na]+651. found 651.

Example 4

Cytotoxicity of CLT-D201, CLT-D501, and CLT-D601

Cytotoxic activity of compounds CLT-D201, CLT-D501, CLT-D601 was tested against various cell lines. Results of these tests are shown in FIGS. 10-18.

Example 5

Cytotoxicity of CLT-D201, CLT-D501, and CLT-D601 in Comparison with Pyrrolobenzodiazepine Dimer (PBD1)

The cytotoxic activity of compounds CLT-D201, CLT-D501, CLT-D601 was tested against various cell lines in comparison with a pyrrolobenzodiazepine dimer labeled as PBD1 (structurally identical to SGD-1882, Spirogen Ltd.), having a formula:

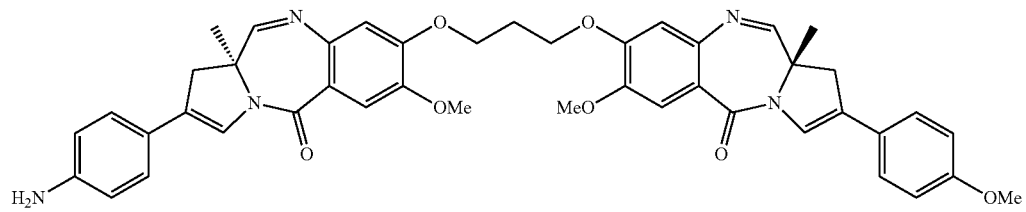 [SMILES: COc1ccc(C2=CN3C(=O)c4cc(OC)c(OCCCOc5cc6c(cc5OC)C(=O)N5C=C(c7ccc(N)cc7)C[C@@]5(C)C=N6)cc4N=C[C@]3(C)C2)cc1]

Figure 19:
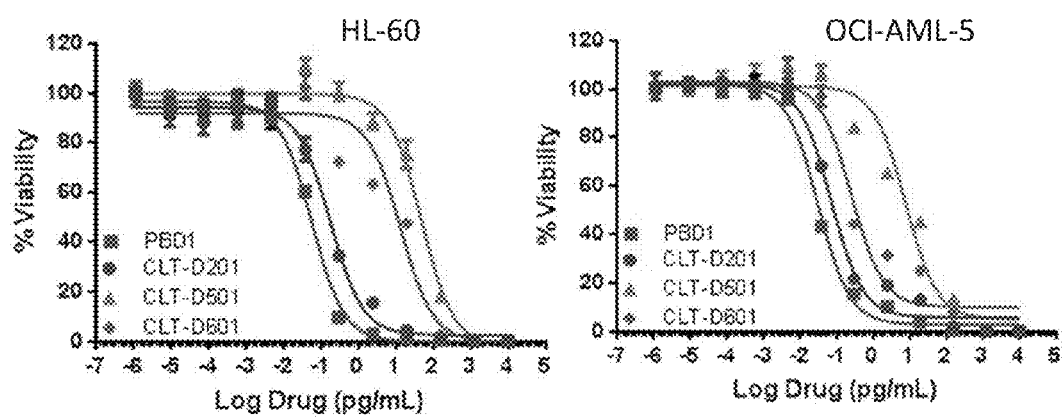
FIG. 19 shows a comparison between payload potency of CLT-D201 and PBD1.

FIG. 19 shows the curve of cytotoxic activity against HL-60 and PCI-AML-5 cell lines. Table 1 shows the IC$_{50}$ values for PBD1 and CLT-D201 respectively, for a larger group of cell lines. The results demonstrate that CLT-D201 payload potency is similar to that of PBD1 in AML cell lines.

TABLE 1

Summary of Growth Inhibition.

| IC50 pg/mL | PBD1 | D201 | MDR |
|---|---|---|---|
| OCI-AML5 | 2.084 | 8.235 | NA |
| HL-60 | 2.8 | 2.0 | – |
| SHI | 5.468 | 21.09 | – |
| THP-1 | 12.61 | 29.08 | – |

TABLE 1-continued

Summary of Growth Inhibition.

| IC50 pg/mL | PBD1 | D201 | MDR |
|---|---|---|---|
| HNT-34 | 1.494 | 14.02 | +/− |
| HEL92.1.7 | 3.866 | 40.41 | + |
| KG1 | 660 | 2454 | + |
| TF-1 | 447 | 1286 | + |

Example 6

Synthesis of CLT-D202

A synthesis scheme for CLT-D202 was performed as follows and is described in FIGS. 20A-D. Numbering is as in FIGS. 20A-D.

General Methods:
$^1$H NMR spectra were recorded on a Varian Inova 300 or 500 MHz NMR instrument. Chromatographic purities were determined on an Agilent 1200 Series or 1100 Series LC/MS system using a Merck Chromolith RP-18e analytical HPLC column (monolithic, 50×2 mm) and the following analytical HPLC method: injection volume 5 µL; flow rate 1 mL/min; 5-95% acetonitrile in water over 5 mins; Agilent diode array detector at λ=254, 220 or 195 nm; room temperature.

6.1: Preparation of (4-{3-[4-(3-hydroxymethyl-3,4-dihydro-1H-isoquinoline-2-carbonyl)-2-methoxy-5-nitro-phenoxy]-propoxy}-5-methoxy-2-nitro-phenyl)-(3-hydroxymethyl-3,4-dihydro-1H-isoquinolin-2-yl)-methanone (3, FIG. 20A)

To an Argon purged solution of 1'-3'-bis(4-carboxy-2-methoxy-5-nitrophenoxyl)propane (1) (11.63 g, 24.94 mmol) and DMF (1.3 mL) in DCM (134 mL) at 0° C., was added oxalyl chloride (6.33 mL, 74.83 mmol), dropwise. After initial effervescence was observed, the cold bath was removed and the reaction was stirred at 22° C. for 16 h. Conversion to the acid chloride was confirmed by treating a small aliquot of the reaction mixture with MeOH and the resulting bis-methyl ester was observed by LC/MS. The reaction was concentrated and then a small amount of dry DCM (10 mL) was added and the precipitate was triturated with cold Et₂O. The isolated solids were dried in a vacuum oven for 1 h at 40° C. The solid acid chloride was added portion-wise over 25 minutes to a solution of (±)-(1,2,3,4-tetrahydro-isoquinolin-3-yl)-methanol (2, FIG. 20A) (9.20 g, 56.4 mmol) and Et₃N (8.69 mL, 62.4 mmol) in DCM (100 mL) at −40° C. (dry ice/acetonitrile). Immediately, the reaction was judged complete by LC/MS. The mixture was diluted with DCM (500 mL) and washed with 1N HCl (300 mL), sat. NaHCO₃ (aq) (300 mL) and brine (300 mL). The mixture was then dried over MgSO$_4$, filtered and concentrated to afford (3) as yellow solid (16.4 g, 87% yield, 22.2 mmol).

$^1$H NMR (500 MHz, DMSO-d$_6$) δ=7.77 (br. s., 2H), 7.28-7.25 (m, 1H), 7.24-7.16 (m, 8H), 7.13 (br. s., 1H), 6.98 (d, J=7.8 Hz, 2H), 5.33 (d, J=16.1 Hz, 1H), 5.01-4.88 (m, 2H), 4.34-4.25 (m, 8H), 3.91 (s, 6H), 3.43 (br. s., 2H), 3.27-3.21 (m, 2H), 3.00 (d, J=1.5 Hz, 1H), 3.03-2.97 (m, 1H), 2.76 (d, J=2.9 Hz, 1H), 2.29 (t, J=6.1 Hz, 2H).

LC/MS: retention time 3.07 min. (ES$^+$) calc for C$_{39}$H$_{41}$N$_4$O$_{12}$: [M+H]$^+$ 757. found 757.

6.2: Preparation of acetic acid 2-(4-{3-[4-(3-acetoxymethyl-3,4-dihydro-1H-isoquinoline-2-carbonyl)-2-methoxy-5-nitro-phenoxy]-propoxy}-5-methoxy-2-nitro-benzoyl)-1,2,3,4-tetrahydro-isoquinolin-3-ylmethyl ester (4, FIG. 20A)

To an Argon purged solution of 4-{3-[4-(3-hydroxymethyl-3,4-dihydro-1H-isoquinoline-2-carbonyl)-2-methoxy-5-nitro-phenoxy]-propoxy}-5-methoxy-2-nitro-phenyl)-(3-hydroxymethyl-3,4-dihydro-1H-isoquinolin-2-yl)-methanone (3, FIG. 20A) (8.60 g, 11.4 mmol) in DCM (150 mL), added DMAP (194 mg, 1.59 mmol) and Et$_3$N (31.7 mL, 227 mmol). The mixture was then cooled to 0° C., and Ac$_2$O (21.5 mL, 227 mmol) was added. The cold bath was then removed and the reaction was stirred at 22° C. for 64 h. The reaction was judged complete by LC/MS and TLC, diluted with DCM (200 mL) and quenched with sat. NH$_4$Cl (aq) (200 mL). After splitting layers, the aqueous layer was further extracted with DCM (3×200 mL). The combined organics were washed with brine (300 mL), dried over MgSO$_4$, filtered, concentrated and purified by column chromatography in 0→100% EtOAc in hexanes to afford (4) as a yellow foam (8.12 g, 86% yield, 9.75 mmol).

$^1$H NMR (500 MHz, CDCl$_3$) δ=7.87-7.77 (m, 2H), 7.25-7.08 (m, 7H), 6.91-6.80 (m, 2H), 6.73-6.65 (m, 1H), 5.61 (d, J=17.6 Hz, 0.5H), 5.46 (d, J=17.6 Hz, 0.5H), 5.39-5.30 (m, 1H), 4.46-4.22 (m, 10H), 4.06-3.85 (m, 8H), 3.79 (d, J=9.3 Hz, 0.5H), 3.35-3.19 (m, 1H), 3.16-2.98 (m, 0.5H), 2.92 (dd, J=2.7, 16.4 Hz, 1H), 2.71 (t, J=14.2 Hz, 1H), 2.49 (t, J=5.9 Hz, 2H), 2.04-1.94 (m, 6H).

LC/MS: retention time 3.54 min. (ES$^+$) calc for C$_{43}$H$_{45}$N$_4$O$_{14}$: [M+H]$^+$ 841. found 841.

6.3: Preparation of (2-amino-4-{3-[5-amino-4-(3-hydroxymethyl-3,4-dihydro-1H-isoquinoline-2-carbonyl)-2-methoxy-phenoxy]-propoxy}-5-methoxy-phenyl)-(3-hydroxymethyl-3,4-dihydro-1H-isoquinolin-2-yl)-methanone (5, FIG. 20A)

To a solution of acetic acid 2-(4-{3-[4-(3-acetoxymethyl-3,4-dihydro-1H-isoquinoline-2-carbonyl)-2-methoxy-5-nitro-phenoxy]-propoxy}-5-methoxy-2-nitro-benzoyl)-1,2,3,4-tetrahydro-isoquinolin-3-ylmethyl ester (4, FIG. 20A) (500 mg, 0.595 mmol) in MeOH (20 mL), a small scoop of Raney® Ni was added. The mixture was then heated to reflux and hydrazine hydrate (370 µL, 11.9 mmol) in MeOH (3.5 mL) was added dropwise. Rapid effervescence was observed upon addition of hydrazine. Once the addition of hydrazine was completed, no further effervescence was observed upon further addition of Raney® Ni. The reaction was then refluxed an additional 9 h and the reaction was judged complete by LC/MS. (Note: Bis-nitro reduction occurs readily; additional reaction time is necessary to fully de-acylate the product). The reaction was removed from heat, filtered through celite, and washed with MeOH. The filtrate was concentrated in vacuo, and azeotroped with DCM. The crude residue was purified via column chromatography (0→10% MeOH in DCM) to afford (5) as a white crystalline solid (368 mg, 89% yield, 0.528 mmol).

$^1$H NMR (500 MHz, CDCl$_3$) δ=7.23-7.18 (m, 4H), 7.17-7.08 (m, 4H), 6.71 (s, 2H), 6.36 (d, J=4.9 Hz, 2H), 5.02 (br. s., 2H), 4.58 (br. s., 2H), 4.02 (br. s., 2H), 4.44 (d, J=16.6 Hz, 2H), 4.25 (t, J=5.9 Hz, 4H), 3.78 (s, 6H), 3.68-3.57 (m, 4H), 3.17 (dd, J=6.3, 16.6 Hz, 2H), 2.71 (d, J=17.1 Hz, 2H), 2.39-2.32 (m, 2H).

LC/MS: retention time 2.75 min. (ES$^+$) calc for C$_{39}$H$_{45}$N$_4$O$_8$: [M+H]$^+$ 697. found 697.

6.4: Preparation of [5-{3-[5-Amino-4-(3-hydroxymethyl-3,4-dihydro-1H-isoquinoline-2-carbonyl)-2-methoxy-phenoxy]-propoxy}-2-(3-hydroxymethyl-3,4-dihydro-1H-isoquinoline-2-carbonyl)-4-methoxy-phenyl]-carbamic acid allyl ester (6, FIG. 20A)

To an Ar purged solution of (2-amino-4-{3-[5-amino-4-(3-hydroxymethyl-3,4-dihydro-1H-isoquinoline-2-carbonyl)-2-methoxy-phenoxy]-propoxy}-5-methoxy-phenyl)-(3-hydroxymethyl-3,4-dihydro-1H-isoquinolin-2-yl)-methanone (5) (1.92 g, 2.75 mmol) in DCM (33 mL), was added pyridine (245 µL, 3.03 mmol) and the resultant solution was cooled n to 0° C. in an ice/brine bath, then AllocCl (292 µL, 2.75 mmol) was added. The mixture was then stirred at 0° C. for 30 min. The DCM was then removed in vacuo, the residue diluted with DMSO, and purified via reverse phase column chromatography (5→95% AcN in H$_2$O, each containing 0.05% AcOH) and desired fractions lyophilized to afford (6) as a white crystalline solid (417 mg, 19% yield, 0.534 mmol).

$^1$H NMR (300 MHz, CDCl$_3$) δ=8.10 (s, 1H), 7.66 (d, J=10.5 Hz, 1H), 7.24-7.09 (m, 9H), 6.80 (br. s., 1H), 6.68 (s, 1H), 6.38 (s, 1H), 5.99-5.85 (m, 1H), 5.33 (dd, J=2.3, 17.0 Hz, 1H), 5.22 (dd, J=2.3, 8.8 Hz, 1H), 5.04 (br. s, 2H), 4.61 (d, J=5.9 Hz, 2H), 4.48-4.36 (m, 2H), 4.34-4.22 (m, 4H), 3.82 (s, 3H), 3.79 (br. s., 1H), 3.77 (s, 3H), 3.74-3.59 (m, 4H), 3.18 (dd, J=6.1, 16.1 Hz, 2H), 2.82-2.65 (m, 2H), 2.41-2.35 (m, 2H).

LC/MS: retention time 3.01 min. (ES$^+$) calc for C$_{43}$H$_{49}$N$_4$O$_{10}$: [M+H]$^+$ 781. found 781.

6.5: Preparation of Bis-(tert-butyl-methoxy-dimethyl-silanyloxy)-ether of [5-{3-[5-Amino-4-(3-hydroxymethyl-3,4-dihydro-1H-isoquinoline-2-carbonyl)-2-methoxy-phenoxy]-propoxy}-2-(3-hydroxymethyl-3,4-dihydro-1H-isoquinoline-2-carbonyl)-4-methoxy-phenyl]-carbamic acid allyl ester (7, FIG. 20A)

To an Ar purged solution of ([5-{3-[5-Amino-4-(3-hydroxymethyl-3,4-dihydro-1H-isoquinoline-2-carbonyl)-2-methoxy-phenoxy]-propoxy}-2-(3-hydroxymethyl-3,4-dihydro-1H-isoquinoline-2-carbonyl)-4-methoxy-phenyl]-carbamic acid allyl ester (6, FIG. 20A) (417 mg, 0.534 mmol) in DMF (5.3 mL) was added imidazole (182 mg, 2.67 mmol). The reaction mixture was stirred for 5 min, followed by the addition of t-butyl dimethyl silyl chloride (TBSCl) (292 µL, 2.75 mmol). The resulting mixture was then stirred at 22° C. for 70 min. The reaction mixture was then poured onto ice/H$_2$O and extracted with EtOAc (3×20 mL). The combined organics were washed with H$_2$O (2×20 mL), dried over MgSO$_4$, filtered and concentrated. The resulting residue was purified via column chromatography in 0→100% EtOAc in hexane to afford (7) as a white solid (425 mg, 79%, 0.421 mmol).

$^1$H NMR (500 MHz, CDCl3) δ=8.36 (br. s., 1H), 7.90 (br. s., 1H), 7.22-7.12 (m, 8H), 7.08 (br. s., 1H), 6.84 (br. s., 1H), 6.76 (s, 1H), 6.37 (s, 1H), 5.97-5.88 (oct, J=5.4 Hz, 1H), 5.35 (d, J=3.4 Hz, 1H), 5.22 (dd, J=1.5, 10.3 Hz, 1H), 4.66-4.55 (m, 4H), 4.42 (br. s., 2H), 4.31 (t, J=6.1 Hz, 2H), 4.24 (t, J=6.6 Hz, 2H), 4.18 (br. s., 2H), 3.82 (s, 3H), 3.77 (s, 3H), 3.68 (br. s., 4H), 3.20-3.12 (m, 2H), 2.83 (d, J=16.1 Hz, 2H), 2.40 (quin, J=6.2 Hz, 2H), 0.85 (s, 18H), 0.00 (br. s., 12H)

LC/MS: retention time 5.07 min, (ES$^+$) calc for $C_{55}H_{77}N_4O_{10}Si_2$: [M+H]$^+$ 1009. found 1009.

6.6: Preparation of t-boc-N-amido-dPEG®$_8$-NHS ester (9, FIG. 20B)

To an Ar purged solution of t-boc-N-amido-dPEG®$_8$-acid (8, FIG. 20B) (1.00 g, 1.85 mmol) in DCM (20 mL), was added N-hydroxysuccinimide (255 mg, 2.22 mmol), N-(3-dimethylaminopropyl)-N'-ethylcarbodiimide hydrochloride (EDC*HCl) (531 mg, 2.77 mmol), and dimethylaminopyridine (DMAP) (10 mg, 0.0819 mmol). The combined mixture was stirred at 22° C. for 16 h. The reaction was then quenched with H$_2$O (20 mL), and extracted with DCM (3×30 mL). The combined organics were dried over MgSO$_4$, filtered and concentrated. The resulting residue was purified via column chromatography in 0→15% MeOH in DCM to afford (9) as a clear oil (856 mg, 73%, 1.34 mmol).

$^1$H NMR (500 MHz, CDCl3) δ=5.03 (br. s, 1H), 3.86 (t, J=6.6 Hz, 2H), 3.72-3.59 (m, 28H), 3.55 (t, J=5.1 Hz, 2H), 3.32 (q, J=5.4 Hz, 2H), 2.91 (t, J=6.6 Hz, 2H), 2.85 (br. s., 4H), 1.45 (s, 9H).

LC/MS: retention time 2.56 min. (ES$^+$) calc for $C_{28}H_{50}N_2O_{14}Na$: [M+Na]$^+$661. found 661.

6.7: Preparation of t-boc-N-amido-dPEG®$_8$-Val-Ala-acid (10, FIG. 20B)

To an Ar purged solution of t-boc-N-amido-dPEG®$_8$-NHS ester (9, FIG. 20B) (856 mg, 1.34 mmol) in DMF (6.7 mL) was added DIEA (584 μL, 3.35 mmol), followed by H$_2$N-Val-Ala-OH (278 mg, 1.48 mmol). The reaction was then stirred in a sealed vial at 40° C. for 16 h. The resulting reaction mixture was then directly loaded and purified via reverse phase column chromatography (5→95% ACN in H$_2$O, each containing 0.05% AcOH) and desired fractions lyophilized to afford (10) as a clear oil (717 mg, 75% yield, 1.01 mmol).

$^1$H NMR (500 MHz, CDCl3) δ=7.13 (br. s, 1H), 5.16 (br. s, 1H), 4.48 (br. s, 1H), 4.32 (dd, J=5.9, 8.8 Hz, 1H), 3.84-3.77 (m, 1H), 3.77-3.71 (m, 1H), 3.69-3.60 (m, 30H), 3.55 (t, J=4.9 Hz, 2H), 3.32 (br. d, J=4.9 Hz, 2H), 2.55 (t, J=5.6 Hz, 2H), 2.22 (qd, J=6.7, 13.2 Hz, 1H), 1.55-1.38 (m, 12H), 0.96 (dd, J=6.6, 17.3 Hz, 6H).

LC/MS: retention time 2.41 min.

(ES+) calc for C32H62N3O14: [M+H]+ 712. found 712.

6.7: Preparation of t-boc-N-amido-dPEG®$_8$-Val-Ala-4-aminobenzyl-alcohol (11, FIG. 20B)

To an Ar purged solution of t-boc-N-amido-dPEG®$_8$-Val-Ala-acid (10, FIG. 20B) (349 mg, 0.490 mmol) in 2:1 DCM/MeOH (7.45 mL) was added 4-aminobenzyl alcohol (69.4 mg, 0.564 mmol) followed by 2-ethoxy-1-ethoxycarbonyl-1,2-dihydroquinoline (EEDQ) (228 mg, 0.920 mmol). The reaction was stirred at 22° C. for 20 h. The reaction mixture was then concentrated in vacuo and purified by column chromatography (0→15% MeOH in DCM to afford (11) as a white solid (325 mg, 81% yield, 0.397 mmol).

$^1$H NMR (500 MHz, CDCl3) δ=8.58 (br. s., 1H), 7.71 (d, J=8.8 Hz, 2H), 7.31 (d, J=8.8 Hz, 2H), 6.99 (br. s., 1H), 6.87 (br. s., 1H), 5.11-5.06 (m, 1H), 4.68 (t, J=7.8 Hz, 1H), 4.64 (d, J=6.3 Hz, 2H), 4.22 (dd, J=5.6, 6.6 Hz, 1H), 3.86 (dt, J=3.4, 9.8 Hz, 1H), 3.71-3.58 (m, 29H), 3.53 (t, J=5.1 Hz, 2H), 3.33-3.29 (m, J=5.4 Hz, 2H), 2.71-2.63 (m, 1H), 2.49 (ddd, J=3.2, 5.6, 14.7 Hz, 1H), 2.34-2.26 (m, 1H), 1.81 (t, J=5.9 Hz, 1H), 1.48-1.44 (m, 12H), 1.01 (dd, J=6.8, 15.6 Hz, 6H).

LC/MS: retention time 2.52 min. (ES$^+$) calc for $C_{39}H_{68}N_4O_{14}Na$: [M+Na]+839. found 839.

6.7: Preparation of linker bound, fully protected cytotoxic dimer drug (13, FIG. 20C)

To an Ar purged solution of t-boc-N-amido-dPEG®$_8$-Val-Ala-4-aminobenzyl-alcohol (11, FIG. 20B) (285 mg, 0.348 mmol) in DMF (1.7 mL) was added diisopropyldiethylamine (DIEA) (91 μl (285 mg, 0.348 mmol) in DMF (1-(pentafluorophenyl)-carbonate (204 mg, 0.523 mmol). The reaction was then stirred at 22° C. for 2 h, at which time, the resulting reaction was judged complete by LC/MS, yielding activated intermediate cpd, 12 (FIG. 20B)

LC/MS: retention time 3.41 min, (ES$^+$) calc for $C_{46}H_{67}F_5N_4O_{16}Na$: [M+Na]$^+$1049. found 1049.

Figure 20A:
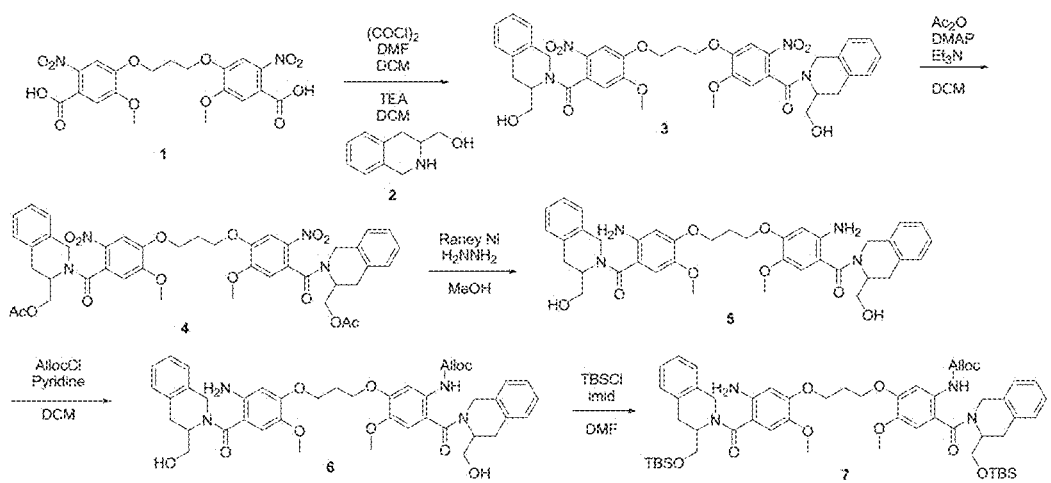
Figure 20B:
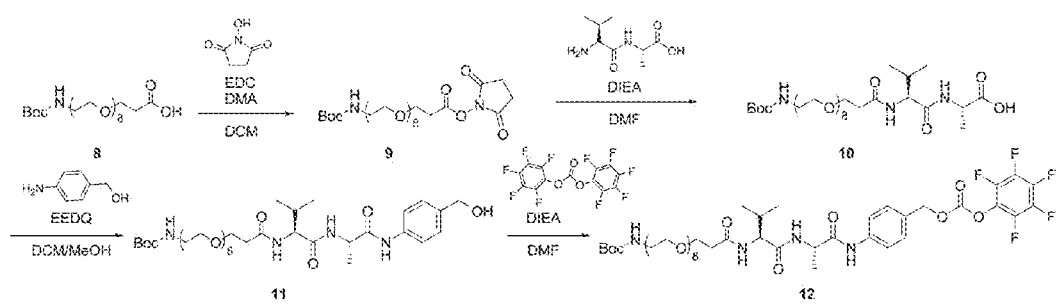

The crude solution of 12 (the product from FIG. 20B) was added to solid bis-(tert-butyl-methoxy-dimethyl-silanyloxy)-ether of [5-{3-[5-Amino-4-(3-hydroxymethyl-3,4-dihydro-1 H-isoquinoline-2-carbonyl)-2-methoxy-phenoxy]-propoxy}-2-(3-hydroxymethyl-3,4-dihydro-1H-isoquinoline-2-carbonyl)-4-methoxy-phenyl]-carbamic acid allyl ester (7, the product from FIG. 20A) (176 mg, 0.174 mmol) as shown in FIG. 20C. The flask was then rinsed with an additional 300 mL of DMF to ensure a complete transfer of (12) to the reaction mixture. DIEA (91 μl to the reaction mixture. DIEA (91 additional 300 mL of DMF to ensure a complete transfer of (ydroxymethyl-3,4-dihydro-1H-isoquinoline-2-carbonyl)-2-methoxy-phenoxy]-propoxy}-2-(3-hydroxymethyl-3,4-dihydro-1H-isoquinoline-2-carbonyl)-4-methoxy-phenyl]-ca ACN in H$_2$O, each containing 0.05% AcOH) and desired fractions lyophilized to afford (13) as a white solid (153 mg, 47% yield, 0.0825 mmol).

LC/MS: retention time 4.99 min. (ES$^+$) calc for $C_{95}H_{142}N_8O_{25}Si_2$: 1851. found [{(M+H)/2}+Na]+949.

6.9: Preparation of linker bound, bis-alcohol compound. 14 (FIG. 20C)

To an Ar purged solution of (13) (153 mg, 0.0825 mmol) in THF (8.3 mL), cooled to 0° C. in an ice/brine bath was added TBAF (173 μL of a 1.0M solution in THF, 0.173 mmol). The reaction was then stirred at 0° C. for 16 h. The THF was then removed in vacuo, the residue diluted with dimethylsulfoxide (DMSO), and purified via reverse phase column chromatography (5→95% AcN in H$_2$O, each containing 0.05% AcOH) and desired fractions lyophilized to afford (14) as a white crystalline solid (116 mg, 87% yield, 0.0717 mmol).

LC/MS: retention time 3.38 min. (ES$^+$) calc for $C_{83}H_{114}N_8O_{25}Na$: [M+Na]$^+$1645. found 1645.

6.10: Preparation of linker bound, hemi-aminal compound. 15 (FIG. 20C)

To an Ar purged solution of (14, FIG. 20C) (108 mg, 0.0665 mmol) in 3:1 DCM/ACN (1.2 mL) was added 4 Å molecular sieves (5.0 mg), then N-methylmorpholine-N-oxide (NMO) (31.2 mg, 0.266 mmol) in 100 μL DCM. The reaction mixture was stirred for 15 min, then TPAP (5.8 mg, 0.0166 mmol) in 100 μL DCM was added. The resulting mixture was stirred at 22° C. for 1 h and the reaction was judged incomplete by LC/MS. Successive addition of NMO (10.4 mg, 0.0888 mmol) and TPAP (1.90 mg, 0.00541 mmol), each in 100 μL DCM was added to the reaction and the reaction was monitored by LC/MS after 1 h of addition until such time that the reaction was judged complete, monitoring the amount of starting material, desired product, mono oxidation and amide formation; in total, 5 subsequent additions were made. The solvents were then removed in vacuo, the residue diluted with DMSO, and purified via reverse phase column chromatography (5→95% ACN in H$_2$O, each containing 0.05% AcOH) and desired fractions lyophilized to afford (15) as a white crystalline solid (50.7 mg, 47% yield, 0.0313 mmol).

LC/MS: retention time 3.33 min. (ES$^+$) calc for C$_{83}$H$_{110}$N$_8$O$_{25}$Na: [M+Na]1641. found 1641.

Figure 20D:
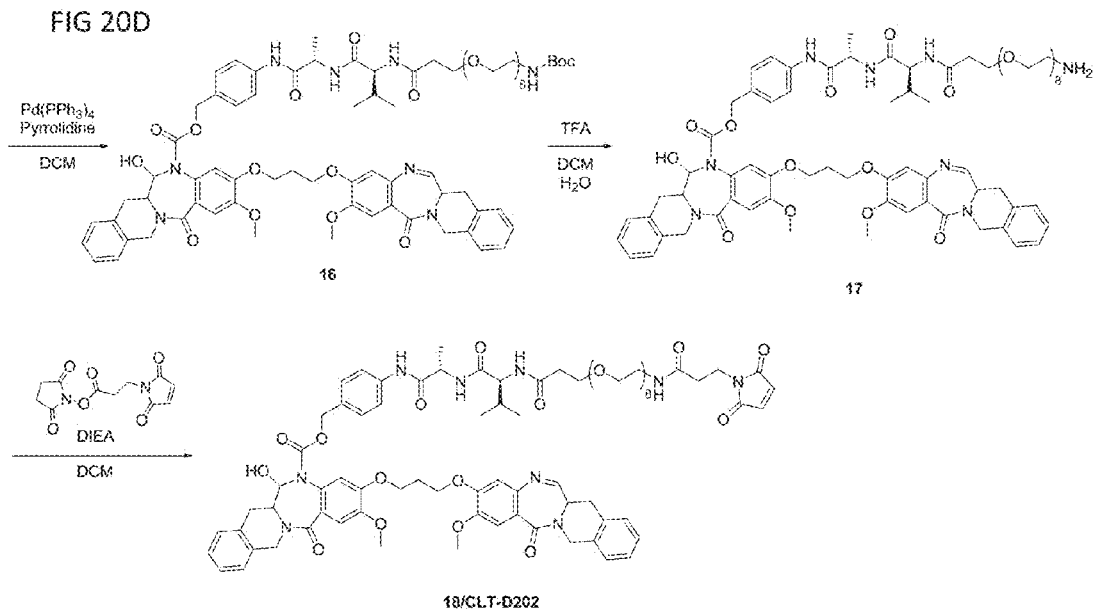

6.11: Preparation of linker bound, mono-imine compound 16 (FIG. 20D)

To an Ar purged solution of (15) (15.7 mg, 0.00969 mmol) in DCM (1.0 mL) was added pyrrolidine (1.2 μL, 0.0145 mmol) in 50 μL DCM followed by Pd(PPh$_3$)$_4$(0.56 mg, 0.485 μmol) in 50 μL DCM. The reaction was then stirred at 22° C. for 1 h. The DCM was then removed in vacuo, the residue diluted with DMSO, and purified via reverse phase column chromatography (5→95% AcN in H$_2$O, each containing 0.05% AcOH) and desired fractions lyophilized to afford (16) as a white crystalline solid (8.2 mg, 56% yield, 0.00540 mmol).

LC/MS: retention time 3.23 min. (ES$^+$) calc for C$_{79}$H$_{104}$N$_8$O$_{22}$Na: [M+Na]+1539. found 1539.

6.12: Preparation of CLT-D202 (18, FIG. 20D)

To an Ar purged solution of (16, FIG. 20C) (3.5 mg, 0.00231 mmol) in DCM (0.50 mL), cooled to 0° C. in the refrigerator for 30 min, was added a precooled solution of 47:47:6 solution of TFA/DCM/H$_2$O (200 μl). The reaction was left standing at 0° C. for 2 h. The DCM was then removed in vacuo, the residue diluted with 1:1 ACN/H$_2$O and lyophilized to afford (17 FIG. 20D) as a white crystalline solid which was used without further purification.

LC/MS: retention time 2.56 min. (ES$^+$) calc for C$_{74}$H$_{97}$N$_8$O$_{20}$: [M+H]$^+$ 1417. found 1417.

To an Ar purged solution of crude (17) in DCM (0.5 mL), added DIEA (2.4 μL, 0.0143 mmol) in 200 μL DCM, checked pH of the reaction mixture; pH>8. A solution of 3-maleimidopropionic acid NHS ester (1.0 mg, 3.57 μmol) in 100 μL DCM was then added to the reaction. The reaction was stirred at 22° C. for 75 min. The DCM was then removed in vacuo, the residue diluted with DMSO, and purified via reverse phase column chromatography (5→95% AcN in H$_2$O, each containing 0.05% AcOH) and desired fractions lyophilized to afford (18) as a white crystalline solid (1.3 mg, 36% yield over 2 steps, 0.829 μmol).

LC/MS: retention time 2.94 min. (ES$^+$) calc for C$_{81}$H$_{102}$N$_9$O$_{23}$: [M+H]$^+$ 1568. found 1568.

Example 7

Preparation of C6-CLT-D202 (Antibody-Drug Conjugate)

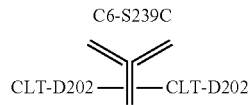

A humanized, cys-substituted at position 239 anti-CLL1 antibody ("C6-S239C-CYSM26") (5.0 mg, 1.68 mg/mL, PBS) was exchanged into borate buffer (50 mM, pH 8.5, 1 mM diethylene triamine pentaacetic acid (DTPA)) via 2 cycles of molecular weight cut-off filtration (MWCO) using a Millipore, 15 mL, 30 kDa device. To the new solution of the C6-S239C-CYSMAB antibody (5.0 mg/mL, borate buffer (50 mM, pH 8.5, 1 mM DTPA)) was added a solution of Dithiothreitol (DTT) (33 μL, 50.0 equiv., 50 mM) and the resultant solution was shaken gently overnight.

Antibody C6 has the light chain variable region sequence: LQQKPGKAIKRLIYAASTLDSGVPSRFSGSGSGTDYTLTISSLQPEDFATYYCI GTKLEIK (SEQ IS NO:1). Antibody C6 has the heavy chain variable region sequence: EVQLVQSGAEVKKP-GASVKMSCKASGYTFTSYFIHWVRQAPGQGLEWIG-FINPYNDGSKYAQ KFQGRATLTSDKSTSTVYMELSS-LRSEDTAVYYC (SEQ ID NO:2).

Complete reduction of the interchain disulfide bridges and removal of the S239C cysteine/glutathione adducts were was confirmed by rp-LCMS as described earlier (Junutula et al., 2008, Nature Biotech, 26, 925-932). DTT was then removed from the solution via 3 cycles of molecular weight cut-off filtration (MWCO) using a Millipore, 15 mL, 30 kDa device, using PBS as the exchange buffer. To a 5 mg/ml solution of the fully reduced C6-S239C-CYSMAB antibody was added a solution of dehydro ascorbic acid (dhAA) (33 μL, 50.0 equiv., 50 mM). The resultant solution was shaken gently for 3 hrs. The re-oxidation was monitored via rp-LCMS. Once the re-oxidation was deemed complete, the reaction mixture was diluted up to 50% v/v with propylene glycol and CLT-D202 (18, FIG. 20D) was added as a solution in DMSO (10.0 equiv., 10 mM in DMSO). The reaction was allowed to stir at ambient temperature for 1 hr. The mixture was then treated with activated charcoal for 1 hr at ambient temperature. The activated charcoal was then removed via filtration. The conjugate was then exchanged into PBS via multiple cycles of molecular weight cut-off filtration (MWCO) using Millipore, 15 mL, 30 kDa devices. The solution was then subjected to a sterile filtration to yield the desired conjugate (0.974 mL, 2.16 mg/mL). Volume: 0.974 mL. Concentration: 2.16 mg/mL (A$_{280}$=0.145, 20-fold dilution). Drug to Antibody Ratio (DAR): 1.7 (determined by rp-LCMS). The monomeric form of ADC is confirmed by size exclusion chromatography (SEC): 96%.

Example 8

Preparation of C0-CLT-D202 Antibody-Drug Conjugate (ADC)

Palivizumab was used a control antibody, C0. C0 antibody is a non-binding control IgG1. An ADC with C0 and CLT-D202 was The C0 antibody (12.0 mg, 100 mg/mL, PBS) was diluted to 5 mg/mL using borate buffer (50 mM, pH 8.5, 1 mM DTPA). In order to conjugate CLT-D202, the hinge disulfides were reduced, as follows. To the new solution of the C0 antibody (@5.0 mg/mL, borate buffer (50 mM, pH 8.5, 1 mM DTPA)) was added a solution of tris(2-carboxyethyl)phosphine (TCEP) (136 µL, 1.7 equiv., 1 mM) and the resultant solution was shaken gently at 37° C. for 1 hr. The reaction was then cooled to ambient temperature and was diluted up to 50% v/v with propylene glycol at which point CLT-D202 (18, FIG. 20D) was added as a solution in DMSO (12.0 equiv., 10 mM in DMSO). The reaction was allowed to stir at ambient temperature for 1 hr. The mixture was then treated with activated charcoal for 1 hr at ambient temperature. The activated charcoal was then removed via filtration. The conjugate was then exchanged into PBS via PD-10 gel filtration (GE Healthcare). The combined fractions were concentrated using molecular weight cut-off filtration (MWCO) with Millipore, 15 mL, 30 kDa devices. The solution was then subjected to a sterile filtration to yield the desired conjugate (3.144 mL, 3.2 mg/mL). Volume: 3.144 mL. Concentration: 3.2 mg/mL ($A_{280}$=0.237, 20-fold dilution). Drug to Antibody Ratio (DAR): 2.6 (determined by rp-LCMS). The monomeric form of ADC is confirmed by SEC: 87%.

Example 9

C6-CLT-D202 ADC Selective Cytotoxicity

Figure 21:
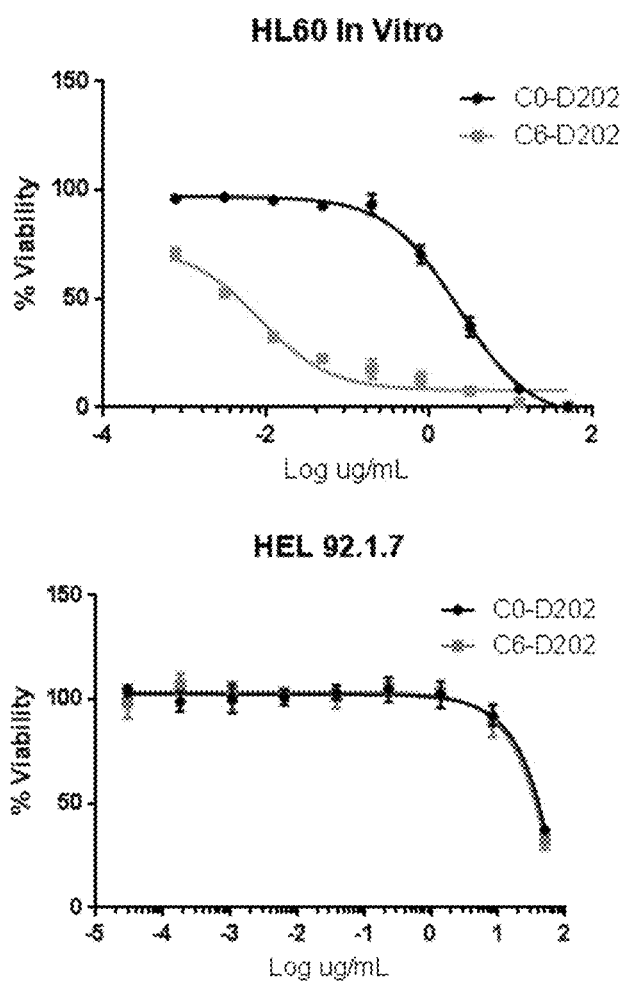
FIG. 21 shows target dependent cell killing of an anti-CLL1-D202 conjugate.

The selectivity of the C6-CLT-D202 ADC is shown in FIGS. 21A-21B. HL-60 cells (human promyelocytic leukemia cells) which express CLL-1 in the range of about 30,000-50,000 copy number per cell, were treated with the CLL-1 selective cytotoxic antibody-drug conjugate, C6-CLT-D202 ADC and the control antibody-drug conjugate, C0-D202 ADC, at varying concentrations at 37° C. for five days. FIG. 21A shows target dependent cell killing by C6-CLT-D202 ADC relative to that of the control C0-CLT-D202 ADC by over 500 fold. FIG. 21B shows that for non-CLL-1 expressing cell lines such as TF1 (human erythroleukemic cell line), both C6-CLT-D202 ADC and C-CLT-D202 ADC had similar, non-cytotoxic effect, thus demonstrating the selectivity of the CLL-1 targeted C6-CLT-D202 ADC in vitro.

Example 10

C6-CLT-D202 ADC Target Dependent Cytotoxicity

Figure 22A:
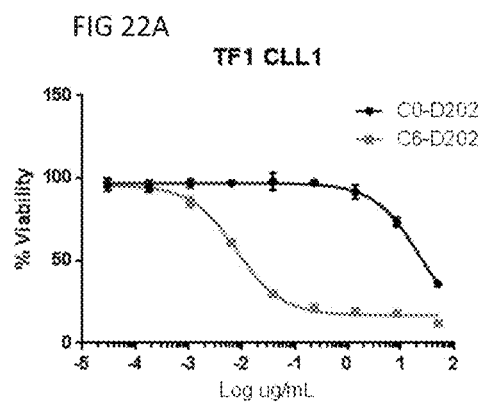
FIGS. 22A and 22B show a CLL1-ADC displayed target dependent cell killing in MDR+ve cell line.
Figure 22B:
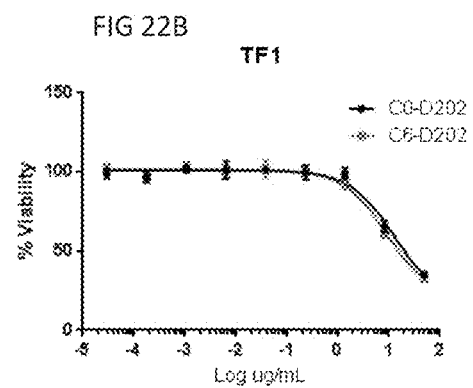

TF1 is a multi-drug resistant (MDR) positive acute myeloid leukemia (AML) cell line. CLL-1 was overexpressed in TF1 to demonstrate the potency of an antibody-drug conjugate comprising an anti-CLL1 antibody ("CLL1-ADC" or, more specifically, "C6-CLT-D202 ADC"). As shown in FIGS. 22A and 22B, the over-expressing TFI cell line (TF1-CLL1) and the standard TF1 cell line were treated at 37 C at various concentrations with C6-CLT-D202 ADC and C0-CLT-D202 ADC, respectively. In FIG. 22A, the CLL-1 targeted C6-CLT-D202 ADC was shown to be potently cytotoxic to the TF1 CLL-1 MDR (+) line, while the control C0-CLT-D202 ADC had a much less potent effect. The activity against the standard TF1 cell line for each ADC are shown in FIG. 22B, where it is seen that both the C6-CLT-D202 ADC and C0-CLT-D202 ADC had more similar effect. The $IC_{50}$ results shown in Table 3 demonstrate the significant difference in cell killing effect when CLL-1 is expressed in a tumor cell target, providing a decrease in IC50 by a factor of about $10^3$.

TABLE 2

IC50 for selected ADCs against TF1 CLL-1 and TF1 cell lines.

| $IC_{50}$ ug/mL | C0-D202 | C6-D202 |
|---|---|---|
| TF1-CLL1 | 23.27 | 0.008 |
| TF1 | 12.93 | 9.47 |

Example 11

Correlation Between Binding and Cytotoxicity for C6-CLT-D202 ADC

Figure 23:
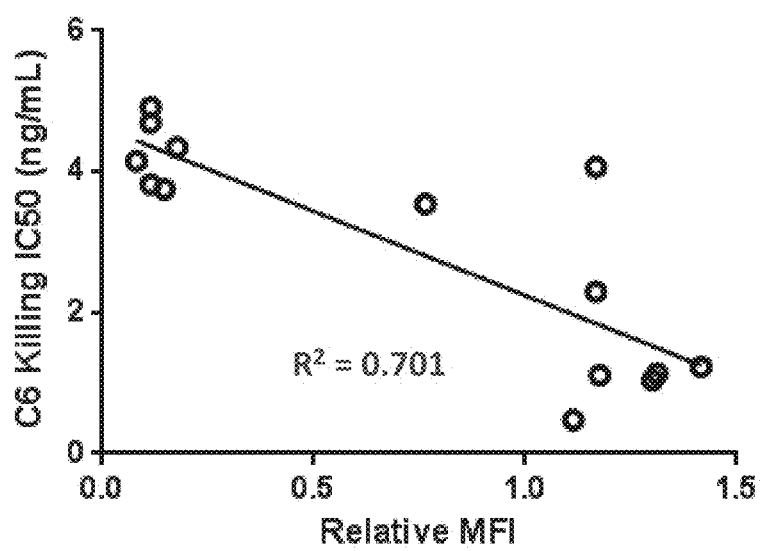
FIG. 23 shows a comparison of killing and binding of a CLL1-ADC.

The correlation between binding to cells and ability to kill targeted cells was examined. In Table 4, the first column of numbers is the ratio of the mean fluorescent intensity of binding of C6-CLT-D202 ADC to each specific cell line, relative to the mean fluorescent intensity of binding of C0-CLT-D202 ADC, which is the control ADC. A larger ratio of MFI reflects increased binding of the targeted ADC over that of the control ADC. The second column shows the IC50 (ng/mL) for C6-CLT-D202 ADC for the specified cell line. In FIG. 23, the two numbers are mapped, the log of the relative mean fluorescent index (MFI) along the X axis and the log of the IC50 value along the Y axis, for each cell line. FIG. 23 shows good correlation of relative binding vs cell killing, where $R^2$ of the fit of line shown is 0.701. This demonstrates that C6-CLT-D202 has good target-dependent cytotoxic activity across many cell lines associated with AML disease.

TABLE 3

Cell lines, Relative Binding Intensity, and $IC_{50}$s.

| Cell line | C6 relative MFI C6/C0 | C6-D202 IC50 ng/mL |
|---|---|---|
| AML2 | 13 | 3 |
| HL-60 | 20 | 11 |
| AML5 | 15 | 13 |
| AML5KO | 1.3 | 6621 |
| 293 | 1.2 | 14270 |
| U937 | 14.7 | 11690 |
| SHI-1 | 1.4 | 5670 |
| KG-1a | 1.3 | 82760 |
| HEL92.1.7 | 1.3 | 50000 |
| HEL92.1.7-CLL1 | 26.1 | 17 |
| HNT-34 | 5.8 | 3500 |
| TF1 | 1.5 | 22230 |
| EOL-1 | 20.5 | 13.7 |
| PL21 | 14.7 | 199 |

Example 12

C6-CLT-D202 ADC Targets Both Proliferating and Quiescent Cells

AML-5 cells, which express CLL-1, are cultured under either proliferative or quiescent conditions for a period of five (5) days. During this period, one set of proliferative CLL-1-expressing cells was treated with varying concentrations of C6-CLT-202 ADC. A second set of proliferative CLL-1-expressing cells was treated with isotype control. A respective set of quiescent CLL-1-expressing cells were treated accordingly with either C6-CLT-D202 or isotype control. FIG. 24A shows that C6-CLT-D202 was effective at killing CLL-1-expressing cells at an $IC_{50}$ of 0.03 ug/mL (proliferating) and 0.02 ug/mL (quiescent) cells, while the isotype control had an $IC_{50}$ of at least 100-fold higher concentration. Quiescent cell killing increases with increasing incubation times.

In contrast, as shown in FIG. 24B, when CLL-1-knockout cells were subjected to the same conditions, the target dependent cytotoxic effect of C6-CLT-D202 ADC is eliminated. The $IC_{50}$ for both proliferating and quiescent AML-5 cells are similar to that of the isotype control, in the range of 2.34 ug/mL (quiescent) and 5.54 ug/mL (proliferating).

etry using anti-human CD33 and CD45 antibodies. Data were analyzed by Flowjo software, and plotted with Prism software.

Figure 25A:
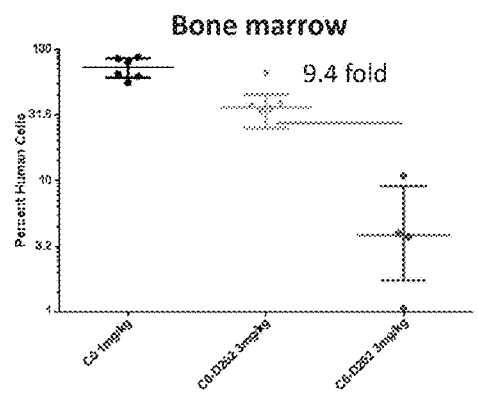
FIGS. 25A-25B shows results of in vivo tests of a CLL1-ADC.
Figure 25B:
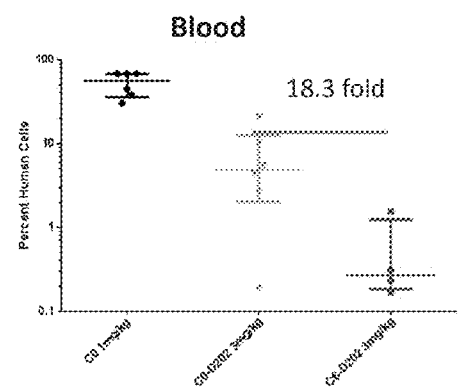

The treatment with C6-CLT-D202 ADC showed robust efficacy as shown in FIGS. 25A-25B and in Table 5. C6-CLT-D202 ADC animals treated with a 3 mg/kg level of ADC showed significant decreases in the percent human cells present in the bone marrow (FIG. 25A) and blood (FIG. 25B) respectively compared to control antibody alone (C0 Ab at 1 mg/kg) or C0-CLT-D202 ADC (at an equivalent 3 mg/kg dosage). In bone marrow, a 9.4 fold decrease in numbers of human xenograft cells were present in C6-CLT-D202 ADC treated animals, and in blood, an 18.3 fold decrease in number of human xenograft cells were observable, relative to that seen after administration with C0-CLT-D202 ADC. Greater than 90% Tumor Growth Inhibition (TGI) was observed after administration with C6-CLT-D202 ADC.

TABLE 5

Concentrations of Hu cells present after treatment.

| | Bone marrow | | | Blood | | |
|---|---|---|---|---|---|---|
| | C0 1 mg/kg | C0-D202 3 mg/kg | C6-D202 3 mg/kg | C0 1 mg/kg | C0-D202 3 mg/kg | C6-D202 3 mg/kg |
| Minimum | 55.9 | 0.942 | 1.07 | 30.4 | 0.188 | 0.168 |
| 25% Percentile | 60.85 | 25.2105 | 1.7375 | 36.025 | 2.0345 | 0.184 |
| Median | 72.95 | 36.15 | 3.85 | 56.5 | 4.955 | 0.271 |
| 75% Percentile | 85.8 | 45.125 | 9.09 | 68.1 | 12.625 | 1.2475 |

Example 13

C6-CLT-D202 ADC Efficacy In Vivo

C6-CLT-D202-ADC exhibit robust efficacy in AML xenograft models. Orthotopically engrafted HL60 tumor-bearing mice were treated with unconjugated C0 (1 mg/Kg) antibody and control ADC (3 mg/Kg) as compared with mice treated with C6-CLT-D202-ADC (3 mg/Kg). The percentage of human HL60 tumor cells in the bone marrow (left panel) and in the peripheral blood (right panel) is shown, the median bar and interquartile error bars are denoted for N=4-6 mice. The table (bottom) indicates the median, minimum, maximum, and interquartile percentage of human HL60 cells in the bone marrow and peripheral blood of treated mice.

Female 6-8 week-old NOD/SCID mice were sub-lethally irradiated with 2.5 Gy, and 5 million HL60 tumors were injected intravenously at one day post-irradiation into the mice. Following 6 days of tumor cell inoculation (~0.1-1% engraftment in the bone marrow), mice were dosed 3 times, and once per week (q7DX3) with 3 mg/Kg of C6-CLT-D202 ADC or with the same amount of control C0-ADC. Following 23 days of tumor cell inoculation, bone, spleen, and peripheral blood were collected from the treated mice and total hematopoietic cells were isolated. The percentage of human cells in these tissues was determined by flow cytom- Example 14

Effect of C6-CLT-D202 ADC on Primary AML Patient Cell Cultures

As shown in FIG. 26, increasing concentrations of C6-CLT-D202 ADC, from 0.8 ug/mL to 2 ug/mL had increasing effect in inhibiting colony formation in a primary AML patient cell culture, 14-AML-17. The control C0-CLT-D202 ADC had much less ability to inhibit colony formation in the same primary cell cultures. Number of colonies is represented on the Y axis.

All publications and patent applications mentioned in this specification are herein incorporated by reference to the same extent as if each individual publication or patent application were specifically and individually indicated to be incorporated by reference.

From the foregoing it will be appreciated that, although specific embodiments of the invention have been described herein for purposes of illustration, various modifications may be made without deviating from the spirit and scope of the invention. Accordingly, the invention is not limited except as by the appended claims.

SEQUENCE LISTING

<160> NUMBER OF SEQ ID NOS: 2

<210> SEQ ID NO 1
<211> LENGTH: 72
<212> TYPE: PRT
<213> ORGANISM: Homo sapiens

<400> SEQUENCE: 1

Leu Gln Gln Lys Pro Gly Lys Ala Ile Lys Arg Leu Ile Tyr Ala Ala
1               5                   10                  15

Ser Thr Leu Asp Ser Gly Val Pro Ser Arg Phe Ser Gly Ser Gly Ser
            20                  25                  30

Gly Thr Asp Tyr Thr Leu Thr Ile Ser Ser Leu Gln Pro Glu Asp Phe
        35                  40                  45

Ala Thr Tyr Tyr Cys Leu Gln Tyr Ala Ile Tyr Pro Tyr Thr Phe Gly
    50                  55                  60

Gln Gly Thr Lys Leu Glu Ile Lys
65                  70

<210> SEQ ID NO 2
<211> LENGTH: 96
<212> TYPE: PRT
<213> ORGANISM: Homo sapiens

<400> SEQUENCE: 2

Glu Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Phe Ile His Trp Val Arg Gln Ala Pro Gly Gln Gly Leu Glu Trp Ile
        35                  40                  45

Gly Phe Ile Asn Pro Tyr Asn Asp Gly Ser Lys Tyr Ala Gln Lys Phe
    50                  55                  60

Gln Gly Arg Ala Thr Leu Thr Ser Asp Lys Ser Thr Ser Thr Val Tyr
65                  70                  75                  80

Met Glu Leu Ser Ser Leu Arg Ser Glu Asp Thr Ala Val Tyr Tyr Cys
            85                  90                  95

30. A compound of the formula:
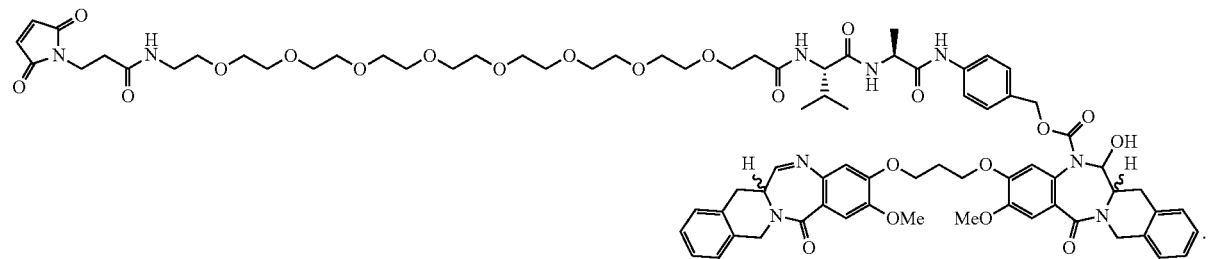

What is claimed is:

1. A method of treating acute myeloid leukemia (AML) comprising administering to a subject having AML a therapeutically effective amount of a compound having a structure of Formula (I):

(I)

wherein:
the dotted bond shown between —C($R^a$)— and —N($R^b$)— or —C($R^{a'}$)— and —N($R^{b'}$)— is independently a single bond or a double bond;
each of $R^a$ and $R^{a'}$ is independently H or OH;
each of $R^b$ and $R^{b'}$ is not present or is H;
$R^2$, $R^{2'}$, $R^3$, $R^{3'}$, $R^4$, $R^{4'}$, $R^{6'}$ and $R^6$ are each independently selected from H, OH, $C_1$-$C_{10}$ alkyl, $C_2$-$C_{10}$ alkenyl or $C_2$-$C_{10}$ alkynyl;

each of $R^5$ or $R^{5'}$ is independently $NH_2$, $CO_2H$, H, OH, $C_1$-$C_{10}$ alkyl, $C_2$-$C_{10}$ alkenyl or $C_2$-$C_{10}$ alkynyl;

each of $R^7$ and $R^{7'}$ is H;

X is:
- $C_{1-12}$ alkylene, optionally wherein the alkylene chain is interrupted by one or more hetero atoms selected from the group consisting of O, S, and NH; or
- —$(CH_2)_m$-Q-$(CH_2)_p$—, wherein m and p are each independently 0, 1 or 2;

Q has a structure of formula:

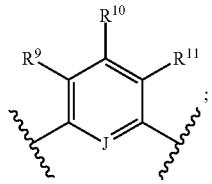

wherein each of $R^9$, $R^{10}$ and $R^{11}$ is H, $NH_2$ or $CO_2H$; and

J is CH or N;

each of Y and Y' is independently O, S, or NH;

each of Z and Z' is independently H, R, OH, OR, SH, SR, $NH_2$, or NHR, where each R is independently unsubstituted $C_1$-$C_{12}$ alkyl.

2. The method according to claim 1, wherein Y and Y' are each O.

3. The method according to claim 1, wherein Z and Z' are each independently OR, where each R is independently unsubstituted $C_1$-$C_3$ alkyl.

4. The method according to claim 1, wherein X is —$CH_2$—.

5. The method according to claim 1, wherein
each of $R^a$ and $R^{a'}$ is independently H, or OH;
if present, each of $R^b$ and $R^{b'}$ is H;
$R^2$, $R^{2'}$, $R^3$, $R^{3'}$, $R^4$, $R^{4'}$, $R^5$, $R^{5'}$, $R^{6'}$, $R^6$, $R^7$ and $R^{7'}$, are each H;
X is $C_{1-12}$ alkylene;
each of Y and Y' is O;
each of Z and Z' is independently OR, where each R is independently unsubstituted $C_1$-$C_3$ alkyl.

6. The method according to claim 1, wherein the compound has the structure:

7. A method of treating acute myeloid leukemia (AML) comprising administering to a subject having AML a therapeutically effective amount of an antibody-drug conjugate having a structure of Formula III:

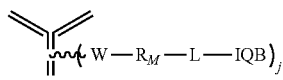

Formula III wherein:

is an antibody or antibody fragment that binds to a cancer marker on an AML cell;

W—$R_M$ is a linking moiety formed by W and $R_x$, wherein W is a moiety attached to a natural or unnatural amino acid residue of the antibody/antibody fragment and $R_x$ is a reactive moiety linking L-IQB to the antibody wherein $R_x$ is selected from iodoacetamide, succinimidyl, maleimidyl, cyclooctynyl, aminooxy, bisulfonyl, sulfonyl, or isothiocyanate moiety, such that W—$R_M$ is a disulfide, a thiolated succinimidyl, an amino substituted succinimidyl, a (cyclooctyl)-1, 4 triazolyl, oxime substituted N-glycan, oxime, a substituted bis-sulfopropyl, a sulfonamidyl, an amide, or a thiocarbamate moiety;

L is a linker comprising polyethylene glycol and 1-10 amino acid moieties; and,

IQB is a compound having a structure of Formula (I):

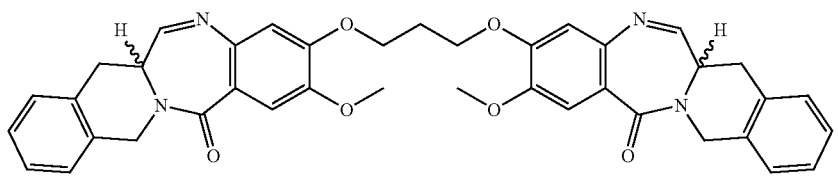

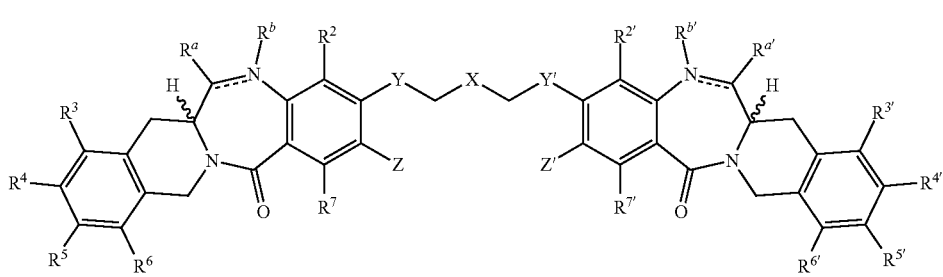

wherein:
- the dotted bond shown between —C(R$^a$)— and —N(R$^b$)— or —C(R$^{a'}$)— and —N(R$^{b'}$)— is independently a single bond or a double bond;
- each of R$^a$ and R$^{a'}$ is independently H, OH, or —O—P, where P is a protecting group;
- each of R$^b$ and R$^{b'}$ is not present or is independently H, or -L;
- R$^2$, R$^{2'}$, R$^3$, R$^{3'}$, R$^4$, R$^{4'}$, R$^{6'}$ and R$^6$ are each independently selected from H, OH, C$_1$-C$_{10}$ alkyl, C$_2$-C$_{10}$ alkenyl or C$_2$-C$_{10}$ alkynyl;
- each of R$^5$ or R$^{5'}$ is independently NH$_2$, CO$_2$H, H, OH, C$_1$-C$_{10}$ alkyl, C$_2$-C$_{10}$ alkenyl, C$_2$-C$_{10}$ alkynyl, or -L;
- each of R$^7$ and R$^{7'}$ is H;
- X is:
    - C$_{1-12}$ alkylene, optionally wherein the alkylene chain is interrupted by one or more hetero atoms selected from the group consisting of O, S, and NH; or
    - —(CH$_2$)$_m$-Q-(CH$_2$)$_p$—, wherein m and p are each independently 0, 1 or 2;

Q has a structure of formula:

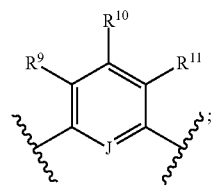

wherein each of R$^9$, R$^{10}$ and R$^{11}$ is H, NH$_2$, CO$_2$H, -L; and
J is CH or N;
- each of Y and Y' is independently O, S, or NH;
- each of Z and Z' is independently H, R, OH, OR, SH, SR, NH$_2$, or NHR, where each R is independently unsubstituted C$_1$-C$_{12}$ alkyl; and
- wherein only one of R$^b$, R$^{b'}$, R$^5$, R$^{5'}$, R$^9$, R$^{10}$, and R$^{11}$ is -L.

8. The method of claim 7, wherein IQB is a moiety having the structure:

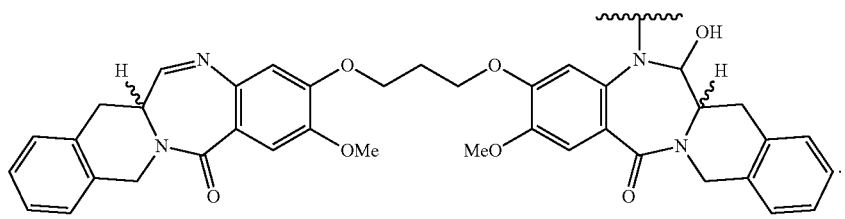 [SMILES: *N1c2cc(OCCCOc3cc4c(cc3OC)C(=O)N3Cc5ccccc5CC3C=N4)c(OC)cc2C(=O)N2Cc3ccccc3CC2C1O]

9. The method of claim 7 wherein —W—R$_M$-L-IQB is a moiety having a structure of Formula IV:

Formula IV

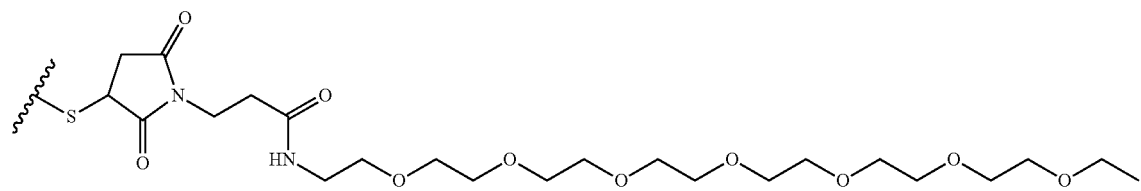

-continued

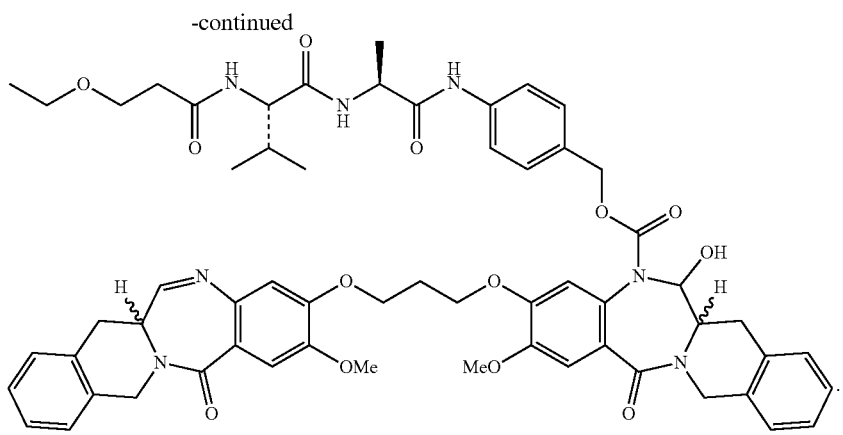

10. The method of claim 7 wherein the antibody is a cysteine substituted antibody.

11. The method of claim 7 wherein the cancer marker is selected from GPR114, CLL-1, IL1RAP, CD33 and CD123/IL3Ra.

12. The method according to claim 1, wherein
each of $R^a$ and $R^{a'}$ is independently H, or OH;
if present, each of $R^b$ and $R^{b'}$ is H;
$R^2$, $R^{2'}$, $R^3$, $R^{3'}$, $R^4$, $R^{4'}$, $R^{6'}$, $R^6$, $R^7$ and $R^{7'}$, are each H;
each of $R^5$ and $R^{5'}$ is H;
X is:
$C_{1-12}$ alkylene, optionally wherein the alkylene chain is interrupted by one or more hetero atoms selected from the group consisting of O, S, and NH; or
—$(CH_2)_m$-Q-$(CH_2)_p$—, wherein m and p are each independently 0, 1 or 2;
Q has a structure of formula:

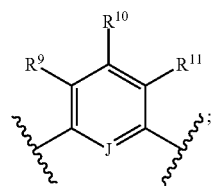

wherein each of $R^9$, $R^{10}$ and $R^{11}$ is H, or -L-$R_x$; and J is CH;
each of Y and Y' is O;
each of Z and Z' is independently OR, where each R is independently unsubstituted $C_1$-$C_3$ alkyl.

13. The method according to claim 7, wherein
each of $R^a$ and $R^{a'}$ is independently H, or OH;
if present, each of $R^b$ and $R^{b'}$ is independently H, or L-$R_x$;
$R^2$, $R^{2'}$, $R^3$, $R^{3'}$, $R^4$, $R^{4'}$, $R^{6'}$, $R^6$, $R^7$ and $R^{7'}$, are each H;
each of $R^5$ and $R^{5'}$ is independently H, or L-$R_x$;
X is:
$C_{1-12}$ alkylene, optionally wherein the alkylene chain is interrupted by one or more hetero atoms selected from the group consisting of O, S, and NH; or
—$(CH_2)_m$-Q-$(CH_2)_p$—, wherein m and p are each independently 0, 1 or 2;
Q has a structure of formula:

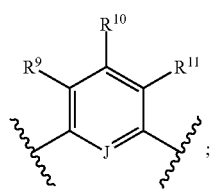

wherein each of $R^9$, $R^{10}$ and $R^{11}$ is H, or -L-$R_x$; and J is CH;
each of Y and Y' is O;
each of Z and Z' is independently OR, where each R is independently unsubstituted $C_1$-$C_3$ alkyl; and
-L-$R_x$ is the linker L attached to the reactive moiety $R_x$;
wherein only one of $R^b$, $R^{b'}$, $R^5$, $R^{5'}$, $R^9$, $R^{10}$, and $R^{11}$ is L-$R_x$.

14. The method of claim 7, wherein the antibody or antibody fragment specifically binds to CLL-1.

15. The method of claim 7, wherein W is a thiol of a cysteine residue, an amino group of a lysine residue, an azide group substituted on an amino acid or an aldehyde or ketone substituted on an amino acid.

16. The method of claim 7, wherein Y and Y' are each O.

17. The method of claim 7, wherein Z and Z' are each independently OR, where each R is independently unsubstituted $C_1$-$C_3$ alkyl.

18. The method of claim 7, wherein X is —$CH_2$—.

19. An antibody-drug conjugate having a structure of Formula III:

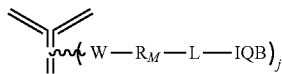
Formula III wherein:

is an antibody or antibody fragment that binds to a cancer marker on an AML cell;

W—$R_M$ is a linking moiety formed by W and $R_x$, wherein W is a moiety attached to a natural or unnatural amino acid residue of the antibody/antibody fragment and $R_x$ is a reactive moiety linking L-IQB to the antibody wherein $R_x$ is selected from iodoacetamide, succinimidyl, maleimidyl, cyclooctynyl, aminooxy, bisulfonyl, sulfonyl, or isothiocyanate moiety, such that W—$R_M$ is a disulfide, a thiolated succinimidyl, an amino substituted succinimidyl, a (cyclooctyl)-1, 4 triazolyl, oxime substituted N-glycan, oxime, a substituted bis-sulfopropyl, a sulfonamidyl, an amide, or a thiocarbamate moiety;

L is a linker comprising polyethylene glycol and 1-10 amino acid moieties; and,

IQB is a compound having a structure of Formula (I):

each of $R^b$ and $R^{b'}$ is not present or is independently H, or -L;

$R^2$, $R^{2'}$, $R^3$, $R^{3'}$, $R^4$, $R^{4'}$, $R^{6'}$ and $R^6$ are each independently selected from H, OH, $C_1$-$C_{10}$ alkyl, $C_2$-$C_{10}$ alkenyl or $C_2$-$C_{10}$ alkynyl;

each of $R^5$ or $R^{5'}$ is independently $NH_2$, $CO_2H$, H, OH, $C_1$-$C_{10}$ alkyl, $C_2$-$C_{10}$ alkenyl, $C_2$-$C_{10}$ alkynyl, or -L;

each of $R^7$ and $R^{7'}$ is H;

X is:

$C_{1-12}$ alkylene, optionally wherein the alkylene chain is interrupted by one or more hetero atoms selected from the group consisting of O, S, and NH; or —$(CH_2)_m$-Q-$(CH_2)_p$—, wherein m and p are each independently 0, 1 or 2;

Q has a structure of formula:

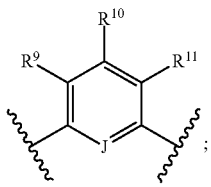

wherein each of $R^9$, $R^{10}$ and $R^{11}$ is H, $NH_2$, $CO_2H$, -L; and

J is CH or N;

each of Y and Y' is independently O, S, or NH;

each of Z and Z' is independently H, R, OH, OR, SH, SR, $NH_2$, or NHR, where each R is independently unsubstituted $C_1$-$C_{12}$ alkyl; and wherein only one of $R^b$, $R^{b'}$, $R^5$, $R^{5'}$, $R^9$, $R^{10}$, and $R^{11}$ is -L.

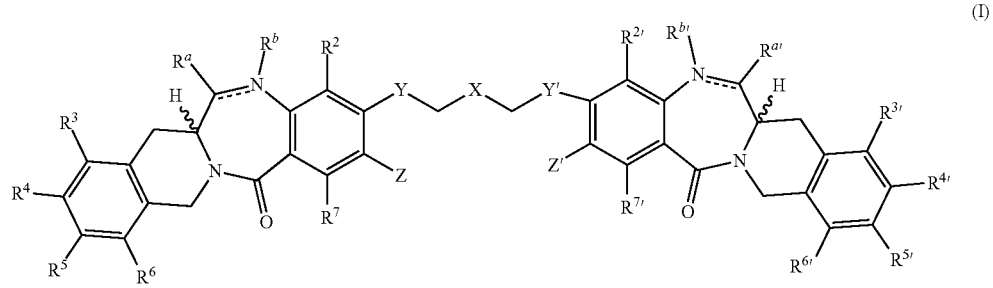
(I)

wherein:

the dotted bond shown between —C($R^a$)— and —N($R^b$)— or —C($R^{a'}$)— and —N($R^{b'}$)— is independently a single bond or a double bond;

each of $R^a$ and $R^{a'}$ is independently H, OH, or —O—P, where P is a protecting group;

20. The antibody-drug conjugate of claim 19, wherein IQB is a moiety having the structure:

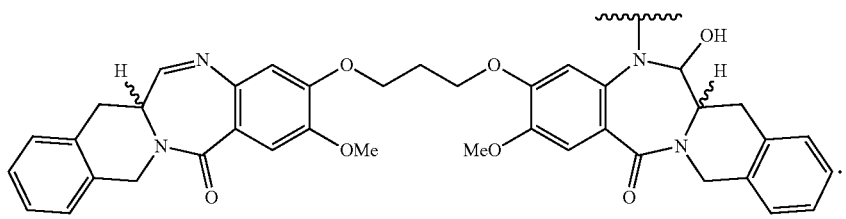 [SMILES: *N1c2cc(OCCCOc3cc4c(cc3OC)C(=O)N3Cc5ccccc5CC3C=N4)c(OC)cc2C(=O)N2Cc3ccccc3CC2C1O]

21. The antibody-drug conjugate of claim 19, wherein —W—R$_M$-L-IQB is a moiety having a structure of Formula IV:

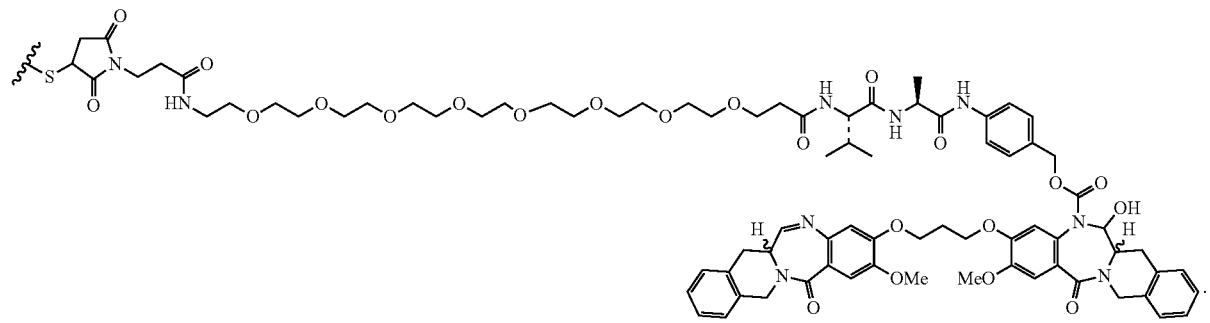

Formula IV

22. The antibody-drug conjugate of claim 19, wherein the antibody is a cysteine substituted antibody.

23. The antibody-drug conjugate of claim 19, wherein the cancer marker is selected from GPR114, CLL-1, IL1RAP, CD33 and CD123/IL3Ra.

24. The antibody-drug conjugate of claim 19, wherein
each of R$^a$ and R$^{a'}$ is independently H, or OH;
if present, each of R$^b$ and R$^{b'}$ is independently H, or L;
R$^2$, R$^{2'}$, R$^3$, R$^{3'}$, R$^4$, R$^{4'}$, R$^{6'}$, R$^6$, R$^7$ and R$^{7'}$, are each H;
each of R$^5$ and R$^{5'}$ is independently H, or L;
X is:
  C$_{1-12}$ alkylene, optionally wherein the alkylene chain is interrupted by one or more hetero atoms selected from the group consisting of O, S, and NH; or
  —(CH$_2$)$_m$-Q-(CH$_2$)$_p$—, wherein m and p are each independently 0, 1 or 2;
Q has a structure of formula:

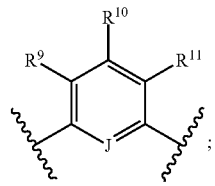

wherein each of R$^9$, R$^{10}$ and R$^{11}$ is H, or -L; and
J is CH;
each of Y and Y' is O;

each of Z and Z' is independently OR, where each R is independently unsubstituted C$_1$-C$_3$ alkyl; and L is the linker;

wherein only one of R$^b$, R$^{b'}$, R$^5$, R$^{5'}$, R$^9$, R$^{10}$ and R$^{11}$ is L.

25. The antibody-drug conjugate of claim 16, wherein the antibody or antibody fragment specifically binds to CLL-1.

26. The antibody-drug conjugate of claim 19, wherein W is a thiol of a cysteine residue, an amino group of a lysine residue, an azide group substituted on an amino acid or an aldehyde or ketone substituted on an amino acid.

27. The antibody-drug conjugate of claim 19, wherein Y and Y' are each O.

28. The antibody-drug conjugate of claim 19, wherein Z and Z' are each independently OR, where each R is independently unsubstituted C$_1$-C$_3$ alkyl.

29. The antibody-drug conjugate of claim 19, wherein rein X is —CH$_2$—.